US007323560B2

(12) United States Patent
Allen et al.

(10) Patent No.: US 7,323,560 B2
(45) Date of Patent: Jan. 29, 2008

(54) PLASTIDIC PHOSPHOGLUCOMUTASE GENES

(75) Inventors: Stephen M. Allen, Wilmington, DE (US); Karlene H. Butler, Newark, DE (US); Thomas J. Carlson, Ann Arbor, MI (US); William D. Hitz, Wilmington, DE (US); Johan M. Stoop, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/094,586

(22) Filed: Mar. 30, 2005

(65) Prior Publication Data

US 2005/0273886 A1    Dec. 8, 2005

Related U.S. Application Data

(63) Continuation-in-part of application No. 09/906,209, filed on Jul. 16, 2001, now Pat. No. 7,250,557.

(60) Provisional application No. 60/218,712, filed on Jul. 17, 2000.

(51) Int. Cl.
*C12N 15/52* (2006.01)
*C07H 21/04* (2006.01)
*C07K 14/415* (2006.01)
*C12N 5/14* (2006.01)
*C12N 9/00* (2006.01)
*A01H 1/00* (2006.01)

(52) U.S. Cl. .................. 536/24.5; 435/6; 435/468; 435/426; 435/419; 435/252.3; 435/320.1; 435/183; 530/370; 536/23.2; 800/278; 800/295

(58) Field of Classification Search .............. 435/6, 435/69.1, 468, 419, 252.3, 320.1; 530/370; 536/23.6; 800/278, 295
See application file for complete search history.

(56) References Cited

U.S. PATENT DOCUMENTS

| 5,231,020 | A | | 7/1993 | Jorgensen et al. |
| 5,648,249 | A | * | 7/1997 | Barry et al. ............. 800/284 |
| 5,846,784 | A | | 12/1998 | Hitz |
| 6,057,493 | A | | 5/2000 | Willmitzer et al. |
| 6,232,529 | B1 | * | 5/2001 | Singletary et al. ......... 800/281 |
| 2002/0165385 | A1 | | 11/2002 | Allen et al. |
| 2004/0031072 | A1 | | 2/2004 | La Rosa et al. |

FOREIGN PATENT DOCUMENTS

| EP | 1001029 A1 | 5/2000 |
| EP | 0 455 316 B1 | 12/2003 |
| WO | WO 94/11516 A1 | 5/1994 |
| WO | WO 98/22604 A1 | 5/1998 |
| WO | WO 98/01574 A1 | 9/1998 |
| WO | WO 99/29161 | 6/1999 |
| WO | WO 99/36551 A1 | 7/1999 |
| WO | WO 00/11176 A2 | 3/2000 |
| WO | WO 01/75128 A2 | 10/2001 |

OTHER PUBLICATIONS

Proceedings Soybean Utilization Alternatives, University of Minnesota, Craig Coon et al., pp. 203-211, 1988, The Effect of Oligosaccharides on the Nutritive Value of Soybean Meal.
National Center for Biotechnology Information General Identifier No. 6272125, Nov. 4, 1999, C. J. Harrison et al., The Rug3 Locus of Pea Encodes a Plastidal Phosphoglucomutase.
National Center for Biotechnology Information General Identifier No. 6272283, Nov. 4, 1999, C.J. Harrison et al., The Rug3 Locus of Pea Encodes Plastidal Phosphoglucomutase.
National Center for Biotechnology Information General Identifier No. 10190529, Sep. 16, 2000, C.J. Harrison et al., Method for Increasing Sucrose Content of Plants.
T. M. Klein et al., Nature, vol. 327:70-73, 1987, High-Velocity Microprojectiles for Delivering Nucleic Acids Into Living Cells.
EMBL Sequence Database Library Accession No. AW7819992, May 14, 2000, R. Shoemaker et al., Public Soybean EST Project.
EMBL Sequence Database Library Accession No. AC002311, Jul. 10, 1997, N. A. Federspiel et al.
EMBL Sequence Database Library Accession No. AI1416493, Feb. 11, 1999, R. Shoemaker et al., Public Soybean EST Project.
EMBL Sequence Database Library Accession No. U84888, Feb. 8, 1997, C. B. Michalowski et al., Mesembryanthemum Crystallinum Phosphoglucomutase MRNA.
National Center for Biotechnology Information General Identifier No. 13487785, Accession No. AAK27719, Dated Apr. 29, 2002, S. Singh et al., Isolation and characterization of cDNA clones encoding ADP-glucose pyrophorylase (AGPase) large and small subunits from chickpea (*Cicer arietinum* L.).
National Center for Biotechnology Information General Identifier No. 29421116, Accession No. BAC66693, Dated Feb. 25, 2004, D. Omoto et al., Isolation and characterization of two cDNAs for large and small subunits of ADP-glucose pyrophosphorylase from kidney bean.
Official Methods of Analysis of AOAC International, 990.03, 2000 (book not supplied).
Official Methods of Analysis of AOAC International, 920.39, 2000 (book not supplied).
Cyril Periappuram et al., The Plastidic Phosphoglucomutase from Arabidopsis. A Reversible Enzyme Reaction with an Important Role in Metabolic Control, Plant Physiology, vol. 122:1193-1199, Apr. 2000.
National Center for Biotechnology Information General Identifier No. 6272125, Accession No. CAB60109, Apr. 15, 2005, C. J. Harrison et al., The rug3 locus of pea encodes plastidial phosphoglucomutase.

(Continued)

*Primary Examiner*—Phuong T Bui

(57) ABSTRACT

An isolated nucleic acid fragment encoding a plastidic phosphoglucomutase protein is disclosed. Also disclosed is the construction of a chimeric gene encoding all or a substantial portion of the plastidic phosphoglucomutase, in sense or antisense orientation, wherein expression of the chimeric gene results in production of altered levels of the plastidic phosphoglucomutase in a transformed host cell.

7 Claims, 8 Drawing Sheets

OTHER PUBLICATIONS

National Center for Biotechnology Information General Identifier No. 6272283, Accession No. CAB60128, Apr. 15, 2005, C. J. Harrison et al., The rug3 locus of pea encodes plastidial phosphoglucomutase.

National Center for Biotechnology Information General Identifier No. 10190529, Accession No. CAC09323, Sep. 16, 2000, C. J. Harrison et al., Method for increasing sucrose content of plants.

Taiz, L. et al., Plant Physiology; The Benjamin/Cummings Publishing Company; New York, 1991 (book not supplied).

Timothy Caspar et al., Alterations in Growth, Photosynthesis, and Respiration in a Starchless Mutant of *Arabidopsis thaliana* (L.) Deficient in Chloroplast Phosphoglucomutase Activity, Plant Physiology, vol. 79:11-17, 1985.

Steven C. Huber et al., Carbon Partitioning and Growth of a Starchless Mutant of *Nicotiana sylvestris*, Plant Physiol., vol. 99:1449-1454, 1992.

Rod Casey et al., The Effect of Modifying Carbohydrate Metabolism on Seed Protein Gene Expression in Peas, J. Plant Physiol., vol. 152:636-640, 1998.

Christopher Brown et al., Reserve mobilization and starch formation in soybean (Glycine max) cotyledons in relation to seedling growth, Physiologica Plantarum, vol. 72:518-524, 1988.

Ann Depicker et al., Post-Transcriptional Gene Silencing in Plants, Current Opinion in Cell Biology, vol. 9:373-382, 1997.

* cited by examiner

FIG. 1A

```
SEQ ID NO: 12    1  MAF------CY-RLDN-FIISAFKPKHSNVPLSI------HHSS--SNFPSFKVQNFPFR
SEQ ID NO: 13    1  MAF------CY-RLDN-FIISAFKPKHSNVPLSI------HHSS--SNFPSFKVQNFPFR
SEQ ID NO: 08    1  MAF------SC-KLDS-FILSAYKPQNSILPLSI------QPSSFLPSPSSLKPQKLPFR
SEQ ID NO: 04    1  M---------------------------PTM---------------HALRLCPLL--
SEQ ID NO: 10    1  TRLARFLPRCKRNTTSPHSPSRLFSPSPPPLLSAWRWHCRPPHRLGMASHALRLHPLLFS
SEQ ID NO: 02    1  AP-ARY------RHLSLSQSLSPYL---------------QEMAMSVPTMRLHPLVPS
SEQ ID NO: 11    1  MSS------TYARFDTVFLLSRF-AGAKYSPLWP------SSSS--SSHSSLLSSGIHLR
                    1                                                              60

*   * ***** *
SEQ ID NO: 12   45  VRYNSAIRATSSSSSTPTT--IA-------------------------EPNDIKINSIPTKPIEGQ
SEQ ID NO: 13   45  VRYNSAIRATSSSSSTPTT--IA-------------------------EPNDIKINSIPTKPIEGQ
SEQ ID NO: 08   47  IRYGSTIRATSSSSTPSAT--IA-------------------------EPEGIKIKSIPTKPIDGQ
SEQ ID NO: 04   14  -STIRSTP--PRATAAARQ----G----AL-FVARCSSAGTPSAAQALKISSIPTKPVEGQ
SEQ ID NO: 10   61  AAAARPAPLAARPGGGARR---VHRRHSL-AVVRCSS----SAAQALKIKSIPTKPVEGQ
SEQ ID NO: 02   37  SKLLSPSSSSPAVLVSSRIPLLSLRRPNLRFSVKATASSTPSTAESIKIKSIPTKPVEGQ
SEQ ID NO: 11   46  AKPNSRLRSVTGASSSSSGPIIA-------------------------GSESIEIKSLPTKPIEGQ
                    61                                                            120

************** * *********************** *** ********** * ***  *
SEQ ID NO: 12   84  KTGTSGLRKKVKVFKQENYLANWIQALFNSLPPEDYKNGLLVLGGDGRYFNKEAAQIIIK
SEQ ID NO: 13   84  KTGTSGLRKKVKVFKQENYLANWIQALFNSLPPEDYKNGLLVLGGDGRYFNKEAAQIIIK
SEQ ID NO: 08   86  KTGTSGLRKKVKVFKQENYLANWIQALFNSLPPEDYKNGLLVLGGDGRYFNKEAAQIIIK
SEQ ID NO: 04   63  KTGTSGLRKKVKVFQQENYLANWIQALFNSLPPEDYKNGVGATLVLGGDGRYFNQEAAQIIIK
SEQ ID NO: 10  113  KTGTSGLRKKVKVFQQENYLANWIQALFNSLPPEDYKNGVGGTLVLGGDGRYFNKEAAQIIIK
SEQ ID NO: 02   97  KTGTSGLRKKVKVFQQENYLANWIQALFNSLPLEDYKNGLLVLGGDGRYFNKDAAQIITK
SEQ ID NO: 11   87  KTGTSGLRKKVKVFMQDNYLANWIQALFNSLPLEDYKDATLVLGGDGRYFNKEASQIIIK
                    121                                                           180
```

FIG. 1B

```
                  *********************  *  *************************
SEQ ID NO: 12  144 IAAGNGVGKILVGKEGILSTPAVSAVIRKREANGGFIMSASHNPGGPEYDWGIKFNYSSG
SEQ ID NO: 13  144 IAAGNGVGKILVGKEGILSTPAVSAVIRKREANGGFIMSASHNPGGPEYDWGIKFNYSSG
SEQ ID NO: 08  146 IAAGNGVGKILVGKEGILSTPAVSAVIRKRKANGGFIMSASHNPGGPEYDWGIKFNYSSG
SEQ ID NO: 04  123 IAAGNGVQKIIVGRNGLLSTPAVSAVIRKRKANGGFIMSASHNPGGPDNDWGIKFNYSSG
SEQ ID NO: 10  173 IAAGNGVGKILVGRNGLLSTPAVSAVIRKRQANGGFIMSASHNPGGPDNDWGIKFNYSSG
SEQ ID NO: 02  157 IAAGNGVGKILVGRDGIMSTPAVSAVIRKQKANGGFIMSASHNPGGPDYDWGIKFNYSSG
SEQ ID NO: 11  147 IAAGNGVGKILVGQEGILSTPAVSAVIRKRKANGGFIMSASHNPGGPEYDWGIKFNYSSG
                                                                       240
                   181

*******  ***  *  ***************  **  *    ******** *
SEQ ID NO: 12  204 QPAPESITDKIYGNTLSISEIKIADIPDVDLSNVGVTKFGSFSVEVIDPVSDYLELLETV
SEQ ID NO: 13  204 QPAPESITDKIYGNTLSISEIKIADIPDVDLSNVGVTKFGSFSVEVIDPVSDYLELLETV
SEQ ID NO: 08  206 QPAPESITDKIYGNTLSISEIKIADIPDVDLSKVGVTNFGSFSVEVIDPVSDYLELLETV
SEQ ID NO: 04  183 QPAPETITDKIYGNTLSISEIKTADIPDTDLSSVGVVSYGDFAIEVIDPVSDYLELMENV
SEQ ID NO: 10  233 QPAPESITDKIYGNTLSISEIKTADIPDVDLSSLGVVSYGDFTVEVIDPVLDYLELMENV
SEQ ID NO: 02  217 QPAPESITDKIYGNTLSISEIKISDIPDIDLSSLGVTNYGNFSVEVVDPVSDYLELMENV
SEQ ID NO: 11  207 QPAPESITDKIYGNTLSISEIKVAEIPDIDLSHVGVTKYGNFSVEVIDPISDYLELMEDV
                                                                       300
                   241

***  ** *     ****** ****       *              *******
SEQ ID NO: 12  264 FDFQLIKSLISRPDFRFTFDAMHAVAGAYATPIFVDKLSASLDSISNGIPLEDFGHGHPD
SEQ ID NO: 13  264 FDFQLIKSLISRPDFRFTFDAMHAVAGAYATPIFVDKLGASPDSISNGIPLEDFGHGHPD
SEQ ID NO: 08  266 FDFQLIRGLLSRPDFRFIFDAMHAVTGAYAKPIFVDKLGASLDSISNGIPLEDFGHGHPD
SEQ ID NO: 04  243 FDFQLIRGLLSRPDFRFIFDAMHAITGAYAGPIFVEKLGADPDCILNGVPLEDFGNGHPD
SEQ ID NO: 10  293 FDFQLIKGLLSRPDFRFVFDAMHAVTGAYADPIFVEKLGADPDYILNGVPLEDFGNGHPD
SEQ ID NO: 02  277 FDFQLIKGLLSRSDFRFTFDAMHAVTGAYAKPIFVERLRASPDCVLNGVPLEDFGHGHPD
SEQ ID NO: 11  267 FDFDLIRGLLSRSDFGFMFDAMHAVTGAYAKPIFVDNLEAKPDSISNGVPLEDFGHGHPD
                                                                       360
                   301
```

FIG. 1C

```
                       *********  **                ** ********       **  ******  **
SEQ ID NO: 12    324   PNLTYAKDLVKIMYAENGPDFGAASDGDGDRNMILGTSFFVTPSDSVAVIAANAKEAIPY
SEQ ID NO: 13    324   PNLTYAKDLVNIMYAENGPDFGAASDGDGDRNMILGTSFFVTPSDSVAVIAANAKEAIPY
SEQ ID NO: 08    326   PNLTYAKDLVDILYAENGPDFGAASDGDGDRNMILGRSFFVTPSDSVAVIAANAREAIPY
SEQ ID NO: 04    303   PNLTYAKELVFTMFGTHAPDFGAASDGDGDRNMILGKRFFITPSDSVAIIAANAQTAIPY
SEQ ID NO: 10    353   PNLTYAKELVFTMFGSGAPDFGAASDGDGDRNMILGRRFFVTPSDSVAIIAANAQAAIPY
SEQ ID NO: 02    337   PNLTYAKELVDVMYTTDAPDLGAASDGDGDRNMILGRRFFVTPSDSVAMIAANAQAAIPY
SEQ ID NO: 11    327   PNLTYAKDLVDVMYRDDGPDFGAASDGDGDRNMVLGNKFFVTPSDSVAIIAANAQEAIPY
                                                   361                                420

*  *********  **             *         **    **   ******  *****
SEQ ID NO: 12    384   FKDSIKGLARSMPTSGALDRVAEKLNLPFFEVPTGWKFFGNLMDAGNLSICGEESFGTGS
SEQ ID NO: 13    384   FKDSIKGLARSMPTSGALDRVAEKLNLPFFEVPTGWKFFGNLMDAGNLSICGEESFGTGS
SEQ ID NO: 08    386   FKNGVKGLARSMPTSGALDRVAKKLNLPFFEVPTGWKFFGNLMDAGNLSVCGEESFGTGS
SEQ ID NO: 04    363   FQFGTKGLARSMPPSGALDRVAEKLNVPFFEVPTGWKFFGNLMDAGKLSICGEESFGTGS
SEQ ID NO: 10    413   FQSGPKGLARSMPTSGALDRVADKLNVPFFEVPTGWKFFGNLMDAGKLSICGEESFGTGS
SEQ ID NO: 02    397   FQAGPKGLARSMPTSGALDRVAEKLNLPFFEVPTGWKFFGNLMDAGKLSICGEESFGTGS
SEQ ID NO: 11    387   FRAGPKGLARSMPTSGALDRVAEKLKLPFFEVPTGWKFFGNLMDAGKLSICGEESFGTGS
                                                   421                                480

**********  ******  **  **   *          **     *   *   *********
SEQ ID NO: 12    444   DHIREKDGIWAVLAWLSIIAHRNKDTKPGEKLVSVSDVVKEHWATYGRNFFSRYDYEECE
SEQ ID NO: 13    444   DHIREKDGIWAVLAWLSIIAHRNKDTKPGEKLVSVSDVVKEHWATYGRNFFSRYDYEECE
SEQ ID NO: 08    446   DHIREKDGIWAVLAWLSIIAHRNKDKNPGEKLISVSDVVMEHWATYGRNFFSRYDYEECE
SEQ ID NO: 04    423   DHIREKDGIWAVLAWLSILAHRNKDKKVGERLVSVEDIAMEHWKTYGRNFFSRYDYEACE
SEQ ID NO: 10    473   DHIREKDGIWAVLAWLSILAHRNKDKKAGERLVSVEDVAREHWATYGRNFFSRYDYEECE
SEQ ID NO: 02    457   DHIREKDGIWAVLAWLSIIAYRNKDKKIGEKLVSVEDIAKEHWAKYGRNFFSRYDYEECE
SEQ ID NO: 11    447   DHIREKDGIWAVLAWLSILAHRIKDKKPGEKLVSVADVVNEYWATYGRNFFSRYDYEECE
                                                   481                                540
```

FIG. 1D

```
                    *        *    **     * **  *  *******    ****    *********
SEQ ID NO: 12  504  SEGANKMIEYLRELLSKSKPGDKYGSYVLQFADDFTYTDPVDGSVVSKQGVRFVFTDGSR
SEQ ID NO: 13  504  SEGANKMIEYLRELLSKSKPGDKYGSYVLQFADDFTYTDPVDGSVVSKQGVRFVFTDGSR
SEQ ID NO: 08  506  SEGANKMIEYLRDILSKSKPGDQYGSYVLQFADDFTYTDPVDGSVVSKQGVRFVFTDGSR
SEQ ID NO: 04  483  SHSANQMMDHLRDVMANSKPGEKYGNYTLQFADDFSYTDPVDGSTVSKQGLRFVFTDGSR
SEQ ID NO: 10  533  SESANKMMEHLRDVIAKSKPGEKYGNYTLQFADDFSYTDPVDGSTVSKQGLRFVFTDGSR
SEQ ID NO: 02  517  SEGANKMMQHLRDFISTSKPGEQYGNYTLQFSDDFSYTDPVDGSVASKQGLRFVFTDGSR
SEQ ID NO: 11  507  SEGANKMIEYLRDIVAKSKAGENYGNYVLQFADDFSYKDPVDGSVASKQGVRFVFTDGSR
                    541                                                      600

* ****  ******** * *  ***  *   ********* ************ ***
SEQ ID NO: 12  564  IIYRLSGTGSAGATVRVYIEQFEPDVSKHDVDAQIALKPLIDLALSVSKLKDFTGREKPT
SEQ ID NO: 13  564  IIYRLSGTGSAGATVRVYIEQFEPDVSKHDVDAQIALKPLIDLALSVSKLKDFTGREKPT
SEQ ID NO: 08  566  IIYRLSGTGSAGATVRVYIEQFEPDVSKHDVDAQIALKPLIDLAISVSKLKDFTGREKPT
SEQ ID NO: 04  543  IIFRLSGTGSAGATIRLYIEQFESDISKHSLDAQTALKPLIDLALSVSKLKDFTGREKPT
SEQ ID NO: 10  593  IIFRLSGTGSAGATIRIYIEQFESDASKHDLDAQIALKPLIDLALSVSKLKDFTGRDKPT
SEQ ID NO: 02  577  VIYRLSGTGSAGATIRIYVEQFEPDVSKHDVDAQAALKPLIDLALSISKLKEFTGREKPT
SEQ ID NO: 11  567  IIYRLSGNGSAGATVRIYIEQFEPDVSKHDVDAQIAIKPLIDLALSVSKLKEFTGREKPT
                    601                                                      660

***
SEQ ID NO: 12  624  VIT
SEQ ID NO: 13  624  VIT
SEQ ID NO: 08  626  VIT
SEQ ID NO: 04  603  VIT
SEQ ID NO: 10  653  VIT
SEQ ID NO: 02  637  VIT
SEQ ID NO: 11  627  VIT
                    661 663
```

FIGURE 2
Starch accumulation in PGM-wt and PGM-ko soybeans
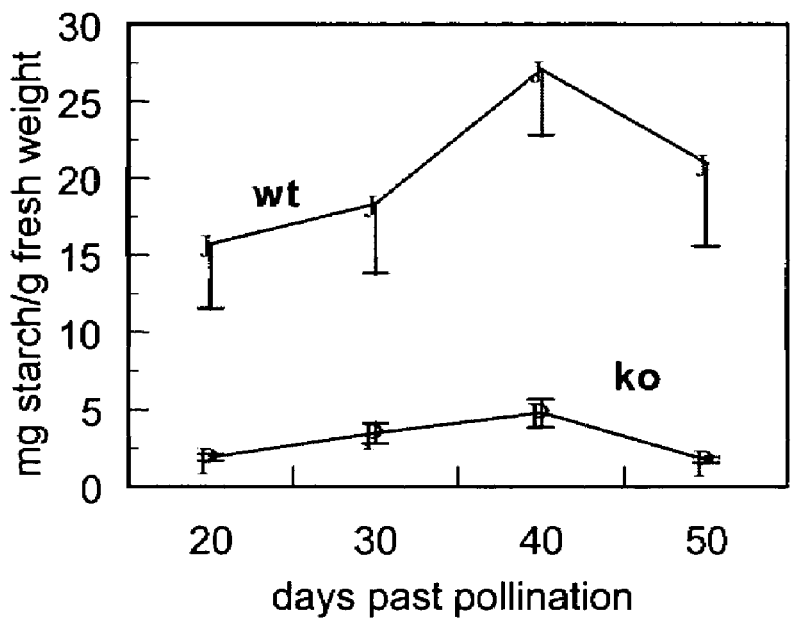
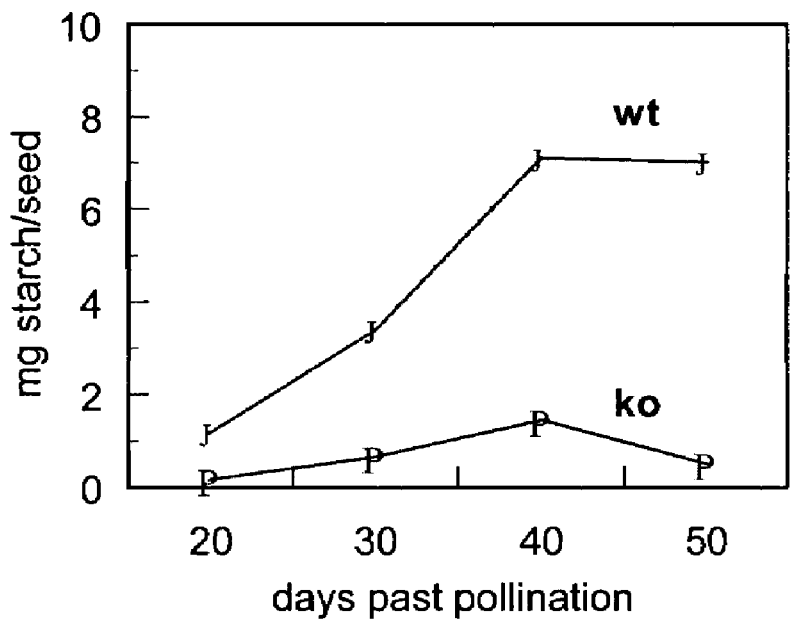

FIGURE 3

Soluble Carbohydrate Concentrations of Growth Chamber (GC) or Field Grown (field) T2 Seeds from PGM-Silenced Events (KO) as Compared to Their Null Segregants (WT)

| Event | Pedigree | ID | Pheno-type | Growth Condition | % CHO (mg/100 mg seed) | | | Sucrose/RFO | % Change | | |
|---|---|---|---|---|---|---|---|---|---|---|---|
| | | | | | Sucrose | RFO | Total CHO | | Sucrose | RFO | Total CHO |
| 108-3-1-1 | 92B91 | pot-1 | KO | GC | 2.68 | 3.62 | 7.16 | 0.71 | -38.10 | 17.68 | -10.68 |
| 108-3-1-1 | 92B91 | 2097-7 | KO | field | 2.65 | 2.89 | 6.02 | 0.92 | -38.87 | -5.79 | -24.88 |
| 108-3-1-1 | 92B91 | 2097-1 | WT | field | 4.33 | 3.07 | 8.01 | 1.42 | --- | --- | --- |
| 105-1-8-2 | Jack | 2086-1 | KO | field | 2.46 | 2.66 | 5.48 | 0.92 | -29.36 | +15.80 | -13.34 |
| 105-1-8-2 | Jack | 2086-11 | WT | field | 3.49 | 2.30 | 6.32 | 1.53 | --- | --- | --- |
| 105-1-7-3 | Jack | 2084-2 | KO | field | 2.70 | 2.93 | 6.07 | 0.92 | -31.48 | -4.40 | -18.46 |
| 105-1-7-3 | Jack | 2084-11 | WT | field | 3.94 | 3.07 | 7.44 | 1.28 | --- | --- | --- |
| Control | 92B91 | --- | WT | field | 4.75 | 3.27 | 8.67 | 1.46 | --- | --- | --- |
| Control | Jack | --- | WT | field | 5.12 | 3.04 | 8.77 | 1.67 | --- | --- | --- | nd = not determined

FIGURE 4

Soluble Carbohydrate Concentrations of T3 Seeds from PGM-Silenced Events as Compared to Wild-Type

| Event | Pedigree Background | ID | Phenotype | % CHO (mg/100 mg seed) | | | Sucrose/RFO | % Change | | |
|---|---|---|---|---|---|---|---|---|---|---|
| | | | | Sucrose | RFO | Total Soluble Sugars | | Sucrose | RFO | Total Soluble Sugars |
| 108-3-1-1 | 92B91 | 26-1 to 9 | KO | 3.01 | 2.45 | 6.15 | 1.22 | -35.90 | -14.23 | -24.82 |
| 108-3-1-1 | 92B91 | 26-42 | WT | 4.70 | 2.86 | 8.18 | 1.64 | --- | --- | --- |
| 105-1-8-2 | Jack | 27-16 | KO | 2.99 | 2.39 | 5.88 | 1.25 | -48.27 | -14.02 | -34.37 |
| 100-2-1-1 | Jack | 29-36 | KO | 3.49 | 2.37 | 6.24 | 1.50 | -39.61 | -14.75 | -30.36 |
| 101-2-6-3 | Jack | 30-37 | WT | 5.78 | 2.78 | 8.96 | 2.09 | --- | --- | --- |

FIGURE 5

Soluble Carbohydrate Profile of Defatted Soybean Meal from T2 Seeds

| Event | Pedi-gree | ID | Pheno-type | Growth Condi-tion | % CHO (mg/100 mg Seed) | | | Sucrose/RFO | % Change | | |
|---|---|---|---|---|---|---|---|---|---|---|---|
| | | | | | Sucrose | RFO | Total CHO | | Sucrose | RFO | Total CHO |
| 108-3-1-1 | 92B91 | 2097-7 | KO | GC | 3.74 | 4.29 | 8.82 | 0.87 | -28.58 | 1.89 | -13.46 |
| 108-3-1-1 | 92B91 | 2097-7 | KO | field | 3.34 | 4.1 | 8.18 | 0.82 | -36.22 | -2.80 | -19.69 |
| 108-3-1-1 | 92B91 | 2097-1 | WT | field | 5.24 | 4.22 | 10.19 | 1.24 | --- | --- | --- |
| Control | 92B91 | --- | WT | field | 5.95 | 4.01 | 10.89 | 1.48 | --- | --- | --- |
| Control | Jack | --- | WT | field | 5.65 | 3.52 | 10.03 | 1.61 | --- | --- | --- |

SEQUENCE LISTING

<160> NUMBER OF SEQ ID NOS: 32

<210> SEQ ID NO 1
<211> LENGTH: 2112
<212> TYPE: DNA
<213> ORGANISM: Typha latifolia

<400> SEQUENCE: 1

```
gcaccagctc gttatcgcca cttatcgctc tctcaatctc tctctccata cttgcaagaa        60
atggcaatgt cggtgcctac tatgaggttg catcccctcg tccctcttc gaagcttctc         120 tctccctcct cttcgtcgcc ggcggtgctg gtctcttccc ggattcctct cctctctctt        180
aggaggccaa acctgaggtt ctccgtcaag gctaccgctt cttccactcc gtccacggcc        240
gaaagcataa agatcaagtc gatacccacc aagccagtag aagggcagaa gactgggact        300
agcggattaa ggaagaaggt taaggttttc cagcaggaga attacttggc aaactggatt        360
caggcactgt ttaattcctt gccgctggag gattacaaga atggattgct ggttttggga        420
ggtgatgggc ggtactttaa ccgagaggct gcacagataa tcatcaagat tgctgctgga        480
aatggtgttg gaaaaattct tgttggcagg gatggtatca tgtcaactcc tgctgtatct        540
gcagtaatac gtaaacagaa ggcaaatggt ggttttatca tgagtgcaag ccataatcct        600
ggtggtccgg actatgattg gggcattaag tttaattaca gcagtggaca acctgcacct        660
gaatcaatta ctgacaaaat ctacggtaac actctttcga tttctgaaat aaaaatatca        720
```

```
gatatacctg atattgatct atccagtcta ggtgttacca attatggcaa cttttctgtg    780
gaggtggtag accctgtttc agattacttg gagttaatgg agaatgtgtt tgattttcag    840
ctcatcaaag gtcttctttc tcgatctgat ttcaggttta catttgatgc gatgcatgca    900
gtaacaggtg catatgcaaa acctatcttt gtggaacggc ttcgagctag cccggattgt    960
gttttaaatg gagtgcctct tgaagatttt ggccatggtc acccagaccc caatctgacg   1020
tatgctaagg agcttgttga tgtaatgtat accacagatg cacctgatct aggagcagca   1080
agtgatggtg atggtgatcg aaacatgatt cttggaagac gtttctttgt tacaccatca   1140
gattctgttg caatgattgc cgctaatgca caggcggcta ttccttattt ccaagctggt   1200
cccaaaggac ttgctaggtc tatgccaaca agcggtgctc ttgatcgtgt agccgaaaaa   1260
ttgaaccttc cattctttga ggttccaact ggttggaagt tttttggaaa tctgatggat   1320
gctgggaagt tgtccatctg tggggaggaa agttttggca caggttctga tcacatccgg   1380
gagaaggatg gcatctgggc tgttttggct tggctttcca taattgcgta cagaaacaag   1440
gacaaaaaga ttggagagaa attagtctct gttgaagata ttgctaagga gcactgggca   1500
aaatatggca ggaacttctt ttctcgatat gattacgaag aatgcgaatc ggaaggagca   1560
aataaaatga tgcagcacct tagggacttt atctcgacaa gcaagcctgg agaacaatat   1620
ggaaattata ctcttcaatt ttcagatgac ttttcctaca ctgaccctgt agacggcagt   1680
gtagcatcca agcaagggct acgatttgtt ttcacagatg gatcaagggt tatctatcgt   1740
ctctcgggta ctggatcggc cggtgcaact atacggatat atgttgaaca attcgagccc   1800
gatgtctcca agcatgatgt ggatgcacaa gcagcattaa agcctttgat agacctcgca   1860
ttgtcgatat caaagctgaa ggaatttacc ggcaggggaga agcctacagt cattacatga   1920
gctgcatgga tggctaggta gcacgtatat tcttttattt tatgtgatgg cacgtccatt   1980
ttgctaataa agtaataatg taaagaagtc attacgcaga gtactagtct tttattatgc   2040
gatgcaacaa tcactcagtt ttgctattaa aaatgggact cacttctttc ccagaaaaaa   2100
aaaaaaaaaa aa                                                       2112
```

<210> SEQ ID NO 2
<211> LENGTH: 639
<212> TYPE: PRT
<213> ORGANISM: Typha latifolia

<400> SEQUENCE: 2

```
Ala Pro Ala Arg Tyr Arg His Leu Ser Leu Ser Gln Ser Leu Ser Pro
 1               5                  10                  15

Tyr Leu Gln Glu Met Ala Met Ser Val Pro Thr Met Arg Leu His Pro
             20                  25                  30

Leu Val Pro Ser Ser Lys Leu Leu Ser Pro Ser Ser Ser Ser Pro Ala
         35                  40                  45

Val Leu Val Ser Ser Arg Ile Pro Leu Leu Ser Leu Arg Arg Pro Asn
     50                  55                  60

Leu Arg Phe Ser Val Lys Ala Thr Ala Ser Ser Thr Pro Ser Thr Ala
 65                  70                  75                  80

Glu Ser Ile Lys Ile Lys Ser Ile Pro Thr Lys Pro Val Glu Gly Gln
                 85                  90                  95

Lys Thr Gly Thr Ser Gly Leu Arg Lys Lys Val Lys Val Phe Gln Gln
            100                 105                 110

Glu Asn Tyr Leu Ala Asn Trp Ile Gln Ala Leu Phe Asn Ser Leu Pro
```

```
                115                 120                 125
Leu Glu Asp Tyr Lys Asn Gly Leu Leu Val Leu Gly Asp Gly Arg
    130                 135                 140

Tyr Phe Asn Arg Glu Ala Ala Gln Ile Ile Lys Ile Ala Ala Gly
145                 150                 155                 160

Asn Gly Val Gly Lys Ile Leu Val Gly Arg Asp Gly Ile Met Ser Thr
                165                 170                 175

Pro Ala Val Ser Ala Val Ile Arg Lys Gln Lys Ala Asn Gly Gly Phe
                180                 185                 190

Ile Met Ser Ala Ser His Asn Pro Gly Pro Asp Tyr Asp Trp Gly
                195                 200                 205

Ile Lys Phe Asn Tyr Ser Ser Gly Gln Pro Ala Pro Glu Ser Ile Thr
    210                 215                 220

Asp Lys Ile Tyr Gly Asn Thr Leu Ser Ile Ser Glu Ile Lys Ile Ser
225                 230                 235                 240

Asp Ile Pro Asp Ile Asp Leu Ser Ser Leu Gly Val Thr Asn Tyr Gly
                245                 250                 255

Asn Phe Ser Val Glu Val Val Asp Pro Val Ser Asp Tyr Leu Glu Leu
                260                 265                 270

Met Glu Asn Val Phe Asp Phe Gln Leu Ile Lys Gly Leu Leu Ser Arg
    275                 280                 285

Ser Asp Phe Arg Phe Thr Phe Asp Ala Met His Ala Val Thr Gly Ala
    290                 295                 300

Tyr Ala Lys Pro Ile Phe Val Glu Arg Leu Arg Ala Ser Pro Asp Cys
305                 310                 315                 320

Val Leu Asn Gly Val Pro Leu Glu Asp Phe Gly His Gly His Pro Asp
                325                 330                 335

Pro Asn Leu Thr Tyr Ala Lys Glu Leu Val Asp Val Met Tyr Thr Thr
                340                 345                 350

Asp Ala Pro Asp Leu Gly Ala Ala Ser Asp Gly Asp Gly Asp Arg Asn
    355                 360                 365

Met Ile Leu Gly Arg Arg Phe Phe Val Thr Pro Ser Asp Ser Val Ala
    370                 375                 380

Met Ile Ala Ala Asn Ala Gln Ala Ala Ile Pro Tyr Phe Gln Ala Gly
385                 390                 395                 400

Pro Lys Gly Leu Ala Arg Ser Met Pro Thr Ser Gly Ala Leu Asp Arg
                405                 410                 415

Val Ala Glu Lys Leu Asn Leu Pro Phe Phe Glu Val Pro Thr Gly Trp
                420                 425                 430

Lys Phe Phe Gly Asn Leu Met Asp Ala Gly Lys Leu Ser Ile Cys Gly
    435                 440                 445

Glu Glu Ser Phe Gly Thr Gly Ser Asp His Ile Arg Glu Lys Asp Gly
    450                 455                 460

Ile Trp Ala Val Leu Ala Trp Leu Ser Ile Ile Ala Tyr Arg Asn Lys
465                 470                 475                 480

Asp Lys Lys Ile Gly Glu Lys Leu Val Ser Val Glu Asp Ile Ala Lys
                485                 490                 495

Glu His Trp Ala Lys Tyr Gly Arg Asn Phe Phe Ser Arg Tyr Asp Tyr
                500                 505                 510

Glu Glu Cys Glu Ser Glu Gly Ala Asn Lys Met Met Gln His Leu Arg
    515                 520                 525

Asp Phe Ile Ser Thr Ser Lys Pro Gly Glu Gln Tyr Gly Asn Tyr Thr
    530                 535                 540
```

```
Leu Gln Phe Ser Asp Asp Phe Ser Tyr Thr Asp Pro Val Asp Gly Ser
545                 550                 555                 560

Val Ala Ser Lys Gln Gly Leu Arg Phe Val Phe Thr Asp Gly Ser Arg
                565                 570                 575

Val Ile Tyr Arg Leu Ser Gly Thr Gly Ser Ala Gly Ala Thr Ile Arg
                580                 585                 590

Ile Tyr Val Glu Gln Phe Glu Pro Asp Val Ser Lys His Asp Val Asp
            595                 600                 605

Ala Gln Ala Ala Leu Lys Pro Leu Ile Asp Leu Ala Leu Ser Ile Ser
        610                 615                 620

Lys Leu Lys Glu Phe Thr Gly Arg Glu Lys Pro Thr Val Ile Thr
625                 630                 635

<210> SEQ ID NO 3
<211> LENGTH: 1951
<212> TYPE: DNA
<213> ORGANISM: Zea mays

<400> SEQUENCE: 3
ccacgcgtcc gcacaaactg ccctcgcggc ctcgcccgtc gccctctcg atcacttctc        60 tcccgacact ctctcactcc cgtgtcgtgt ctagcgccga cggcgttgct accggagccg      120
gccagcggcc acgatgccta caatgcacgc gcttcgccta tgcccgctgc tctccaccat      180
ccgatccaca ccaccgcggg ccactgccgc agcccgccag ggcgcgctct tcgtcgcccg      240
ctgctcctcc gccgggacgc cgtcagccgc ccaggcgctc aagatcagtt caatcccgac      300
caagccagtt gaggggcaga agactgggac tagtggcctg aggaaaaagg tgaaagtatt      360
ccagcaggag aactaccttg ctaattggat tcaggctcta ttcaattcct tgcccctga      420 agattatgtg ggtgcaaccc ttgtacttgg gggtgatggc cggtacttta caaggaggc      480 tgctcagatc atcattaaga ttgcagctgg aaatggagtt cagaagatca tagttggcag      540
gaatggtcta ctgtcaacac ctgctgtatc tgctgtaatt cgtaaaagaa agccaatgg      600 cggctttatc atgagtgcaa gccataatcc aggtggacca gacaatgact ggggtattaa      660
gtttaactac agcagtggac agccagcacc ggagacgatt actgatcaaa tttatggaaa      720
cacactatca atttctgaaa taaaaacagc agacattcct gatactgatt tgtcctctgt      780
tggagttgta agctatggtg atttcgccat agaagtgata gatcctgttt cagattacct      840
tgaactaatg gagaatgtgt tgacttcca acttatcaag gatttgcttt ctcggcctga      900
tttcaggttc atatttgatg caatgcatgc aattactggt gcgtatgccg acccatttt      960 tgttgagaaa cttggagctg atccggactg catattaaat ggggtgcctc ttgaagattt     1020
tggaaatggc catccagatc caaatctaac ttacgctaag gagcttgttt ttactatgtt     1080
tggaacccat gcacctgact tggtgcagc aagtgatggt gatggtgatc ggaacatgat     1140
tcttgggaaa aggttctta ttaccccatc agactctgtt gcaataattg cagccaatgc     1200
acagacagca attccttatt ccagtttggg tacaaaagga ctcgcgagat caatgccaac     1260
cagtggtgct cttgatcgtg ttgccgagaa attgaatgtt ccattctttg aggttccaac     1320
aggctggaaa ttttttggca acctaatgga tgcaggaaaa ttgtctattt gtggagagga     1380 aagtttttggg actggatctg atcacatcag agagaaggat ggcatctggg ctgttctggc     1440 ttggcttttcc atacttgcac accgaacaga ggataagaag gtcggagaga gattagtgtc     1500
agttgaagat attgctatgg agcactggaa aacctatgga aggaatttct tttctagata     1560
```

-continued

```
cgattatgag gcgtgtgaat cacacagtgc aaaccagatg atggatcacc ttagagatgt    1620
tatggcaaat agcaagcctg agagaaata cggaaattac accctccaat ttgctgatga     1680
tttcagctat actgatcctg tagacggtag tacggtatca aaacaaggac ttcgatttgt    1740
tttcactgat ggatctagga ttatcttccg gctttcggga accggatctg ctggagctac    1800
tatccgcctc tacatagaac aatttgaatc tgatatctcg aagcatagtc tcgatgctca    1860
aacagctttg aagcctttaa tagacctggc tttgtctgtt tcgaagctca aggacttcac    1920
aggaagagag aaacctactg tcataacata g                                    1951
```

<210> SEQ ID NO 4
<211> LENGTH: 605
<212> TYPE: PRT
<213> ORGANISM: Zea mays

<400> SEQUENCE: 4

```
Met Pro Thr Met His Ala Leu Arg Leu Cys Pro Leu Leu Ser Thr Ile
 1               5                  10                  15

Arg Ser Thr Pro Pro Arg Ala Thr Ala Ala Ala Arg Gln Gly Ala Leu
                20                  25                  30

Phe Val Ala Arg Cys Ser Ser Ala Gly Thr Pro Ser Ala Ala Gln Ala
            35                  40                  45

Leu Lys Ile Ser Ser Ile Pro Thr Lys Pro Val Glu Gly Gln Lys Thr
        50                  55                  60

Gly Thr Ser Gly Leu Arg Lys Lys Val Lys Val Phe Gln Gln Glu Asn
    65                  70                  75                  80

Tyr Leu Ala Asn Trp Ile Gln Ala Leu Phe Asn Ser Leu Pro Pro Glu
                85                  90                  95

Asp Tyr Val Gly Ala Thr Leu Val Leu Gly Gly Asp Gly Arg Tyr Phe
               100                 105                 110

Asn Lys Glu Ala Ala Gln Ile Ile Ile Lys Ile Ala Ala Gly Asn Gly
           115                 120                 125

Val Gln Lys Ile Ile Val Gly Arg Asn Gly Leu Leu Ser Thr Pro Ala
       130                 135                 140

Val Ser Ala Val Ile Arg Lys Arg Lys Ala Asn Gly Gly Phe Ile Met
145                 150                 155                 160

Ser Ala Ser His Asn Pro Gly Gly Pro Asp Asn Asp Trp Gly Ile Lys
               165                 170                 175

Phe Asn Tyr Ser Ser Gly Gln Pro Ala Pro Glu Thr Ile Thr Asp Gln
           180                 185                 190

Ile Tyr Gly Asn Thr Leu Ser Ile Ser Glu Ile Lys Thr Ala Asp Ile
       195                 200                 205

Pro Asp Thr Asp Leu Ser Ser Val Gly Val Val Ser Tyr Gly Asp Phe
   210                 215                 220

Ala Ile Glu Val Ile Asp Pro Val Ser Asp Tyr Leu Glu Leu Met Glu
225                 230                 235                 240

Asn Val Phe Asp Phe Gln Leu Ile Lys Asp Leu Leu Ser Arg Pro Asp
               245                 250                 255

Phe Arg Phe Ile Phe Asp Ala Met His Ala Ile Thr Gly Ala Tyr Ala
           260                 265                 270

Gly Pro Ile Phe Val Glu Lys Leu Gly Ala Asp Pro Asp Cys Ile Leu
       275                 280                 285

Asn Gly Val Pro Leu Glu Asp Phe Gly Asn Gly His Pro Asp Pro Asn
   290                 295                 300
```

```
Leu Thr Tyr Ala Lys Glu Leu Val Phe Thr Met Phe Gly Thr His Ala
305                 310                 315                 320

Pro Asp Phe Gly Ala Ala Ser Asp Gly Asp Gly Asp Arg Asn Met Ile
            325                 330                 335

Leu Gly Lys Arg Phe Phe Ile Thr Pro Ser Asp Ser Val Ala Ile Ile
        340                 345                 350

Ala Ala Asn Ala Gln Thr Ala Ile Pro Tyr Phe Gln Phe Gly Thr Lys
            355                 360                 365

Gly Leu Ala Arg Ser Met Pro Thr Ser Gly Ala Leu Asp Arg Val Ala
    370                 375                 380

Glu Lys Leu Asn Val Pro Phe Phe Glu Val Pro Thr Gly Trp Lys Phe
385                 390                 395                 400

Phe Gly Asn Leu Met Asp Ala Gly Lys Leu Ser Ile Cys Gly Glu Glu
            405                 410                 415

Ser Phe Gly Thr Gly Ser Asp His Ile Arg Glu Lys Asp Gly Ile Trp
        420                 425                 430

Ala Val Leu Ala Trp Leu Ser Ile Leu Ala His Arg Asn Lys Asp Lys
            435                 440                 445

Lys Val Gly Glu Arg Leu Val Ser Val Glu Asp Ile Ala Met Glu His
    450                 455                 460

Trp Lys Thr Tyr Gly Arg Asn Phe Phe Ser Arg Tyr Asp Tyr Glu Ala
465                 470                 475                 480

Cys Glu Ser His Ser Ala Asn Gln Met Met Asp His Leu Arg Asp Val
            485                 490                 495

Met Ala Asn Ser Lys Pro Gly Glu Lys Tyr Gly Asn Tyr Thr Leu Gln
        500                 505                 510

Phe Ala Asp Asp Phe Ser Tyr Thr Asp Pro Val Asp Gly Ser Thr Val
    515                 520                 525

Ser Lys Gln Gly Leu Arg Phe Val Phe Thr Asp Gly Ser Arg Ile Ile
530                 535                 540

Phe Arg Leu Ser Gly Thr Gly Ser Ala Gly Ala Thr Ile Arg Leu Tyr
545                 550                 555                 560

Ile Glu Gln Phe Glu Ser Asp Ile Ser Lys His Ser Leu Asp Ala Gln
            565                 570                 575

Thr Ala Leu Lys Pro Leu Ile Asp Leu Ala Leu Ser Val Ser Lys Leu
        580                 585                 590

Lys Asp Phe Thr Gly Arg Glu Lys Pro Thr Val Ile Thr
    595                 600                 605

<210> SEQ ID NO 5
<211> LENGTH: 573
<212> TYPE: DNA
<213> ORGANISM: Oryza sativa

<400> SEQUENCE: 5
tgatggagca tcttagagat gtgatcgcaa aaagcaagcc tggagagaaa tatggaaact      60
atacccttca gtttgccgat gatttcagtt acactgatcc ggtggatggt agcactgtat     120
ctaaacaagg gcttcgattt gtattcaccg atggatctag gattatcttc cgcctttcgg     180
gaaccggatc tgctggagca acaatccgta tatacattga gcaattcgag tctgatgcct     240
caaagcatga tctggatgca caaatagctt tgaagccttt aatagaccta gctctatctg     300
tttcaaagtt gaaggacttc actgggaaga gataagccta ctgtcataac ataaacatac     360
cggtgacatt agcaatgtta ccacctgggt attctttat tccttgtttt ttaaaagccc      420
```

| | |
|---|---|
| cttccaaccg atgaaccaat aatgttatcc taagccaagt tttgtactga gttgatggca | 480 |
| aactgtatcc tgggggtac tttcaattga acataagtat gcaaggaatg aataaagctt | 540 |
| ttaaaagcaa aaaaaaaaaa aaaaaaaaaa aaa | 573 |

<210> SEQ ID NO 6
<211> LENGTH: 117
<212> TYPE: PRT
<213> ORGANISM: Oryza sativa
<220> FEATURE:
<221> NAME/KEY: UNSURE
<222> LOCATION: (108)
<223> OTHER INFORMATION: Xaa can be any naturally occurring amino acid

<400> SEQUENCE: 6

```
Met Glu His Leu Arg Asp Val Ile Ala Lys Ser Lys Pro Gly Glu Lys
 1               5                  10                  15

Tyr Gly Asn Tyr Thr Leu Gln Phe Ala Asp Asp Phe Ser Tyr Thr Asp
             20                  25                  30

Pro Val Asp Gly Ser Thr Val Ser Lys Gln Gly Leu Arg Phe Val Phe
         35                  40                  45

Thr Asp Gly Ser Arg Ile Ile Phe Arg Leu Ser Gly Thr Gly Ser Ala
     50                  55                  60

Gly Ala Thr Ile Arg Ile Tyr Ile Glu Gln Phe Glu Ser Asp Ala Ser
 65                  70                  75                  80

Lys His Asp Leu Asp Ala Gln Ile Ala Leu Lys Pro Leu Ile Asp Leu
                 85                  90                  95

Ala Leu Ser Val Ser Lys Leu Lys Asp Phe Thr Xaa Gly Arg Asp Lys
            100                 105                 110

Pro Thr Val Ile Thr
        115
```

<210> SEQ ID NO 7
<211> LENGTH: 2204
<212> TYPE: DNA
<213> ORGANISM: Glycine max
<220> FEATURE:
<221> NAME/KEY: unsure
<222> LOCATION: (7)
<223> OTHER INFORMATION: n = A, C, G, or T
<220> FEATURE:
<221> NAME/KEY: unsure
<222> LOCATION: (1332)
<223> OTHER INFORMATION: n = A, C, G, or T

<400> SEQUENCE: 7

| | |
|---|---|
| aaaactnttt ggaaccctcc agcatttcat ttctcatcat caatggcttt ctcttgtaaa | 60 |
| cttgacagct tcattctctc tgcctataaa ccccaaaact ccattctccc actttcaatc | 120 |
| caaccttcct ccttccttcc atctccttct tctttgaagc ctcagaagct tcccttcaga | 180 |
| attcgctatg gttctaccat cagagccacg tcatcatcct caaccccttc cgcaaccatt | 240 |
| gccgaacctg aaggcattaa gattaaatcg attccaacca agcccattga tggacaaaag | 300 |
| actgaaacca gtgggcttcg aaagaaggtg aaagtgttta gcaagacaa ttaccttgca | 360 |
| aattggatcc aggctctgtt taattcattg ccaccggagg actacaagaa tggtttgttg | 420 |
| gtgttgggag gtgatggtcg atactttaat caggaagctg cacagataat aatcaaaatt | 480 |
| gctgctggaa atggtgttgg aaaaattctg gttggaaagg aagtatttt gtcaacacca | 540 |
| gccgtttctg ctgttataag aaagagaaag gcaaatggtg gatttattat gagtgcaagc | 600 |
| cataatcctg gcggacctga atatgattgg ggtattaagt ttaattacag cagtggacaa | 660 |

-continued

```
cctgcaccag aatccatcac tgacaagatt tatggaaata ccctgtcgat ctctgagata      720
aagatagctg acattcctga tgttgattta tcaaaagttg gggttacaaa ttttggaagc      780
ttcagtgtgg aagtaataga cccagtttct gactatctgg agctattgga gacagtattt      840
gattttcagc taatcagagg tcttctttca cgtccagatt ttaggtttat atttgatgcc      900
atgcatgcag ttactggtgc ttatgctaaa cccatcttcg ttgataaact cggtgctagt      960
ctggattcaa tttcaaatgg aatccctttg aagattttg gacatggcca tcctgatcct     1020
aatctaacat atgcgaagga tcttgtcgac attctgtatg ctgaaaatgg acctgatttt     1080
ggagctgcca gtgatgggga tggtgataga aatatgattt taggaagaag tttctttgta     1140
actccttcag actctgtagc agttattgca gccaatgcaa gagaagcgat tccatacttc     1200
aagaacggtg ttaagggtct tgctcgatca atgccaccaa gcggtgctct ggaccgtgtt     1260
gctaaaaaat tgaacctccc tttctttgag gtccccactg gttggaaatt ttttgggaat     1320
cttatggatg cnggaaattt gtccgtttgc ggggaagaga gttttggaac aggttctgat     1380
cacattcgtg agaaagatgg catctgggct gtcttagctt ggctttctat tattgcacat     1440
cgcaacaaag acaagaatcc cggggagaaa ttgatctccg tatctgacgt tgtgatggag     1500
cactgggcaa cttatggaag gaatttcttc tctagatatg actacgagga atgtgaatct     1560
gaaggtgcca ataagatgat agaatacctg cgagatattt tgtctaagag caagcctggt     1620
gatcagtatg gaagttatgt tctccagttt gcagatgatt ttacatacac cgatcctgta     1680
gatggaagtg tggtatcaaa acaaggtgtt cggtttgttt ttacagacgg ttcaaggatt     1740
atatatcgtt tatcaggaac tggttctgca ggggctacgg ttagagtgta cattgaacag     1800
tttgaaccaa tgtctctaa acatgatgtt gatgctcaaa ttgccttaaa accattaata     1860
gatttggcaa tatccgtgtc aaagctcaaa gacttcacag ggagggagaa gcctacagtc     1920
atcacataat ggacaattcc acaaccactt gatcaagttg ttatatgttc caaggtgtgc     1980
tctaagttga gtgcatacgc aggttgttta ttgcatgcct atccatatct gagctcgctc     2040
gagttcggtc acttttggtt gttcaagaat tttggagcga taggtcccct gtaaaatatg     2100
ctacttatat atttatgtgc aaagtatgaa gcaccgacgt gcaacaaaat aataataaaa     2160
aagaatagtt tgctgctcta aggagctagg cctttcaaaa aaaa                      2204
```

<210> SEQ ID NO 8
<211> LENGTH: 628
<212> TYPE: PRT
<213> ORGANISM: Glycine max

<400> SEQUENCE: 8

```
Met Ala Phe Ser Cys Lys Leu Asp Ser Phe Ile Leu Ser Ala Tyr Lys
  1               5                  10                  15

Pro Gln Asn Ser Ile Leu Pro Leu Ser Ile Gln Pro Ser Ser Phe Leu
                 20                  25                  30

Pro Ser Pro Ser Ser Leu Lys Pro Gln Lys Leu Pro Phe Arg Ile Arg
             35                  40                  45

Tyr Gly Ser Thr Ile Arg Ala Thr Ser Ser Ser Thr Pro Ser Ala
         50                  55                  60

Thr Ile Ala Glu Pro Glu Gly Ile Lys Ile Lys Ser Ile Pro Thr Lys
 65                  70                  75                  80

Pro Ile Asp Gly Gln Lys Thr Gly Thr Ser Gly Leu Arg Lys Lys Val
                 85                  90                  95
```

-continued

```
Lys Val Phe Met Gln Asp Asn Tyr Leu Ala Asn Trp Ile Gln Ala Leu
            100                 105                 110

Phe Asn Ser Leu Pro Pro Glu Asp Tyr Lys Asn Gly Leu Leu Val Leu
        115                 120                 125

Gly Gly Asp Gly Arg Tyr Phe Asn Gln Glu Ala Ala Gln Ile Ile Ile
    130                 135                 140

Lys Ile Ala Ala Gly Asn Gly Val Gly Lys Ile Leu Val Gly Lys Glu
145                 150                 155                 160

Gly Ile Leu Ser Thr Pro Ala Val Ser Ala Val Ile Arg Lys Arg Lys
                165                 170                 175

Ala Asn Gly Gly Phe Ile Met Ser Ala Ser His Asn Pro Gly Gly Pro
            180                 185                 190

Glu Tyr Asp Trp Gly Ile Lys Phe Asn Tyr Ser Ser Gly Gln Pro Ala
        195                 200                 205

Pro Glu Ser Ile Thr Asp Lys Ile Tyr Gly Asn Thr Leu Ser Ile Ser
    210                 215                 220

Glu Ile Lys Ile Ala Asp Ile Pro Asp Val Asp Leu Ser Lys Val Gly
225                 230                 235                 240

Val Thr Asn Phe Gly Ser Phe Ser Val Glu Val Ile Asp Pro Val Ser
                245                 250                 255

Asp Tyr Leu Glu Leu Leu Glu Thr Val Phe Asp Phe Gln Leu Ile Arg
            260                 265                 270

Gly Leu Leu Ser Arg Pro Asp Phe Arg Phe Ile Phe Asp Ala Met His
        275                 280                 285

Ala Val Thr Gly Ala Tyr Ala Lys Pro Ile Phe Val Asp Lys Leu Gly
    290                 295                 300

Ala Ser Leu Asp Ser Ile Ser Asn Gly Ile Pro Leu Glu Asp Phe Gly
305                 310                 315                 320

His Gly His Pro Asp Pro Asn Leu Thr Tyr Ala Lys Asp Leu Val Asp
                325                 330                 335

Ile Leu Tyr Ala Glu Asn Gly Pro Asp Phe Gly Ala Ala Ser Asp Gly
            340                 345                 350

Asp Gly Asp Arg Asn Met Ile Leu Gly Arg Ser Phe Phe Val Thr Pro
        355                 360                 365

Ser Asp Ser Val Ala Val Ile Ala Ala Asn Ala Arg Glu Ala Ile Pro
    370                 375                 380

Tyr Phe Lys Asn Gly Val Lys Gly Leu Ala Arg Ser Met Pro Pro Ser
385                 390                 395                 400

Gly Ala Leu Asp Arg Val Ala Lys Lys Leu Asn Leu Pro Phe Phe Glu
                405                 410                 415

Val Pro Thr Gly Trp Lys Phe Phe Gly Asn Leu Met Asp Ala Gly Asn
            420                 425                 430

Leu Ser Val Cys Gly Glu Glu Ser Phe Gly Thr Gly Ser Asp His Ile
        435                 440                 445

Arg Glu Lys Asp Gly Ile Trp Ala Val Leu Ala Trp Leu Ser Ile Ile
    450                 455                 460

Ala His Arg Asn Lys Asp Lys Asn Pro Gly Glu Lys Leu Ile Ser Val
465                 470                 475                 480

Ser Asp Val Val Met Glu His Trp Ala Thr Tyr Gly Arg Asn Phe Phe
                485                 490                 495

Ser Arg Tyr Asp Tyr Glu Glu Cys Glu Ser Glu Gly Ala Asn Lys Met
            500                 505                 510

Ile Glu Tyr Leu Arg Asp Ile Leu Ser Lys Ser Lys Pro Gly Asp Gln
```

```
                515                 520                 525
Tyr Gly Ser Tyr Val Leu Gln Phe Ala Asp Asp Phe Thr Tyr Thr Asp
        530                 535                 540
Pro Val Asp Gly Ser Val Val Ser Lys Gln Gly Val Arg Phe Val Phe
545                 550                 555                 560
Thr Asp Gly Ser Arg Ile Ile Tyr Arg Leu Ser Gly Thr Gly Ser Ala
                565                 570                 575
Gly Ala Thr Val Arg Val Tyr Ile Glu Gln Phe Glu Pro Asp Val Ser
            580                 585                 590
Lys His Asp Val Asp Ala Gln Ile Ala Leu Lys Pro Leu Ile Asp Leu
        595                 600                 605
Ala Ile Ser Val Ser Lys Leu Lys Asp Phe Thr Gly Arg Glu Lys Pro
    610                 615                 620
Thr Val Ile Thr
625

<210> SEQ ID NO 9
<211> LENGTH: 2197
<212> TYPE: DNA
<213> ORGANISM: Oryza sativa

<400> SEQUENCE: 9
gcacgaggct tgcccgcttc cttccgcggt gcaagcgcaa caccacctca cctcactccc      60
cttctcgcct cttctcccct tctccacctc ctcttctctc cgcgtggcgg tggcattgcc     120
ggccgccgca tcgtctcggg atggcctcgc acgcgctccg cctccacccg ctgctcttct     180
ccgccgccgc cgcgcgcccg gctccgctcg cggcgcggcc cggtggtggt gcccgccggg     240
tccaccgccg ccactctctc gccgtcgtcc ggtgctcctc ctccgccgcc caggcgctca     300
agatcaagtc gattccgacc aagcccgttg aggggcagaa gaccgggacc agtgggttga     360
ggaagaaggt gaaagtgttc cagcaggaga attacctcgc taattggatt caggctctgt     420
tcaattcatt gccccggag gattatgttg gtggaaccct tgtgcttggt ggtgatggcc      480
gatactttaa caaggatgct gctcagatta tcactaaaat tgcagctggg aatggtgttg     540
ggaagatcct agttggcagg aacggtctgc tgtcaacgcc tgctgtatct gcagtaattc     600
gtaaaagaca agccaatggt ggcttcatca tgagtgcaag ccataatcca ggtgggccag     660
ataatgattg gggtatcaag ttcaactata gcagtgggca gccagcacca gagacaatta     720
ccgaccaaat atatggaaac acactttcga tttctgaaat aaaaacggca gatattcctg     780
atgttgattt gtcctctcta ggagttgtaa gctatggtga tttcaccgtt gaagtgatag     840
accctgtctt ggactacctt gagctaatgg agaatgtgtt tgacttccaa cttatcaagg     900
gcttgttgtc tcggccagat ttcaggtttg tatttgatgc catgcatgct gtgactggtg     960
catatgcgga tcctatttt gttgagaaac ttggagctga tccggactat atattaaatg    1020
gtgttccact tgaagatttt ggcaatggtc accctgatcc taatttaact tatgccaaag    1080
agcttgtgtt taccatgttt ggaagcggag cacctgactt tggtgcagca agtgatggtg    1140
atggtgatcg aaacatgatt cttggaagaa ggttctttgt tacaccatca gactctgttg    1200
caataattgc agcgaatgca caggcagcaa ttccttattt ccaatctggt ccaaaaggtc    1260
ttgctagatc aatgccaacg agtggtgctc ttgatcgtgt agctgataaa ttgaatgttc    1320
cgttctttga ggtaccaaca ggatggaaat tttttggaaa cctaatggat gcaggtaaat    1380
tgtctatatg tggagaggaa agttttggga caggatctga tcacatcagg gagaaggatg    1440
```

-continued

```
gcatatgggc tgttctagct tggctgtcca tacttgcaca ccggaacaag gataagaagg      1500
ccggggagag attagtgtca gtggaagatg tagctaggga cactgggca acctatggaa       1560 ggaatttctt ctccagatat gattatgagg agtgtgaatc tgagagtgca ataagatga       1620 tggagcatct tagagatgtg atcgcaaaaa gcaagcctgg agagaaatat ggaaactata      1680
cccttcagtt tgccgatgat ttcagttaca ctgatccggt ggatggtagc actgtatcta      1740
aacaagggct tcgatttgta ttcaccgatg gatctaggat tatcttccgc ctttcgggaa      1800
ccggatctgc tggagcaaca atccgtatat acattgagca attcgagtct gatgcctcaa      1860
agcatgatct ggatgcacaa atagctttga agcctttaat agacctagct ctatctgttt      1920
caaagttgaa ggacttcact ggaagagata agcctactgt cataacataa acataccggt      1980
gacattagca atgttaccac ctgtgtattc ttttatttct ttgttttat agccccttcc       2040 aaccgatgaa ccaataatgt aatcttaggc caagttttgt actgagttga tggcaaactg      2100
tatcttggag gtacctttca ttgaacatag tatgcaggaa tgaataagct tttagagcaa      2160
tggtacatat ttcagaacaa aaaaaaaaaa aaaaaaa                               2197
```

```
<210> SEQ ID NO 10
<211> LENGTH: 655
<212> TYPE: PRT
<213> ORGANISM: Oryza sativa

<400> SEQUENCE: 10
```

```
Thr Arg Leu Ala Arg Phe Leu Pro Arg Cys Lys Arg Asn Thr Thr Ser
 1               5                  10                  15

Pro His Ser Pro Ser Arg Leu Phe Ser Pro Ser Pro Pro Leu Leu
            20                  25                  30

Ser Ala Trp Arg Trp His Cys Arg Pro Pro His Arg Leu Gly Met Ala
        35                  40                  45

Ser His Ala Leu Arg Leu His Pro Leu Leu Phe Ser Ala Ala Ala Ala
    50                  55                  60

Arg Pro Ala Pro Leu Ala Ala Arg Pro Gly Gly Ala Arg Arg Val
65                  70                  75                  80

His Arg Arg His Ser Leu Ala Val Val Arg Cys Ser Ser Ala Ala
                85                  90                  95

Gln Ala Leu Lys Ile Lys Ser Ile Pro Thr Lys Pro Val Glu Gly Gln
            100                 105                 110

Lys Thr Gly Thr Ser Gly Leu Arg Lys Lys Val Lys Val Phe Gln Gln
        115                 120                 125

Glu Asn Tyr Leu Ala Asn Trp Ile Gln Ala Leu Phe Asn Ser Leu Pro
    130                 135                 140

Pro Glu Asp Tyr Val Gly Gly Thr Leu Val Leu Gly Gly Asp Gly Arg
145                 150                 155                 160

Tyr Phe Asn Lys Asp Ala Ala Gln Ile Ile Thr Lys Ile Ala Ala Gly
                165                 170                 175

Asn Gly Val Gly Lys Ile Leu Val Gly Arg Asn Gly Leu Leu Ser Thr
            180                 185                 190

Pro Ala Val Ser Ala Val Ile Arg Lys Arg Gln Ala Asn Gly Gly Phe
        195                 200                 205

Ile Met Ser Ala Ser His Asn Pro Gly Gly Pro Asp Asn Asp Trp Gly
    210                 215                 220

Ile Lys Phe Asn Tyr Ser Ser Gly Gln Pro Ala Pro Glu Thr Ile Thr
225                 230                 235                 240
```

-continued

```
Asp Gln Ile Tyr Gly Asn Thr Leu Ser Ile Ser Glu Ile Lys Thr Ala
                245                 250                 255
Asp Ile Pro Asp Val Asp Leu Ser Ser Leu Gly Val Val Ser Tyr Gly
            260                 265                 270
Asp Phe Thr Val Glu Val Ile Asp Pro Val Leu Asp Tyr Leu Glu Leu
        275                 280                 285
Met Glu Asn Val Phe Asp Phe Gln Leu Ile Lys Gly Leu Leu Ser Arg
290                 295                 300
Pro Asp Phe Arg Phe Val Phe Asp Ala Met His Ala Val Thr Gly Ala
305                 310                 315                 320
Tyr Ala Asp Pro Ile Phe Val Glu Lys Leu Gly Ala Asp Pro Asp Tyr
                325                 330                 335
Ile Leu Asn Gly Val Pro Leu Glu Asp Phe Gly Asn Gly His Pro Asp
            340                 345                 350
Pro Asn Leu Thr Tyr Ala Lys Glu Leu Val Phe Thr Met Phe Gly Ser
        355                 360                 365
Gly Ala Pro Asp Phe Gly Ala Ala Ser Asp Gly Asp Gly Asp Arg Asn
370                 375                 380
Met Ile Leu Gly Arg Arg Phe Val Thr Pro Ser Asp Ser Val Ala
385                 390                 395                 400
Ile Ile Ala Ala Asn Ala Gln Ala Ala Ile Pro Tyr Phe Gln Ser Gly
                405                 410                 415
Pro Lys Gly Leu Ala Arg Ser Met Pro Thr Ser Gly Ala Leu Asp Arg
            420                 425                 430
Val Ala Asp Lys Leu Asn Val Pro Phe Phe Glu Val Pro Thr Gly Trp
        435                 440                 445
Lys Phe Phe Gly Asn Leu Met Asp Ala Gly Lys Leu Ser Ile Cys Gly
450                 455                 460
Glu Glu Ser Phe Gly Thr Gly Ser Asp His Ile Arg Glu Lys Asp Gly
465                 470                 475                 480
Ile Trp Ala Val Leu Ala Trp Leu Ser Ile Leu Ala His Arg Asn Lys
                485                 490                 495
Asp Lys Lys Ala Gly Glu Arg Leu Val Ser Val Glu Asp Val Ala Arg
            500                 505                 510
Glu His Trp Ala Thr Tyr Gly Arg Asn Phe Phe Ser Arg Tyr Asp Tyr
        515                 520                 525
Glu Glu Cys Glu Ser Glu Ser Ala Asn Lys Met Met Glu His Leu Arg
530                 535                 540
Asp Val Ile Ala Lys Ser Lys Pro Gly Glu Lys Tyr Gly Asn Tyr Thr
545                 550                 555                 560
Leu Gln Phe Ala Asp Asp Phe Ser Tyr Thr Asp Pro Val Asp Gly Ser
                565                 570                 575
Thr Val Ser Lys Gln Gly Leu Arg Phe Val Phe Thr Asp Gly Ser Arg
            580                 585                 590
Ile Ile Phe Arg Leu Ser Gly Thr Gly Ser Ala Gly Ala Thr Ile Arg
        595                 600                 605
Ile Tyr Ile Glu Gln Phe Glu Ser Asp Ala Ser Lys His Asp Leu Asp
610                 615                 620
Ala Gln Ile Ala Leu Lys Pro Leu Ile Asp Leu Ala Leu Ser Val Ser
625                 630                 635                 640
Lys Leu Lys Asp Phe Thr Gly Arg Asp Lys Pro Thr Val Ile Thr
                645                 650                 655
```

<210> SEQ ID NO 11
<211> LENGTH: 629
<212> TYPE: PRT
<213> ORGANISM: Brassica napus

<400> SEQUENCE: 11

```
Met Ser Ser Thr Tyr Ala Arg Phe Asp Thr Val Phe Leu Leu Ser Arg
  1               5                  10                  15

Phe Ala Gly Ala Lys Tyr Ser Pro Leu Trp Pro Ser Ser Ser Ser Ser
             20                  25                  30

Ser His Ser Ser Leu Leu Ser Ser Gly Ile His Leu Arg Ala Lys Pro
         35                  40                  45

Asn Ser Arg Leu Arg Ser Val Thr Gly Ala Ser Ser Ser Ser Ser Gly
     50                  55                  60

Pro Ile Ile Ala Gly Ser Glu Ser Ile Glu Ile Lys Ser Leu Pro Thr
 65                  70                  75                  80

Lys Pro Ile Glu Gly Gln Lys Thr Gly Thr Ser Gly Leu Arg Lys Lys
                 85                  90                  95

Val Lys Val Phe Met Gln Asp Asn Tyr Leu Ala Asn Trp Ile Gln Ala
            100                 105                 110

Leu Phe Asn Ser Leu Pro Leu Glu Asp Tyr Lys Asp Ala Thr Leu Val
        115                 120                 125

Leu Gly Gly Asp Gly Arg Tyr Phe Asn Lys Glu Ala Ser Gln Ile Ile
    130                 135                 140

Ile Lys Ile Ala Ala Gly Asn Gly Val Gly Lys Ile Leu Val Gly Gln
145                 150                 155                 160

Glu Gly Ile Leu Ser Thr Pro Ala Val Ser Ala Val Ile Arg Lys Arg
                165                 170                 175

Lys Ala Asn Gly Gly Phe Ile Met Ser Ala Ser His Asn Pro Gly Gly
            180                 185                 190

Pro Glu Tyr Asp Trp Gly Ile Lys Phe Asn Tyr Ser Ser Gly Gln Pro
        195                 200                 205

Ala Pro Glu Ser Ile Thr Asp Lys Ile Tyr Gly Asn Thr Leu Ser Ile
    210                 215                 220

Ser Glu Ile Lys Val Ala Glu Ile Pro Asp Ile Asp Leu Ser His Val
225                 230                 235                 240

Gly Val Thr Lys Tyr Gly Asn Phe Ser Val Glu Val Ile Asp Pro Ile
                245                 250                 255

Ser Asp Tyr Leu Glu Leu Met Glu Asp Val Phe Asp Phe Asp Leu Ile
            260                 265                 270

Arg Gly Leu Leu Ser Arg Ser Asp Phe Gly Phe Met Phe Asp Ala Met
        275                 280                 285

His Ala Val Thr Gly Ala Tyr Ala Lys Pro Ile Phe Val Asp Asn Leu
    290                 295                 300

Glu Ala Lys Pro Asp Ser Ile Ser Asn Gly Val Pro Leu Glu Asp Phe
305                 310                 315                 320

Gly His Gly His Pro Asp Pro Asn Leu Thr Tyr Ala Lys Asp Leu Val
                325                 330                 335

Asp Val Met Tyr Arg Asp Asp Gly Pro Asp Phe Gly Ala Ala Ser Asp
            340                 345                 350

Gly Asp Gly Asp Arg Asn Met Val Leu Gly Asn Lys Phe Phe Val Thr
        355                 360                 365

Pro Ser Asp Ser Val Ala Ile Ile Ala Ala Asn Ala Gln Glu Ala Ile
    370                 375                 380
```

```
Pro Tyr Phe Arg Ala Gly Pro Lys Gly Leu Ala Arg Ser Met Pro Thr
385                 390                 395                 400

Ser Gly Ala Leu Asp Arg Val Ala Glu Lys Leu Lys Leu Pro Phe Phe
            405                 410                 415

Glu Val Pro Thr Gly Trp Lys Phe Phe Gly Asn Leu Met Asp Ala Gly
        420                 425                 430

Lys Leu Ser Ile Cys Gly Glu Glu Ser Phe Gly Thr Gly Ser Asp His
    435                 440                 445

Ile Arg Glu Lys Asp Gly Ile Trp Ala Val Leu Ala Trp Leu Ser Ile
450                 455                 460

Leu Ala His Arg Ile Lys Asp Lys Lys Pro Gly Glu Lys Leu Val Ser
465                 470                 475                 480

Val Ala Asp Val Val Asn Glu Tyr Trp Ala Thr Tyr Gly Arg Asn Phe
                485                 490                 495

Phe Ser Arg Tyr Asp Tyr Glu Glu Cys Glu Ser Glu Gly Ala Asn Lys
            500                 505                 510

Met Ile Glu Tyr Leu Arg Asp Ile Val Ala Lys Ser Lys Ala Gly Glu
        515                 520                 525

Asn Tyr Gly Asn Tyr Val Leu Gln Phe Ala Asp Asp Phe Ser Tyr Lys
    530                 535                 540

Asp Pro Val Asp Gly Ser Val Ala Ser Lys Gln Gly Val Arg Phe Val
545                 550                 555                 560

Phe Thr Asp Gly Ser Arg Ile Ile Tyr Arg Leu Ser Gly Asn Gly Ser
                565                 570                 575

Ala Gly Ala Thr Val Arg Ile Tyr Ile Glu Gln Phe Glu Pro Asp Val
            580                 585                 590

Ser Lys His Asp Val Asp Ala Gln Ile Ala Ile Lys Pro Leu Ile Asp
        595                 600                 605

Leu Ala Leu Ser Val Ser Lys Leu Lys Glu Phe Thr Gly Arg Glu Lys
    610                 615                 620

Pro Thr Val Ile Thr
625

<210> SEQ ID NO 12
<211> LENGTH: 626
<212> TYPE: PRT
<213> ORGANISM: Pisum sativum

<400> SEQUENCE: 12

Met Ala Phe Cys Tyr Arg Leu Asp Asn Phe Ile Ile Ser Ala Phe Lys
1               5                   10                  15

Pro Lys His Ser Asn Val Pro Leu Ser Ile His His Ser Ser Ser Asn
            20                  25                  30

Phe Pro Ser Phe Lys Val Gln Asn Phe Pro Phe Arg Val Arg Tyr Asn
        35                  40                  45

Ser Ala Ile Arg Ala Thr Ser Ser Ser Ser Thr Pro Thr Thr Ile
    50                  55                  60

Ala Glu Pro Asn Asp Ile Lys Ile Asn Ser Ile Pro Thr Lys Pro Ile
65                  70                  75                  80

Glu Gly Gln Lys Thr Gly Thr Ser Gly Leu Arg Lys Lys Val Lys Val
                85                  90                  95

Phe Lys Gln Glu Asn Tyr Leu Ala Asn Trp Ile Gln Ala Leu Phe Asn
            100                 105                 110

Ser Leu Pro Pro Glu Asp Tyr Lys Asn Gly Leu Leu Val Leu Gly Gly
        115                 120                 125
```

```
Asp Gly Arg Tyr Phe Asn Lys Glu Ala Ala Gln Ile Ile Lys Ile
    130                 135                 140

Ala Ala Gly Asn Gly Val Gly Lys Ile Leu Val Gly Lys Glu Gly Ile
145                 150                 155                 160

Leu Ser Thr Pro Ala Val Ser Ala Val Ile Arg Lys Arg Glu Ala Asn
                165                 170                 175

Gly Gly Phe Ile Met Ser Ala Ser His Asn Pro Gly Gly Pro Glu Tyr
                180                 185                 190

Asp Trp Gly Ile Lys Phe Asn Tyr Ser Ser Gly Gln Pro Ala Pro Glu
            195                 200                 205

Ser Ile Thr Asp Lys Ile Tyr Gly Asn Thr Leu Ser Ile Ser Glu Ile
        210                 215                 220

Lys Ile Ala Asp Ile Pro Asp Val Asp Leu Ser Asn Val Gly Val Thr
225                 230                 235                 240

Lys Phe Gly Ser Phe Ser Val Glu Val Ile Asp Pro Val Ser Asp Tyr
                245                 250                 255

Leu Glu Leu Leu Glu Thr Val Phe Asp Phe Gln Leu Ile Lys Ser Leu
                260                 265                 270

Ile Ser Arg Pro Asp Phe Arg Phe Thr Phe Asp Ala Met His Ala Val
            275                 280                 285

Ala Gly Ala Tyr Ala Thr Pro Ile Phe Val Asp Lys Leu Ser Ala Ser
290                 295                 300

Leu Asp Ser Ile Ser Asn Gly Ile Pro Leu Glu Asp Phe Gly His Gly
305                 310                 315                 320

His Pro Asp Pro Asn Leu Thr Tyr Ala Lys Asp Leu Val Lys Ile Met
                325                 330                 335

Tyr Ala Glu Asn Gly Pro Asp Phe Gly Ala Ala Ser Asp Gly Asp Gly
                340                 345                 350

Asp Arg Asn Met Ile Leu Gly Thr Ser Phe Phe Val Thr Pro Ser Asp
            355                 360                 365

Ser Val Ala Val Ile Ala Ala Asn Ala Lys Glu Ala Ile Pro Tyr Phe
370                 375                 380

Lys Asp Ser Ile Lys Gly Leu Ala Arg Ser Met Pro Thr Ser Gly Ala
385                 390                 395                 400

Leu Asp Arg Val Ala Glu Lys Leu Asn Leu Pro Phe Phe Glu Val Pro
                405                 410                 415

Thr Gly Trp Lys Phe Phe Gly Asn Leu Met Asp Ala Gly Asn Leu Ser
            420                 425                 430

Ile Cys Gly Glu Glu Ser Phe Gly Thr Gly Ser Asp His Ile Arg Glu
        435                 440                 445

Lys Asp Gly Ile Trp Ala Val Leu Ala Trp Leu Ser Ile Ile Ala His
450                 455                 460

Arg Asn Lys Asp Thr Lys Pro Gly Glu Lys Leu Val Ser Val Ser Asp
465                 470                 475                 480

Val Val Lys Glu His Trp Ala Thr Tyr Gly Arg Asn Phe Phe Ser Arg
                485                 490                 495

Tyr Asp Tyr Glu Glu Cys Glu Ser Glu Gly Ala Asn Lys Met Ile Glu
            500                 505                 510

Tyr Leu Arg Glu Leu Leu Ser Lys Ser Lys Pro Gly Asp Lys Tyr Gly
        515                 520                 525

Ser Tyr Val Leu Gln Phe Ala Asp Asp Phe Thr Tyr Thr Asp Pro Val
530                 535                 540
```

```
Asp Gly Ser Val Val Ser Lys Gln Gly Val Arg Phe Val Phe Thr Asp
545                 550                 555                 560

Gly Ser Arg Ile Ile Tyr Arg Leu Ser Gly Thr Ser Ala Gly Ala
            565                 570                 575

Thr Val Arg Val Tyr Ile Glu Gln Phe Glu Pro Asp Val Ser Lys His
            580                 585                 590

Asp Val Asp Ala Gln Ile Ala Leu Lys Pro Leu Ile Asp Leu Ala Leu
            595                 600                 605

Ser Val Ser Lys Leu Lys Asp Phe Thr Gly Arg Glu Lys Pro Thr Val
            610                 615                 620

Ile Thr
625

<210> SEQ ID NO 13
<211> LENGTH: 626
<212> TYPE: PRT
<213> ORGANISM: Pisum sativum

<400> SEQUENCE: 13

Met Ala Phe Cys Tyr Arg Leu Asp Asn Phe Ile Ile Ser Ala Phe Lys
1               5                   10                  15

Pro Lys His Ser Asn Val Pro Leu Ser Ile His His Ser Ser Ser Asn
            20                  25                  30

Phe Pro Ser Phe Lys Val Gln Asn Phe Pro Phe Arg Val Arg Tyr Asn
        35                  40                  45

Ser Ala Ile Arg Ala Thr Ser Ser Ser Ser Thr Pro Thr Thr Ile
    50                  55                  60

Ala Glu Pro Asn Asp Ile Lys Ile Asn Ser Ile Pro Thr Lys Pro Ile
65                  70                  75                  80

Glu Gly Gln Lys Thr Gly Thr Ser Gly Leu Arg Lys Val Lys Val
            85                  90                  95

Phe Lys Gln Glu Asn Tyr Leu Ala Asn Trp Ile Gln Ala Leu Phe Asn
                100                 105                 110

Ser Leu Pro Pro Glu Asp Tyr Lys Asn Gly Leu Leu Val Leu Gly Gly
            115                 120                 125

Asp Gly Arg Tyr Phe Asn Lys Glu Ala Ala Gln Ile Ile Ile Lys Ile
    130                 135                 140

Ala Ala Gly Asn Gly Val Gly Lys Ile Leu Val Gly Lys Glu Gly Ile
145                 150                 155                 160

Leu Ser Thr Pro Ala Val Ser Ala Val Ile Arg Lys Arg Glu Ala Asn
                165                 170                 175

Gly Gly Phe Ile Met Ser Ala Ser His Asn Pro Gly Gly Pro Glu Tyr
            180                 185                 190

Asp Trp Gly Ile Lys Phe Asn Tyr Ser Ser Gly Gln Pro Ala Pro Glu
        195                 200                 205

Ser Ile Thr Asp Lys Ile Tyr Gly Asn Thr Leu Ser Ile Ser Glu Ile
    210                 215                 220

Lys Ile Ala Asp Ile Pro Asp Val Asp Leu Ser Asn Val Gly Val Thr
225                 230                 235                 240

Lys Phe Gly Ser Phe Ser Val Glu Val Ile Asp Pro Val Ser Asp Tyr
                245                 250                 255

Leu Glu Leu Leu Glu Thr Val Phe Asp Phe Gln Leu Ile Lys Ser Leu
            260                 265                 270

Ile Ser Arg Pro Asp Phe Arg Phe Thr Phe Asp Ala Met His Ala Val
        275                 280                 285
```

-continued

Ala Gly Ala Tyr Ala Thr Pro Ile Phe Val Asp Lys Leu Gly Ala Ser
    290                 295                 300

Pro Asp Ser Ile Ser Asn Gly Ile Pro Leu Glu Asp Phe Gly His Gly
305                 310                 315                 320

His Pro Asp Pro Asn Leu Thr Tyr Ala Lys Asp Leu Val Asn Ile Met
                325                 330                 335

Tyr Ala Glu Asn Gly Pro Asp Phe Gly Ala Ala Ser Asp Gly Asp Gly
            340                 345                 350

Asp Arg Asn Met Ile Leu Gly Thr Ser Phe Phe Val Thr Pro Ser Asp
        355                 360                 365

Ser Val Ala Val Ile Ala Ala Asn Ala Lys Glu Ala Ile Pro Tyr Phe
    370                 375                 380

Lys Asp Ser Ile Lys Gly Leu Ala Arg Ser Met Pro Thr Ser Gly Ala
385                 390                 395                 400

Leu Asp Arg Val Ala Glu Lys Leu Asn Leu Pro Phe Phe Glu Val Pro
                405                 410                 415

Thr Gly Trp Lys Phe Phe Gly Asn Leu Met Asp Ala Gly Asn Leu Ser
            420                 425                 430

Ile Cys Gly Glu Glu Ser Phe Gly Thr Gly Ser Asp His Ile Arg Glu
        435                 440                 445

Lys Asp Gly Ile Trp Ala Val Leu Ala Trp Leu Ser Ile Ile Ala His
    450                 455                 460

Arg Asn Lys Asp Thr Lys Pro Gly Glu Lys Leu Val Ser Val Ser Asp
465                 470                 475                 480

Val Val Lys Glu His Trp Ala Thr Tyr Gly Arg Asn Phe Phe Ser Arg
                485                 490                 495

Tyr Asp Tyr Glu Glu Cys Glu Ser Glu Gly Ala Asn Lys Met Ile Glu
            500                 505                 510

Tyr Leu Arg Glu Leu Leu Ser Lys Ser Lys Pro Gly Asp Lys Tyr Gly
        515                 520                 525

Ser Tyr Val Leu Gln Phe Ala Asp Asp Tyr Thr Tyr Thr Asp Pro Val
    530                 535                 540

Asp Gly Ser Val Val Ser Lys Gln Gly Val Arg Phe Val Phe Thr Asp
545                 550                 555                 560

Gly Ser Arg Ile Ile Tyr Arg Leu Ser Gly Thr Gly Ser Ala Gly Ala
                565                 570                 575

Thr Val Arg Val Tyr Ile Glu Gln Phe Glu Pro Asp Val Ser Lys His
            580                 585                 590

Asp Val Asp Ala Gln Ile Ala Leu Lys Pro Leu Ile Asp Leu Ala Leu
        595                 600                 605

Ser Val Ser Lys Leu Lys Asp Phe Thr Gly Arg Glu Lys Pro Thr Val
    610                 615                 620

Ile Thr
625

<210> SEQ ID NO 14
<211> LENGTH: 574
<212> TYPE: DNA
<213> ORGANISM: synthetic construct

<400> SEQUENCE: 14
ggccgctgag ctgatttaag atttatcaaa agttggggtt acaaattttg gaagcttcag    60
tgtggaagta atagacccag tttctgacta tctggagcta ttggagacag tatttgattt   120

```
tcagctaatc agaggtcttc tttcacgtcc agattttagg tttatatttg atgccatgca    180
tgcagttact ggtgcttatg ctaaacccat cttcgttgat aaactcggtg ctagtctgga    240
ttcaatttca aatggaatcc ctttggaaga ttttggacat ggccatcctg atcctaatct    300
aacatatgcg aaggatcttg tcgacattct gtatgctgaa aatggacctg attttggagc    360
tgccagtgat ggggatggtg atagaaatat gatttttagga agaagtttct ttgtaactcc    420
ttcagactct gtagcagtta ttgcagccaa tgcaagagag gcgattccat acttcaagaa    480
cggtgttaag ggtcttgctc gatcaatgcc aacaagcggt gctctggacc gtgctgctaa    540
aaaattgaac ctcccttctct gagctgattt aagc                               574

<210> SEQ ID NO 15
<211> LENGTH: 541
<212> TYPE: DNA
<213> ORGANISM: Glycine max

<400> SEQUENCE: 15
gatttatcaa agttggggt tacaaatttt ggaagcttca gtgtggaagt aatagaccca     60
gtttctgact atctggagct attggagaca gtatttgatt ttcagctaat cagaggtctt    120 cttttcacgtc cagattttag gtttatattt gatgccatgc atgcagttac tggtgcttat    180
gctaaaccca tcttcgttga taaactcggt gctagtctgg attcaatttc aaatggaatc    240
cctttggaag attttggaca tggccatcct gatcctaatc taacatatgc gaaggatctt    300
gtcgacattc tgtatgctga aaatggacct gattttggag ctgccagtga tggggatggt    360
gatagaaata tgatttttagg aagaagtttc tttgtaactc cttcagactc tgtagcagtt    420
attgcagcca atgcaagaga agcgattcca tacttcaaga acggtgttaa gggtcttgct    480
cgatcaatgc caacaagcgg tgctctggac cgtgctgcta aaaaattgaa cctcccttcc    540
t                                                                   541

<210> SEQ ID NO 16
<211> LENGTH: 2401
<212> TYPE: DNA
<213> ORGANISM: Zea mays

<400> SEQUENCE: 16
ccacgcgtcc gcacaaactg ccctcgcggc ctcgcccgtc gcccctctcg atcacttctc     60
tcccgacact ctctcactcc cgtgtcgtgt ctagcgccga cggcgttgct accggagccg    120
gccagcggcc acgatgccta caatgcacgc gcttcgccta tgcccgctgc tctccaccat    180
ccgatccaca ccaccgcggg ccactgccgc agcccgccag ggcgcgctct tcgtcgcccg    240
ctgctcctcc gccgggacgc cgtcagccgc ccaggcgctc aagatcagtt caatcccgac    300
caagccagtt gaggggcaga agactgggac tagtggcctg aggaaaaagg tgaaagtatt    360
ccagcaggag aactaccttg ctaattggat tcaggctcta ttcaattcct gcccccctga    420
agattatgtg ggtgcaaccc ttgtacttgg gggtgatggc cggtacttta caaggaggc     480 tgctcagatc atcattaaga ttgcagctgg aaatggagtt cagaagatca tagttggcag    540
gaatggtcta ctgtcaacac ctgctgtatc tgctgtaatt cgtaaaagaa agccaatgg     600 cggctttatc atgagtgcaa gccataatcc aggtggacca gacaatgact ggggtattaa    660
gtttaactac agcagtggac agccagcacc ggagacgatt actgatcaaa tttatggaaa    720
cacactatca atttctgaaa taaaaacagc agacattcct gatactgatt tgtcctctgt    780
tggagttgta agctatggtg atttcgccat agaagtgata gatcctgttt cagattacct    840
```

-continued

```
tgaactaatg agaatgtgt ttgacttcca acttatcaag gatttgcttt ctcggcctga      900
tttcaggttc atatttgatg caatgcatgc aattactggt gcgtatgccg gacccatttt      960
tgttgagaaa cttggagctg atccggactg catattaaat ggggtgcctc ttgaagattt     1020
tggaaatggc catccagatc caaatctaac ttacgctaag gagcttgttt ttactatgtt     1080
tggaacccat gcacctgact tggtgcagc aagtgatggt gatggtgatc ggaacatgat      1140
tcttgggaaa aggttctta ttaccccatc agactctgtt gcaataattg cagccaatgc      1200
acagacagca attccttatt ccagtttggg tacaaaagga ctcgcgagat caatgccaac     1260
cagtggtgct cttgatcgtg ttgccgagaa attgaatgtt ccattctttg aggttccaac     1320
aggctggaaa tttttggca acctaatgga tgcaggaaaa ttgtctattt gtggagagga     1380
aagttttggg actggatctg atcacatcag agagaaggat ggcatctggg ctgttctggc     1440
ttggctttcc atacttgcac accgaacaa ggataagaag gtcggagaga gattagtgtc      1500
agttgaagat attgctatgg agcactggaa aacctatggc aggaatttct tttctagata     1560
cgattatgag gcgtgtgaat cacacagtgc aaaccagatg atggatcacc ttagagatgt     1620
tatggcaaat agcaagcctg agagaaata cggaaattac accctccaat ttgctgatga      1680
tttcagctat actgatcctg tagacggtag tacggtatca aaacaaggac ttcgatttgt     1740
tttcactgat ggatctagga ttatcttccg gctttcggga accggatctg ctggagctac     1800
tatccgcctc tacatagaac aatttgaatc tgatatctcg aagcatagtc tcgatgctca     1860
aacagctttg aagccttaa tagacctggc tttgtctgtt tcgaagctca aggacttcac      1920
aggaagagag aaacctactg tcataacata ggccctgttt gtttcggctt ttggcagctt     1980
ctggccacca aaagctactg cgtactgtca acgctcagc ttttcagcca gcttctataa      2040
aattcgttgg gggcaaaaac catctaaaat caaataaaca cataatcggt tgagtcgttg     2100
taatagtagg aattcatcac tttctagatc ctgagcctta tgaacaactt tatcttccta     2160
cacacataat cgtaatgata ctcagattct cccacagcca gattctcccc acagccagat     2220
tttcagaaaa gttggtcaga aaaaagctga accaaacagc cccataatat ttagatgttg     2280
ttgtcctcgg ccataccaac tgagcagcat gggccaagaa ttgaactgat ggaaaatatg     2340
tatcattagg acaaattccg ccagaataag ttgttcctcg gaaaaaaaaa aaaaaaaaa     2400 g                                                                      2401
```

<210> SEQ ID NO 17
<211> LENGTH: 4974
<212> TYPE: DNA
<213> ORGANISM: synthetic construct
<220> FEATURE:
<221> NAME/KEY: unsure
<222> LOCATION: (3951)
<223> OTHER INFORMATION: n = A, C, G, or T

<400> SEQUENCE: 17

```
ggccgccgac tcgacgatga gcagatgac cagctccggc cgcgacacaa gtgtgagagt        60
actaaataaa tgctttggtt gtacgaaatc attacactaa ataaataat caaagcttat       120 atatgccttc cgctaaggcc gaatgcaaag aaattggttc tttctcgtta tcttttgcca      180
cttttactag tacgtattaa ttactactta atcatctttg tttacggctc attatatccg      240
tcgacggcgc gcccgatcat ccggatatag ttcctccttt cagcaaaaaa ccctcaaga      300 cccgtttaga ggccccaagg ggttatgcta gttattgctc agcggtggca gcagccaact     360
```

-continued

```
cagcttcctt tcgggctttg ttagcagccg gatcgatcca agctgtacct cactattcct    420
ttgccctcgg acgagtgctg gggcgtcggt ttccactatc ggcgagtact tctacacagc    480
catcggtcca gacggccgcg cttctgcggg cgatttgtgt acgcccgaca gtcccggctc    540
cggatcggac gattgcgtcg catcgaccct gcgcccaagc tgcatcatcg aaattgccgt    600
caaccaagct ctgatagagt tggtcaagac caatgcggag catatacgcc cggagccgcg    660
gcgatcctgc aagctccgga tgcctccgct cgaagtagcg cgtctgctgc tccatacaag    720
ccaaccacgg cctccagaag aagatgttgg cgacctcgta ttgggaatcc ccgaacatcg    780
cctcgctcca gtcaatgacc gctgttatgc ggccattgtc cgtcaggaca ttgttggagc    840
cgaaatccgc gtgcacgagg tgccggactt cggggcagtc ctcggcccaa agcatcagct    900
catcgagagc ctgcgcgacg gacgcactga cggtgtcgtc catcacagtt tgccagtgat    960
acacatgggg atcagcaatc gcgcatatga aatcacgcca tgtagtgtat tgaccgattc   1020
cttgcggtcc gaatgggccg aacccgctcg tctggctaag atcggccgca gcgatcgcat   1080
ccatagcctc cgcgaccggc tgcagaacag cgggcagttc ggtttcaggc aggtcttgca   1140
acgtgacacc ctgtgcacgg cgggagatgc aataggtcag gctctcgctg aattccccaa   1200
tgtcaagcac ttccggaatc gggagcgcgg ccgatgcaaa gtgccgataa acataacgat   1260
ctttgtagaa accatcggcg cagctattta cccgcaggac atatccacgc cctcctacat   1320
cgaagctgaa agcacgagat tcttcgccct ccgagagctg catcaggtcg gagacgctgt   1380
cgaacttttc gatcagaaac ttctcgacag acgtcgcggt gagttcaggc ttttccatgg   1440
gtatatctcc ttcttaaagt taaacaaaat tatttctaga gggaaaccgt tgtggtctcc   1500
ctatagtgag tcgtattaat ttcgcgggat cgagatctga tcaacctgca ttaatgaatc   1560
ggccaacgcg cggggagagg cggtttgcgt attgggcgct cttccgcttc ctcgctcact   1620
gactcgctgc gctcggtcgt tcggctgcgg cgagcggtat cagctcactc aaaggcggta   1680
atacggttat ccacagaatc aggggataac gcaggaaaga acatgtgagc aaaaggccag   1740
caaaaggcca ggaaccgtaa aaaggccgcg ttgctggcgt ttttccatag gctccgcccc   1800
cctgacgagc atcacaaaaa tcgacgctca agtcagaggt ggcgaaaccc gacaggacta   1860
taaagatacc aggcgtttcc ccctggaagc tccctcgtgc gctctcctgt tccgaccctg   1920
ccgcttaccg gatacctgtc cgcctttctc ccttcgggaa gcgtggcgct ttctcaatgc   1980
tcacgctgta ggtatctcag ttcggtgtag tcgttcgctc caagctggg ctgtgtgcac   2040 gaaccccccg ttcagcccga ccgctgcgcc ttatccggta actatcgtct tgagtccaac   2100
ccggtaagac acgacttatc gccactggca gcagccactg gtaacaggat tagcagagcg   2160
aggtatgtag gcggtgctac agagttcttg aagtggtggc ctaactacgg ctacactaga   2220
aggacagtat ttggtatctg cgctctgctg aagccagtta ccttcggaaa agagttggt   2280 agctcttgat ccgcaaaca aaccaccgct ggtagcggtg gtttttttgt ttgcaagcag   2340
cagattacgc gcagaaaaaa aggatctcaa gaagatcctt tgatcttttc tacgggtct   2400 gacgctcagt ggaacgaaaa ctcacgttaa gggattttgg tcatgacatt aacctataaa   2460
aataggcgta tcacgaggcc ctttcgtctc gcgcgtttcg gtgatgacgg tgaaaacctc   2520
tgacacatgc agctcccgga gacggtcaca gcttgtctgt aagcggatgc cgggagcaga   2580
caagcccgtc agggcgcgtc agcgggtgtt ggcgggtgtc ggggctggct taactatgcg   2640
gcatcagagc agattgtact gagagtgcac catatggaca tattgtcgtt agaacgcggc   2700
tacaattaat acataacctt atgtatcata cacatacgat ttaggtgaca ctatagaacg   2760
```

-continued

```
gcgcgccaag cttggatcct cgaagagaag ggttaataac acattttta acatttttaa      2820
cacaaatttt agttatttaa aaatttatta aaaaatttaa aataagaaga ggaactcttt      2880
aaataaatct aacttacaaa atttatgatt tttaataagt tttcaccaat aaaaaatgtc      2940
ataaaaatat gttaaaaagt atattatcaa tattctcttt atgataaata aaaagaaaaa      3000
aaaaataaaa gttaagtgaa atgagattg aagtgacttt aggtgtgtat aaatatatca       3060
accccgccaa caatttattt aatccaaata tattgaagta tattattcca tagcctttat      3120
ttatttatat atttattata taaaagcttt atttgttcta ggttgttcat gaaatatttt      3180
tttggtttta tctccgttgt aagaaaatca tgtgctttgt gtcgccactc actattgcag      3240
cttttttcatg cattggtcag attgacggtt gattgtattt ttgttttta tggttttgtg       3300
ttatgactta agtcttcatc tctttatctc ttcatcaggt ttgatggtta cctaatatgg       3360
tccatgggta catgcatggt taattaggt ggccaacttt gttgtgaacg atagaatttt        3420
ttttatatta agtaaactat ttttatatta tgaaataata ataaaaaaa tatttatca         3480
ttattaacaa aatcatatta gttaatttgt taactctata ataaaagaaa tactgtaaca      3540
ttcacattac atggtaacat ctttccaccc tttcatttgt ttttgtttg atgacttttt        3600
ttcttgttta aatttatttc ccttcttta aatttggaat acattatcat catatataaa        3660
ctaaaatact aaaacagga ttacacaaat gataaataat aacacaaata tttataaatc       3720
tagctgcaat atatttaaac tagctatatc gatattgtaa aataaaacta gctgcattga      3780
tactgataaa aaaatatcat gtgctttctg gactgatgat gcagtatact tttgacattg      3840
cctttatttt attttttcaga aaagctttct tagttctggg ttcttcatta tttgtttccc    3900
atctccattg tgaattgaat catttgcttc gtgtcacaaa tacaatttag ntaggtacat      3960
gcattggtca gattcacggt ttattatgtc atgacttaag ttcatggtag tacattacct      4020
gccacgcatg cattatattg gttagatttg ataggcaaat ttggttgtca acaatataaa      4080
tataaataat gtttttatat tacgaaataa cagtgatcaa aacaaacagt tttatcttta      4140
ttaacaagat tttgttttttg tttgatgacg ttttttaatg tttacgcttt cccccttctt    4200
ttgaatttag aacactttat catcataaaa tcaaatacta aaaaaattac atatttcata      4260
aataataaca caaatatttt taaaaaatct gaaataataa tgaacaatat tacatatat      4320
cacgaaaatt cattaataaa aatattatat aaataaaatg taatagtagt tatatgtagg     4380
aaaaaagtac tgcacgcata atatatacaa aaagattaaa atgaactatt ataaataata     4440
acactaaatt aatggtgaat catatcaaaa taatgaaaaa gtaaatataaa tttgtaatta    4500
acttctatat gtattacaca cacaaataat aaataatagt aaaaaaaatt atgataaata    4560
tttaccatct cataagatat ttaaaataat gataaaaata tagattattt tttatgcaac    4620
tagctagcca aaaagagaac acgggtatat ataaaaagag tacctttaaa ttctactgta    4680
cttccttat tcctgacgtt tttatatcaa gtggacatac gtgaagattt taattatcag    4740
tctaaatatt tcattagcac ttaatacttt tctgttttat tcctatccta taagtagtcc    4800
cgattctccc aacattgctt attcacacaa ctaactaaga aagtcttcca tagccccca     4860
agcggccgga gctggtcatc tcgctcatcg tcgagtcggc ggccggagct ggtcatctcg   4920
ctcatcgtcg agtcggcggc cgccgactcg acgatgagcg agatgaccag ctcc           4974
```

<210> SEQ ID NO 18
<211> LENGTH: 34
<212> TYPE: DNA

<210> SEQ ID NO 18
<211> LENGTH: 34
<212> TYPE: DNA
<213> ORGANISM: Artificial Sequence
<220> FEATURE:
<223> OTHER INFORMATION: Synthetic DNA Linker

<400> SEQUENCE: 18
ggcgcgccaa gcttggatcc gtcgacggcg cgcc                         34

<210> SEQ ID NO 19
<211> LENGTH: 80
<212> TYPE: DNA
<213> ORGANISM: Artificial Sequence
<220> FEATURE:
<223> OTHER INFORMATION: Synthetic Complementary Region of pKS106 and
      pKS124

<400> SEQUENCE: 19
cggccggagc tggtcatctc gctcatcgtc gagtcggcgg ccgccgactc gacgatgagc    60
gagatgacca gctccggccg                                                80

<210> SEQ ID NO 20
<211> LENGTH: 154
<212> TYPE: DNA
<213> ORGANISM: Artificial Sequence
<220> FEATURE:
<223> OTHER INFORMATION: Synthetic Complementary Region of pKS133

<400> SEQUENCE: 20
cggccggagc tggtcatctc gctcatcgtc gagtcggcgg ccggagctgg tcatctcgct    60
catcgtcgag tcggcggccg ccgactcgac gatgagcgag atgaccagct ccggccgccg   120
actcgacgat gagcgagatg accagctccg gccg                               154

<210> SEQ ID NO 21
<211> LENGTH: 92
<212> TYPE: DNA
<213> ORGANISM: Artificial Sequence
<220> FEATURE:
<223> OTHER INFORMATION: Synthetic PCR primer

<400> SEQUENCE: 21
gaattccggc cggagctggt catctcgctc atcgtcgagt cggcggccgc cgactcgacg    60
atgagcgaga tgaccagctc cggccggaat tc                                  92

<210> SEQ ID NO 22
<211> LENGTH: 15
<212> TYPE: DNA
<213> ORGANISM: Artificial Sequence
<220> FEATURE:
<223> OTHER INFORMATION: Synthetic PCR primer

<400> SEQUENCE: 22
gaattccggc cggag                                              15

<210> SEQ ID NO 23
<211> LENGTH: 1874
<212> TYPE: DNA
<213> ORGANISM: Glycine max
<220> FEATURE:
<221> NAME/KEY: CDS
<222> LOCATION: (42)..(1637)

<400> SEQUENCE: 23
ccaaatccaa aaaggtttct atttccgtta ttgatttagc a atg gat tca gct tgt    56
                                             Met Asp Ser Ala Cys
                                              1               5

```
gca acc ctg aat ggc cgc cat cta gcc aaa gtt agt gag gga att gga      104
Ala Thr Leu Asn Gly Arg His Leu Ala Lys Val Ser Glu Gly Ile Gly
             10                  15                  20 aga aac aga aca agt ggc ttc tgg ggt gag agt acg agg gga agt gtg      152
Arg Asn Arg Thr Ser Gly Phe Trp Gly Glu Ser Thr Arg Gly Ser Val
         25                  30                  35 aac aca aaa agg ttt ttg agt gtt caa tca tgc aag act tca cga acc      200
Asn Thr Lys Arg Phe Leu Ser Val Gln Ser Cys Lys Thr Ser Arg Thr
     40                  45                  50 aat agg aat ctt aga aac tcc aag cct gga agt gga att gca cgc gct      248
Asn Arg Asn Leu Arg Asn Ser Lys Pro Gly Ser Gly Ile Ala Arg Ala
 55                  60                  65 gtt ctc aca tca gac atc gac gaa gat tcc atg gca ttt caa ggg gta      296
Val Leu Thr Ser Asp Ile Asp Glu Asp Ser Met Ala Phe Gln Gly Val
 70              75                  80                  85 ccc act ttt gag aaa cct gaa gtg gac cca aaa agt gtg gct tcc atc      344
Pro Thr Phe Glu Lys Pro Glu Val Asp Pro Lys Ser Val Ala Ser Ile
                 90                  95                 100 ata ttg ggt gga ggt gca gga act cga ctc ttt cct ctt act ggc aga      392
Ile Leu Gly Gly Gly Ala Gly Thr Arg Leu Phe Pro Leu Thr Gly Arg
             105                 110                 115 aga gcc aag cca gcg gtt cca att gga ggg tgt tat aga ctc ata gat      440
Arg Ala Lys Pro Ala Val Pro Ile Gly Gly Cys Tyr Arg Leu Ile Asp
         120                 125                 130 atc ccc atg agc aat tgc atc aat agt ggc atc aga aaa att ttc atc      488
Ile Pro Met Ser Asn Cys Ile Asn Ser Gly Ile Arg Lys Ile Phe Ile
     135                 140                 145 ttg acg cag ttc aat tct ttc tct ctc aac cgc cac ctg tcc cgt gca      536
Leu Thr Gln Phe Asn Ser Phe Ser Leu Asn Arg His Leu Ser Arg Ala
150                 155                 160                 165 tac agc ttc gga aat ggc atg act ttt gga gat ggg ttt gtg gag gtc      584
Tyr Ser Phe Gly Asn Gly Met Thr Phe Gly Asp Gly Phe Val Glu Val
             170                 175                 180 ttg gca gct act caa aca ccg ggt gag gct ggg aag aag tgg ttc caa      632
Leu Ala Ala Thr Gln Thr Pro Gly Glu Ala Gly Lys Lys Trp Phe Gln
         185                 190                 195 ggg aca gct gat gct gta aga caa ttt ata tgg gtt ttt gag gat gcc      680
Gly Thr Ala Asp Ala Val Arg Gln Phe Ile Trp Val Phe Glu Asp Ala
     200                 205                 210 aag aac aag aat gtt gag cat ata ttg ata ctt tct ggc gat cat ctt      728
Lys Asn Lys Asn Val Glu His Ile Leu Ile Leu Ser Gly Asp His Leu
215                 220                 225 tac cgt atg gac tat atg gac ttt gta cag aga cat gtt gac aca aat      776
Tyr Arg Met Asp Tyr Met Asp Phe Val Gln Arg His Val Asp Thr Asn
230                 235                 240                 245 gcc gat atc aca gtt tca tgt gta ccc atg gat gac agt cgg gca tca      824
Ala Asp Ile Thr Val Ser Cys Val Pro Met Asp Asp Ser Arg Ala Ser
             250                 255                 260 gac tat gga ctg atg aaa att gat aaa aca gga cgg att ata cag ttt      872
Asp Tyr Gly Leu Met Lys Ile Asp Lys Thr Gly Arg Ile Ile Gln Phe
         265                 270                 275 gca gaa aaa cct aag gga tca gat cta aag gca atg cgt gtt gac acc      920
Ala Glu Lys Pro Lys Gly Ser Asp Leu Lys Ala Met Arg Val Asp Thr
     280                 285                 290 act ctt tta ggg tta ttg cca caa gaa gca gaa aaa cat cct tat att      968
Thr Leu Leu Gly Leu Leu Pro Gln Glu Ala Glu Lys His Pro Tyr Ile
295                 300                 305 gca tcc atg ggt gtc tac gtg ttt aga act gaa acc ttg ctg caa cta     1016
Ala Ser Met Gly Val Tyr Val Phe Arg Thr Glu Thr Leu Leu Gln Leu
```

| | | |
|---|---|---|
| tta aga tgg aaa tgt tct tca tgc aat gac ttt gga tct gaa att atc<br>Leu Arg Trp Lys Cys Ser Ser Cys Asn Asp Phe Gly Ser Glu Ile Ile<br>              330                    335                    340 | 1064 |
| cca tct gct gtg aat gag cac aat gtc cag gca tat ttg ttc aat gac<br>Pro Ser Ala Val Asn Glu His Asn Val Gln Ala Tyr Leu Phe Asn Asp<br>          345                      350                    355 | 1112 |
| tac tgg gaa gat att gga act ata aag tcc ttc ttt gat gca aat ctt<br>Tyr Trp Glu Asp Ile Gly Thr Ile Lys Ser Phe Phe Asp Ala Asn Leu<br>              360                    365                    370 | 1160 |
| gct cta aca gaa cag cct cct aaa ttt gaa ttc tat gat cca aag aca<br>Ala Leu Thr Glu Gln Pro Pro Lys Phe Glu Phe Tyr Asp Pro Lys Thr<br>375                    380                    385 | 1208 |
| cct ttc ttc act tcc ccc aga ttc cta cca cct acc aaa gta gaa aaa<br>Pro Phe Phe Thr Ser Pro Arg Phe Leu Pro Pro Thr Lys Val Glu Lys<br>390                    395                    400                    405 | 1256 |
| tgc aag att gtg gat gca att ata tct cat ggt tgc ttc ttg agg gag<br>Cys Lys Ile Val Asp Ala Ile Ile Ser His Gly Cys Phe Leu Arg Glu<br>              410                    415                    420 | 1304 |
| tgc agc gtt caa cat tct att gtt gga gta cgc tca cgt ttg gag tct<br>Cys Ser Val Gln His Ser Ile Val Gly Val Arg Ser Arg Leu Glu Ser<br>          425                      430                    435 | 1352 |
| ggt gtg gag ctt cag gat acg atg atg atg ggt gct gac tat tat caa<br>Gly Val Glu Leu Gln Asp Thr Met Met Met Gly Ala Asp Tyr Tyr Gln<br>              440                    445                    450 | 1400 |
| act gag tat gaa att gca tct ctg gtg gca gaa ggg aag gtt cca att<br>Thr Glu Tyr Glu Ile Ala Ser Leu Val Ala Glu Gly Lys Val Pro Ile<br>          455                      460                    465 | 1448 |
| ggt gtc ggg gca aat act aaa atc agg aat tgc ata atc gac aag aat<br>Gly Val Gly Ala Asn Thr Lys Ile Arg Asn Cys Ile Ile Asp Lys Asn<br>470                    475                    480                    485 | 1496 |
| gcc aag ata gga aga aat gtg atc ata gca aac acc gat ggt gtt caa<br>Ala Lys Ile Gly Arg Asn Val Ile Ile Ala Asn Thr Asp Gly Val Gln<br>              490                    495                    500 | 1544 |
| gaa gct gac agg gca aag gaa gga ttc tac att agg tcg ggc atc aca<br>Glu Ala Asp Arg Ala Lys Glu Gly Phe Tyr Ile Arg Ser Gly Ile Thr<br>          505                      510                    515 | 1592 |
| gtt aca tta aaa aat gca aca atc aaa gat gga aca gtt ata tga<br>Val Thr Leu Lys Asn Ala Thr Ile Lys Asp Gly Thr Val Ile<br>520                    525                    530 | 1637 |
| agcacttcaa gttatccagc aggccacttt ataatagttt tgacataagt acattcactt | 1697 |
| ccgacataat agtagatgaa atgctagctc gtacattaca aagtttctct cgatatatct | 1757 |
| ctataatagt tatgtttatt gcatttgtag gacacttcac ttgtaataac aggcaattct | 1817 |
| tgccactacg attaagttat aaattaaagt ttctaactca aaaaaaaaaa aaaaaaa | 1874 |

<210> SEQ ID NO 24
<211> LENGTH: 531
<212> TYPE: PRT
<213> ORGANISM: Glycine max

<400> SEQUENCE: 24

Met Asp Ser Ala Cys Ala Thr Leu Asn Gly Arg His Leu Ala Lys Val
1                  5                    10                    15

Ser Glu Gly Ile Gly Arg Asn Arg Thr Ser Gly Phe Trp Gly Glu Ser
                20                    25                    30

Thr Arg Gly Ser Val Asn Thr Lys Arg Phe Leu Ser Val Gln Ser Cys
          35                      40                    45

-continued

```
Lys Thr Ser Arg Thr Asn Arg Asn Leu Arg Asn Ser Lys Pro Gly Ser
 50                  55                  60

Gly Ile Ala Arg Ala Val Leu Thr Ser Asp Ile Asp Glu Asp Ser Met
 65                  70                  75                  80

Ala Phe Gln Gly Val Pro Thr Phe Glu Lys Pro Glu Val Asp Pro Lys
                 85                  90                  95

Ser Val Ala Ser Ile Ile Leu Gly Gly Gly Ala Gly Thr Arg Leu Phe
                100                 105                 110

Pro Leu Thr Gly Arg Arg Ala Lys Pro Ala Val Pro Ile Gly Gly Cys
            115                 120                 125

Tyr Arg Leu Ile Asp Ile Pro Met Ser Asn Cys Ile Asn Ser Gly Ile
    130                 135                 140

Arg Lys Ile Phe Ile Leu Thr Gln Phe Asn Ser Phe Ser Leu Asn Arg
145                 150                 155                 160

His Leu Ser Arg Ala Tyr Ser Phe Gly Asn Gly Met Thr Phe Gly Asp
                165                 170                 175

Gly Phe Val Glu Val Leu Ala Ala Thr Gln Thr Pro Gly Glu Ala Gly
            180                 185                 190

Lys Lys Trp Phe Gln Gly Thr Ala Asp Ala Val Arg Gln Phe Ile Trp
    195                 200                 205

Val Phe Glu Asp Ala Lys Asn Lys Asn Val Glu His Ile Leu Ile Leu
210                 215                 220

Ser Gly Asp His Leu Tyr Arg Met Asp Tyr Met Asp Phe Val Gln Arg
225                 230                 235                 240

His Val Asp Thr Asn Ala Asp Ile Thr Val Ser Cys Val Pro Met Asp
                245                 250                 255

Asp Ser Arg Ala Ser Asp Tyr Gly Leu Met Lys Ile Asp Lys Thr Gly
            260                 265                 270

Arg Ile Ile Gln Phe Ala Glu Lys Pro Lys Gly Ser Asp Leu Lys Ala
    275                 280                 285

Met Arg Val Asp Thr Thr Leu Leu Gly Leu Leu Pro Gln Glu Ala Glu
290                 295                 300

Lys His Pro Tyr Ile Ala Ser Met Gly Val Tyr Val Phe Arg Thr Glu
305                 310                 315                 320

Thr Leu Leu Gln Leu Leu Arg Trp Lys Cys Ser Ser Cys Asn Asp Phe
                325                 330                 335

Gly Ser Glu Ile Ile Pro Ser Ala Val Asn Glu His Asn Val Gln Ala
            340                 345                 350

Tyr Leu Phe Asn Asp Tyr Trp Glu Asp Ile Gly Thr Ile Lys Ser Phe
    355                 360                 365

Phe Asp Ala Asn Leu Ala Leu Thr Glu Gln Pro Pro Lys Phe Glu Phe
370                 375                 380

Tyr Asp Pro Lys Thr Pro Phe Phe Thr Ser Pro Arg Phe Leu Pro Pro
385                 390                 395                 400

Thr Lys Val Glu Lys Cys Lys Ile Val Asp Ala Ile Ile Ser His Gly
                405                 410                 415

Cys Phe Leu Arg Glu Cys Ser Val Gln His Ser Ile Val Gly Val Arg
            420                 425                 430

Ser Arg Leu Glu Ser Gly Val Glu Leu Gln Asp Thr Met Met Met Gly
    435                 440                 445

Ala Asp Tyr Tyr Gln Thr Glu Tyr Glu Ile Ala Ser Leu Val Ala Glu
450                 455                 460

Gly Lys Val Pro Ile Gly Val Gly Ala Asn Thr Lys Ile Arg Asn Cys
```

```
            465                 470                 475                 480
Ile Ile Asp Lys Asn Ala Lys Ile Gly Arg Asn Val Ile Ile Ala Asn
                485                 490                 495

Thr Asp Gly Val Gln Glu Ala Asp Arg Ala Lys Glu Gly Phe Tyr Ile
            500                 505                 510

Arg Ser Gly Ile Thr Val Thr Leu Lys Asn Ala Thr Ile Lys Asp Gly
            515                 520                 525

Thr Val Ile
        530

<210> SEQ ID NO 25
<211> LENGTH: 521
<212> TYPE: PRT
<213> ORGANISM: Cicer arietinum

<400> SEQUENCE: 25

Met Asp Leu Ala Ile Gly Ser Asn Tyr Ala Ser Leu Arg Ser Ser Val
1               5                   10                  15

Phe Leu Gly Glu Thr Leu Lys Gly Asn Leu Ser Thr Lys Phe Leu Thr
            20                  25                  30

Ser Pro Lys Phe Ser Gln Ile His Ile Asn Asn Leu Arg Ser Phe Asn
        35                  40                  45

Pro Arg Asn Gly Ala Ser Tyr Ser Val Leu Thr Ser Gly Ile Asn Asp
    50                  55                  60

Phe Glu Glu Ser Met Thr Phe His Glu Gly Pro Tyr Phe Asp Thr Pro
65                  70                  75                  80

Lys Ala Asp Pro Lys Ser Val Ala Ser Ile Ile Leu Gly Gly Ala
                85                  90                  95

Gly Thr Arg Leu Phe Pro Leu Thr Ser Lys Arg Ala Lys Pro Ala Val
            100                 105                 110

Pro Ile Gly Gly Cys Tyr Arg Leu Ile Asp Ile Pro Met Ser Asn Cys
            115                 120                 125

Ile Asn Ser Gly Ile Arg Lys Ile Phe Ile Leu Thr Gln Phe Asn Ser
    130                 135                 140

Phe Ser Leu Asn Arg His Leu Ser Arg Ser Tyr Asn Phe Gly Asn Val
145                 150                 155                 160

Ser Thr Phe Gly Glu Gly Phe Val Glu Val Leu Ala Ala Thr Gln Thr
            165                 170                 175

Ser Gly Glu Ala Gly Lys Lys Trp Phe Gln Gly Thr Ala Asp Ala Val
            180                 185                 190

Arg Gln Phe Ile Trp Val Phe Glu Asp Ala Lys Thr Lys Asn Val Glu
            195                 200                 205

His Ile Leu Ile Leu Ser Gly Asp His Leu Tyr Arg Met Asn Tyr Met
    210                 215                 220

Asp Phe Val Gln Lys His Ile Asp Thr Asn Ala Asp Ile Thr Val Ser
225                 230                 235                 240

Cys Ile Pro Met Asp Asp Ser Arg Ala Ser Asp Tyr Gly Leu Leu Lys
            245                 250                 255

Ile Asp Gly Lys Gly Arg Ile Ile Gln Phe Ala Glu Lys Pro Lys Gly
            260                 265                 270

Ser Glu Leu Lys Ala Met Arg Val Asp Thr Thr Leu Leu Gly Leu Ser
            275                 280                 285

Pro Glu Glu Ala Lys Lys Gln Pro Tyr Ile Ala Ser Met Gly Val Tyr
    290                 295                 300
```

-continued

```
Val Phe Arg Thr Glu Thr Leu Leu Lys Leu Leu Arg Ser Asn Cys Ser
305                 310                 315                 320

Thr Cys Asn Asp Phe Gly Ser Glu Ile Ile Pro Ser Ala Val Asn Asp
                325                 330                 335

Asp His Asn Val Gln Ala Tyr Leu Phe Asn Asp Tyr Trp Glu Asp Ile
            340                 345                 350

Gly Thr Ile Lys Ser Phe Phe Asp Ala Asn Leu Ala Leu Thr Asp Gln
        355                 360                 365

Pro Pro Lys Phe Gln Phe Tyr Asp Pro Asn Thr Pro Phe Tyr Thr Phe
    370                 375                 380

Pro Arg Phe Leu Pro Pro Thr Lys Val Glu Lys Cys Lys Ile Val Asp
385                 390                 395                 400

Ala Ile Ile Ser His Gly Cys Phe Leu Arg Glu Cys Ser Val Gln His
                405                 410                 415

Ser Ile Val Gly Ile Arg Ser Arg Leu Glu Ser Gly Val Glu Leu Gln
            420                 425                 430

Asp Thr Met Met Met Gly Ala Asp Tyr Tyr Gln Thr Glu Ser Glu Ile
        435                 440                 445

Ala Ser Leu Leu Ala Glu Gly Lys Val Pro Val Gly Val Gly Glu Asn
    450                 455                 460

Thr Lys Ile Arg Asn Cys Ile Ile Asp Lys Asn Ala Arg Ile Gly Arg
465                 470                 475                 480

Asn Val Ile Ile Thr Asn Ala Asp Gly Val Glu Glu Ala Asp Arg Thr
                485                 490                 495

Lys Glu Gly Phe Tyr Ile Arg Ser Gly Ile Thr Ala Ile Leu Lys Asn
            500                 505                 510

Ala Thr Ile Lys Asp Gly Thr Val Ile
        515                 520

<210> SEQ ID NO 26
<211> LENGTH: 531
<212> TYPE: PRT
<213> ORGANISM: Glycine max
<220> FEATURE:
<221> NAME/KEY: misc_feature
<222> LOCATION: (404)..(404)
<223> OTHER INFORMATION: Xaa can be any naturally occurring amino acid

<400> SEQUENCE: 26

Met Asp Ser Ala Cys Ala Thr Leu Asn Gly Arg His Leu Ala Lys Val
1               5                   10                  15

Ser Glu Gly Ile Gly Arg Asn Arg Thr Ser Gly Phe Trp Gly Glu Ser
            20                  25                  30

Thr Arg Gly Ser Val Asn Thr Lys Arg Phe Leu Ser Val Gln Ser Cys
        35                  40                  45

Lys Thr Ser Arg Thr Asn Arg Asn Leu Arg Asn Ser Lys Pro Gly Ser
    50                  55                  60

Gly Ile Ala Arg Ala Val Leu Thr Ser Asp Ile Asp Glu Asp Ser Met
65                  70                  75                  80

Ala Phe Gln Gly Val Pro Thr Phe Glu Lys Pro Glu Val Asp Pro Lys
                85                  90                  95

Ser Val Ala Ser Ile Ile Leu Gly Gly Gly Ala Gly Thr Arg Leu Phe
            100                 105                 110

Pro Leu Thr Gly Arg Arg Ala Lys Pro Ala Val Pro Ile Gly Gly Cys
        115                 120                 125

Tyr Arg Leu Ile Asp Ile Pro Met Ser Asn Cys Ile Asn Ser Gly Ile
```

-continued

```
            130                 135                 140
Arg Lys Ile Phe Ile Leu Thr Gln Phe Asn Ser Phe Ser Leu Asn Arg
145                 150                 155                 160

His Leu Ser Arg Ala Tyr Ser Phe Gly Asn Gly Met Thr Phe Gly Asp
                165                 170                 175

Gly Phe Val Glu Val Leu Ala Ala Thr Gln Thr Pro Gly Glu Ala Gly
                180                 185                 190

Lys Lys Trp Phe Gln Gly Thr Ala Asp Ala Val Arg Gln Phe Ile Trp
                195                 200                 205

Val Phe Glu Asp Ala Lys Asn Lys Asn Val Glu His Ile Leu Ile Leu
210                 215                 220

Ser Gly Asp His Leu Tyr Arg Met Asp Tyr Met Asp Phe Val Gln Arg
225                 230                 235                 240

His Val Asp Thr Asn Ala Asp Ile Thr Val Ser Cys Val Pro Met Asp
                245                 250                 255

Asp Ser Arg Ala Ser Asp Tyr Gly Leu Met Lys Ile Asp Lys Thr Gly
                260                 265                 270

Arg Ile Ile Gln Phe Ala Glu Lys Pro Lys Gly Ser Asp Leu Lys Ala
                275                 280                 285

Met Arg Val Asp Thr Thr Leu Leu Gly Leu Leu Pro Gln Glu Ala Glu
                290                 295                 300

Lys His Pro Tyr Ile Ala Ser Met Gly Val Tyr Val Phe Arg Thr Glu
305                 310                 315                 320

Thr Leu Leu Gln Leu Leu Arg Trp Lys Gly Ser Ser Cys Asn Asp Phe
                325                 330                 335

Gly Ser Glu Ile Ile Pro Ser Ala Val Asn Glu His Asn Val Gln Ala
                340                 345                 350

Tyr Leu Phe Asn Asp Tyr Trp Glu Asp Ile Gly Thr Ile Lys Ser Phe
                355                 360                 365

Phe Asp Ala Asn Leu Ala Leu Thr Glu Gln Pro Pro Lys Phe Glu Phe
                370                 375                 380

Tyr Asp Pro Lys Thr Pro Phe Phe Thr Ser Pro Arg Phe Leu Pro Pro
385                 390                 395                 400

Thr Lys Val Xaa Lys Cys Lys Ile Val Asp Ala Ile Ile Ser His Gly
                405                 410                 415

Cys Phe Leu Arg Glu Cys Ser Val Gln His Ser Ile Val Gly Val Arg
                420                 425                 430

Ser Arg Leu Glu Ser Gly Val Glu Leu Gln Asp Thr Met Met Met Gly
                435                 440                 445

Ala Asp Tyr Tyr Gln Thr Glu Tyr Glu Ile Ala Ser Leu Val Ala Glu
450                 455                 460

Gly Lys Val Pro Ile Gly Val Gly Ala Asn Thr Lys Ile Arg Asn Cys
465                 470                 475                 480

Ile Ile Asp Lys Asn Ala Lys Ile Gly Arg Asn Val Ile Ile Ala Asn
                485                 490                 495

Thr Asp Gly Val Gln Glu Ala Asp Arg Ala Lys Glu Gly Phe Tyr Ile
                500                 505                 510

Arg Ser Gly Ile Thr Val Thr Leu Lys Asn Ala Thr Ile Lys Asp Gly
                515                 520                 525

Thr Val Ile
530
```

<210> SEQ ID NO 27

```
<211> LENGTH: 1886
<212> TYPE: DNA
<213> ORGANISM: Glycine max
<220> FEATURE:
<221> NAME/KEY: CDS
<222> LOCATION: (80)..(1627)

<400> SEQUENCE: 27
gcacgagtta aagagagtca caagccaatt ctgaaccaca cactcactta tttgtttctt         60
tcaactcact cacagagta atg gca tcc atg gcg gct ata ggt tct ctg aat        112
                     Met Ala Ser Met Ala Ala Ile Gly Ser Leu Asn
                       1               5                  10 gtt cct tgt tct gct tct tcg cgt tca tcg aat gtg gga aga aaa agc         160
Val Pro Cys Ser Ala Ser Ser Arg Ser Ser Asn Val Gly Arg Lys Ser
         15                  20                  25 ttt cca cgc agc ctt tca ttc tct gca tca caa ctt tgt gga gac aag         208
Phe Pro Arg Ser Leu Ser Phe Ser Ala Ser Gln Leu Cys Gly Asp Lys
     30                  35                  40 att cac aca gat tca gtt tca ttc gca cca aaa atc ggt cgc aat cct         256
Ile His Thr Asp Ser Val Ser Phe Ala Pro Lys Ile Gly Arg Asn Pro
 45                  50                  55 gta att gtt acc cct aaa gca gtt tct gat tcc caa aac tcc caa acc         304
Val Ile Val Thr Pro Lys Ala Val Ser Asp Ser Gln Asn Ser Gln Thr
 60                  65                  70                  75 tgt ctt gat ccc gat gct agc aga agt gtg ctt ggc att ata ctt gga         352
Cys Leu Asp Pro Asp Ala Ser Arg Ser Val Leu Gly Ile Ile Leu Gly
                 80                  85                  90 ggt ggt gct ggg act cgt ctt tat cca ctg acc aag aag agg gca aag         400
Gly Gly Ala Gly Thr Arg Leu Tyr Pro Leu Thr Lys Lys Arg Ala Lys
             95                 100                 105 cca gct gtt cct ctt gga gct aac tat agg cta att gac att cct gtt         448
Pro Ala Val Pro Leu Gly Ala Asn Tyr Arg Leu Ile Asp Ile Pro Val
         110                 115                 120 agc aac tgc ttg aat agc aac gtc tcc aag atc tat gtt ctc act caa         496
Ser Asn Cys Leu Asn Ser Asn Val Ser Lys Ile Tyr Val Leu Thr Gln
 125                 130                 135 ttc aat tcc gcc tcg tta aac cga cac ctt tct cgt gct tat gca agc         544
Phe Asn Ser Ala Ser Leu Asn Arg His Leu Ser Arg Ala Tyr Ala Ser
140                 145                 150                 155 aac atg ggt ggc tac aaa aat gag gga ttt gtt gag gtt ctt gct gct         592
Asn Met Gly Gly Tyr Lys Asn Glu Gly Phe Val Glu Val Leu Ala Ala
                 160                 165                 170 cag cag agt cct gag aat cct aat tgg ttc cag ggt act gca gat gct         640
Gln Gln Ser Pro Glu Asn Pro Asn Trp Phe Gln Gly Thr Ala Asp Ala
             175                 180                 185 gtc agg cag tat ttg tgg ctt ttt gaa gag cac aat gtt ttg gaa ttc         688
Val Arg Gln Tyr Leu Trp Leu Phe Glu Glu His Asn Val Leu Glu Phe
         190                 195                 200 ttg gtt ctg gct ggt gac cat ttg tat cga atg gat tac gag aaa ttt         736
Leu Val Leu Ala Gly Asp His Leu Tyr Arg Met Asp Tyr Glu Lys Phe
 205                 210                 215 atc caa gcg cat agg gaa act gat gct gat atc act gtg gct gca ttg         784
Ile Gln Ala His Arg Glu Thr Asp Ala Asp Ile Thr Val Ala Ala Leu
220                 225                 230                 235 cca atg gat gaa aag cgt gcc act gca ttt ggc ctg atg aag att gat         832
Pro Met Asp Glu Lys Arg Ala Thr Ala Phe Gly Leu Met Lys Ile Asp
                 240                 245                 250 gaa gag ggg cgt ata att gaa ttc gcc gaa aag cca aaa gga gaa cag         880
Glu Glu Gly Arg Ile Ile Glu Phe Ala Glu Lys Pro Lys Gly Glu Gln
             255                 260                 265 ttg aaa gct atg aag gtt gat act aca att ttg ggt ctt gat gac gag         928
Leu Lys Ala Met Lys Val Asp Thr Thr Ile Leu Gly Leu Asp Asp Glu
```

```
Leu Lys Ala Met Lys Val Asp Thr Thr Ile Leu Gly Leu Asp Asp Glu
            270                 275                 280 aga gca aag gaa ttg cct tat att gct agc atg ggt ata tat gtt gtt      976
Arg Ala Lys Glu Leu Pro Tyr Ile Ala Ser Met Gly Ile Tyr Val Val
285                 290                 295 agc aaa aac gtg atg tta gac ctg ctc cgt gag aag ttt cct ggt gca     1024
Ser Lys Asn Val Met Leu Asp Leu Leu Arg Glu Lys Phe Pro Gly Ala
300                 305                 310                 315 aat gac ttt ggg agt gaa gtg att cct ggt gct act tct att gga atg     1072
Asn Asp Phe Gly Ser Glu Val Ile Pro Gly Ala Thr Ser Ile Gly Met
            320                 325                 330 agg gtg caa gct tac ttg tat gat ggc tac tgg gaa gac att ggt aca     1120
Arg Val Gln Ala Tyr Leu Tyr Asp Gly Tyr Trp Glu Asp Ile Gly Thr
            335                 340                 345 att gag gct ttc tat aat gca aat ctg gga atc acc aaa aag cct gtg     1168
Ile Glu Ala Phe Tyr Asn Ala Asn Leu Gly Ile Thr Lys Lys Pro Val
            350                 355                 360 cct gac ttc agt ttc tat gat cgt tca tct cca atc tac acc caa cca     1216
Pro Asp Phe Ser Phe Tyr Asp Arg Ser Ser Pro Ile Tyr Thr Gln Pro
365                 370                 375 cga tat ttg cct ccc tct aag atg ctt gat gct gat gtc act gat agt     1264
Arg Tyr Leu Pro Pro Ser Lys Met Leu Asp Ala Asp Val Thr Asp Ser
380                 385                 390                 395 gtt att ggt gaa gga tgt gtg att aag aac tgc aaa att cac cat tct     1312
Val Ile Gly Glu Gly Cys Val Ile Lys Asn Cys Lys Ile His His Ser
            400                 405                 410 gtg gtt ggg ctg cga tct tgc ata tca gaa ggt gca att att gaa gac     1360
Val Val Gly Leu Arg Ser Cys Ile Ser Glu Gly Ala Ile Ile Glu Asp
            415                 420                 425 acg tta tta atg ggg gca gat tat tac gag acg gag gct gat aag agg     1408
Thr Leu Leu Met Gly Ala Asp Tyr Tyr Glu Thr Glu Ala Asp Lys Arg
            430                 435                 440 ttt ctg gct gct aaa ggc agt gtt cca att ggt ata ggc agg aac tct     1456
Phe Leu Ala Ala Lys Gly Ser Val Pro Ile Gly Ile Gly Arg Asn Ser
            445                 450                 455 cat atc aaa agg gca att atc gac aag aat gct cga att ggg gaa aat     1504
His Ile Lys Arg Ala Ile Ile Asp Lys Asn Ala Arg Ile Gly Glu Asn
460                 465                 470                 475 gtc aag att att aac agt gac aat gtc caa gaa gct gca agg gaa aca     1552
Val Lys Ile Ile Asn Ser Asp Asn Val Gln Glu Ala Ala Arg Glu Thr
            480                 485                 490 gat ggg tat ttc ata aaa agt ggg att gtc aca gta atc aag gat gct     1600
Asp Gly Tyr Phe Ile Lys Ser Gly Ile Val Thr Val Ile Lys Asp Ala
            495                 500                 505 tta att cct agt gga aca gtc atc taa acaccaccac caccccaaaa          1647
Leu Ile Pro Ser Gly Thr Val Ile
510                 515 aatttcttgt accccaaatc ctaatggtga ctgcaaagct cattaccacc gctggagagt   1707
ttatcaagct atgcttcctc gtctaagata ggcttttgtg tttcatgata tttatttttg   1767
ggcagtggct tgtaaattat agcgggagag aaggcccgct atgagcaatc acgctgtaaa   1827
gttcattatt caattgaata aaagtttctt cgtttcgtac taaaaaaaaa aaaaaaaaa    1886

<210> SEQ ID NO 28
<211> LENGTH: 515
<212> TYPE: PRT
<213> ORGANISM: Glycine max

<400> SEQUENCE: 28
```

-continued

```
Met Ala Ser Met Ala Ala Ile Gly Ser Leu Asn Val Pro Cys Ser Ala
1               5                   10                  15

Ser Ser Arg Ser Ser Asn Val Gly Arg Lys Ser Phe Pro Arg Ser Leu
            20                  25                  30

Ser Phe Ser Ala Ser Gln Leu Cys Gly Asp Lys Ile His Thr Asp Ser
        35                  40                  45

Val Ser Phe Ala Pro Lys Ile Gly Arg Asn Pro Val Ile Val Thr Pro
    50                  55                  60

Lys Ala Val Ser Asp Ser Gln Asn Ser Gln Thr Cys Leu Asp Pro Asp
65                  70                  75                  80

Ala Ser Arg Ser Val Leu Gly Ile Ile Leu Gly Gly Ala Gly Thr
                85                  90                  95

Arg Leu Tyr Pro Leu Thr Lys Lys Arg Ala Lys Pro Ala Val Pro Leu
            100                 105                 110

Gly Ala Asn Tyr Arg Leu Ile Asp Ile Pro Val Ser Asn Cys Leu Asn
            115                 120                 125

Ser Asn Val Ser Lys Ile Tyr Val Leu Thr Gln Phe Asn Ser Ala Ser
        130                 135                 140

Leu Asn Arg His Leu Ser Arg Ala Tyr Ala Ser Asn Met Gly Gly Tyr
145                 150                 155                 160

Lys Asn Glu Gly Phe Val Glu Val Leu Ala Ala Gln Ser Pro Glu
                165                 170                 175

Asn Pro Asn Trp Phe Gln Gly Thr Ala Asp Ala Val Arg Gln Tyr Leu
            180                 185                 190

Trp Leu Phe Glu Glu His Asn Val Leu Glu Phe Leu Val Leu Ala Gly
        195                 200                 205

Asp His Leu Tyr Arg Met Asp Tyr Glu Lys Phe Ile Gln Ala His Arg
    210                 215                 220

Glu Thr Asp Ala Asp Ile Thr Val Ala Ala Leu Pro Met Asp Glu Lys
225                 230                 235                 240

Arg Ala Thr Ala Phe Gly Leu Met Lys Ile Asp Glu Glu Gly Arg Ile
                245                 250                 255

Ile Glu Phe Ala Glu Lys Pro Lys Gly Glu Gln Leu Lys Ala Met Lys
            260                 265                 270

Val Asp Thr Thr Ile Leu Gly Leu Asp Asp Glu Arg Ala Lys Glu Leu
        275                 280                 285

Pro Tyr Ile Ala Ser Met Gly Ile Tyr Val Val Ser Lys Asn Val Met
    290                 295                 300

Leu Asp Leu Leu Arg Glu Lys Phe Pro Gly Ala Asn Asp Phe Gly Ser
305                 310                 315                 320

Glu Val Ile Pro Gly Ala Thr Ser Ile Gly Met Arg Val Gln Ala Tyr
                325                 330                 335

Leu Tyr Asp Gly Tyr Trp Glu Asp Ile Gly Thr Ile Glu Ala Phe Tyr
            340                 345                 350

Asn Ala Asn Leu Gly Ile Thr Lys Lys Pro Val Pro Asp Phe Ser Phe
        355                 360                 365

Tyr Asp Arg Ser Ser Pro Ile Tyr Thr Gln Pro Arg Tyr Leu Pro Pro
    370                 375                 380

Ser Lys Met Leu Asp Ala Asp Val Thr Asp Ser Val Ile Gly Glu Gly
385                 390                 395                 400

Cys Val Ile Lys Asn Cys Lys Ile His His Ser Val Val Gly Leu Arg
                405                 410                 415

Ser Cys Ile Ser Glu Gly Ala Ile Ile Glu Asp Thr Leu Leu Met Gly
```

```
                420             425             430
Ala Asp Tyr Tyr Glu Thr Glu Ala Asp Lys Arg Phe Leu Ala Ala Lys
            435             440             445

Gly Ser Val Pro Ile Gly Ile Gly Arg Asn Ser His Ile Lys Arg Ala
        450             455             460

Ile Ile Asp Lys Asn Ala Arg Ile Gly Glu Asn Val Lys Ile Ile Asn
465             470             475             480

Ser Asp Asn Val Gln Glu Ala Ala Arg Glu Thr Asp Gly Tyr Phe Ile
                485             490             495

Lys Ser Gly Ile Val Thr Val Ile Lys Asp Ala Leu Ile Pro Ser Gly
            500             505             510

Thr Val Ile
        515

<210> SEQ ID NO 29
<211> LENGTH: 1856
<212> TYPE: DNA
<213> ORGANISM: Glycine max
<220> FEATURE:
<221> NAME/KEY: CDS
<222> LOCATION: (47)..(1594)

<400> SEQUENCE: 29
ctttcaaccg agacactcac aagtcacaac acacacacac atagca atg gca tct       55
                                                Met Ala Ser
                                                  1 atg gcg gct ata ggt tct ctc aat gtt cca cgt tct gct tct tcc cgt    103
Met Ala Ala Ile Gly Ser Leu Asn Val Pro Arg Ser Ala Ser Ser Arg
    5                  10                  15 tca tcc ttt gtg gga aga aaa agc gtt cca cgc agc ctt tcc ttc tct    151
Ser Ser Phe Val Gly Arg Lys Ser Val Pro Arg Ser Leu Ser Phe Ser
 20                  25                  30                  35 gca tca caa ctt tgt gga gac aag att ccc aca gat tca gtt tta ttg    199
Ala Ser Gln Leu Cys Gly Asp Lys Ile Pro Thr Asp Ser Val Leu Leu
                 40                  45                  50 gca cca aaa ata ggt cgc agt cca gtt atc gtt act cct aaa gca gtt    247
Ala Pro Lys Ile Gly Arg Ser Pro Val Ile Val Thr Pro Lys Ala Val
             55                  60                  65 tct gat tcc caa aac tca caa acg tgc ctt gat ccc gat gct agc aga    295
Ser Asp Ser Gln Asn Ser Gln Thr Cys Leu Asp Pro Asp Ala Ser Arg
         70                  75                  80 agt gtg ctt ggc att ata ctt gga ggt ggt gct ggg act cgg ctt tat    343
Ser Val Leu Gly Ile Ile Leu Gly Gly Gly Ala Gly Thr Arg Leu Tyr
     85                  90                  95 cca ctc acc aag aag agg gca aag cca gct gtt cct ctt gga gct aac    391
Pro Leu Thr Lys Lys Arg Ala Lys Pro Ala Val Pro Leu Gly Ala Asn
100                 105                 110                 115 tat agg ctt att gat att cct gtt agc aac tgc ttg aat agc aat gtc    439
Tyr Arg Leu Ile Asp Ile Pro Val Ser Asn Cys Leu Asn Ser Asn Val
                120                 125                 130 tcc aag atc tat gtt ctc act caa ttc aat tct gcg tcg tta aac cga    487
Ser Lys Ile Tyr Val Leu Thr Gln Phe Asn Ser Ala Ser Leu Asn Arg
            135                 140                 145 cac ctt tct cgt gct tat gca agc aac atg ggt ggc tac aaa aat gag    535
His Leu Ser Arg Ala Tyr Ala Ser Asn Met Gly Gly Tyr Lys Asn Glu
        150                 155                 160 gga ttt gtt gag gtt ctt gct gct cag cag agt cct gag aat cct aat    583
Gly Phe Val Glu Val Leu Ala Ala Gln Gln Ser Pro Glu Asn Pro Asn
    165                 170                 175
```

```
tgg ttc cag ggt act gca gat gct gtg agg cag tat ttg tgg ctt ttt      631
Trp Phe Gln Gly Thr Ala Asp Ala Val Arg Gln Tyr Leu Trp Leu Phe
180                 185                 190                 195 gaa gag cac aat gtt ttg gaa ttc ttg gtt ctg gct ggt gac cat ttg      679
Glu Glu His Asn Val Leu Glu Phe Leu Val Leu Ala Gly Asp His Leu
                200                 205                 210 tat cga atg gat tac gag aaa ttt atc caa gcg cat agg gaa act gat      727
Tyr Arg Met Asp Tyr Glu Lys Phe Ile Gln Ala His Arg Glu Thr Asp
        215                 220                 225 gct gat atc act gtg gct gca ttg cca atg gat gaa gcg cgt gcc act      775
Ala Asp Ile Thr Val Ala Ala Leu Pro Met Asp Glu Ala Arg Ala Thr
    230                 235                 240 gca ttt ggt ttg atg aag att gat gaa gag ggg cgt ata att gaa ttt      823
Ala Phe Gly Leu Met Lys Ile Asp Glu Glu Gly Arg Ile Ile Glu Phe
245                 250                 255 gct gaa aag cca aaa gga gaa cag ttg aaa gct atg aag gtt gat act      871
Ala Glu Lys Pro Lys Gly Glu Gln Leu Lys Ala Met Lys Val Asp Thr
260                 265                 270                 275 aca att ttg ggt ctt gat gac gag aga gca aaa gaa atg cct tat att      919
Thr Ile Leu Gly Leu Asp Asp Glu Arg Ala Lys Glu Met Pro Tyr Ile
                280                 285                 290 gct agc atg ggt ata tat gtt gtt agc aaa aat gtg atg tta gac ctg      967
Ala Ser Met Gly Ile Tyr Val Val Ser Lys Asn Val Met Leu Asp Leu
        295                 300                 305 ctc cgt gag aag ttt cct ggt gca aat gac ttt ggg agt gaa gtg att     1015
Leu Arg Glu Lys Phe Pro Gly Ala Asn Asp Phe Gly Ser Glu Val Ile
    310                 315                 320 cct ggt gct act tct att gga atg aga gtg caa gct tac ttg tat gat     1063
Pro Gly Ala Thr Ser Ile Gly Met Arg Val Gln Ala Tyr Leu Tyr Asp
325                 330                 335 ggc tac tgg gaa gac att ggt aca atc gag gct ttc tat aat gca aat     1111
Gly Tyr Trp Glu Asp Ile Gly Thr Ile Glu Ala Phe Tyr Asn Ala Asn
340                 345                 350                 355 ctg gga atc acc aaa aag cct gtg cct gac ttc agt ttc tat gat cgt     1159
Leu Gly Ile Thr Lys Lys Pro Val Pro Asp Phe Ser Phe Tyr Asp Arg
                360                 365                 370 tca tct cca atc tac acc caa cca cga tat ttg cct ccc tct aag atg     1207
Ser Ser Pro Ile Tyr Thr Gln Pro Arg Tyr Leu Pro Pro Ser Lys Met
        375                 380                 385 ctt gat gct gat gtc act gat agt gtt att ggt gaa gga tgt gtg att     1255
Leu Asp Ala Asp Val Thr Asp Ser Val Ile Gly Glu Gly Cys Val Ile
    390                 395                 400 aag aac tgc aaa att cac cat tct gtg gtt ggg ctg cga tct tgc ata     1303
Lys Asn Cys Lys Ile His His Ser Val Val Gly Leu Arg Ser Cys Ile
405                 410                 415 tca gaa ggt gca att att gaa gac acg tta tta atg ggg gca gat tat     1351
Ser Glu Gly Ala Ile Ile Glu Asp Thr Leu Leu Met Gly Ala Asp Tyr
420                 425                 430                 435 tac gag acg gag gct gat aag agg ttt ctg gct gcc aaa ggc agt gtt     1399
Tyr Glu Thr Glu Ala Asp Lys Arg Phe Leu Ala Ala Lys Gly Ser Val
                440                 445                 450 cca att ggt ata ggc agg aac tct cat atc aaa agg gca att att gac     1447
Pro Ile Gly Ile Gly Arg Asn Ser His Ile Lys Arg Ala Ile Ile Asp
        455                 460                 465 aag aat gct cga att ggg gaa aat gtc aag att att aac agt gac aat     1495
Lys Asn Ala Arg Ile Gly Glu Asn Val Lys Ile Ile Asn Ser Asp Asn
    470                 475                 480 gtc caa gaa gct gca agg gaa aca gat ggg tat ttc ata aaa agt ggg     1543
Val Gln Glu Ala Ala Arg Glu Thr Asp Gly Tyr Phe Ile Lys Ser Gly
485                 490                 495
```

```
att gtc aca gta atc aag gat gct tta att cct agt gga aca gtc atc      1591
Ile Val Thr Val Ile Lys Asp Ala Leu Ile Pro Ser Gly Thr Val Ile
500                 505                 510                 515 taa acacaaccac ctccccaaaa aatttcttgt accccaaatc ctaatggtga            1644
ctgcgaagct cattaccacc gcaggagagt ttatcaagct ctgcttccac gtctaagata    1704
ggcttttgtg tttcatgata tatattttg ggcagtggct tgtaaataat agcggaagag     1764
aaggcccgct atgagcaatc acgctgtaaa gttcgttaat caattcaata aacaagttt     1824 ctttatttcg tactaaaaaa aaaaaaaaaa aa                                  1856

<210> SEQ ID NO 30
<211> LENGTH: 515
<212> TYPE: PRT
<213> ORGANISM: Glycine max

<400> SEQUENCE: 30

Met Ala Ser Met Ala Ala Ile Gly Ser Leu Asn Val Pro Arg Ser Ala
1               5                   10                  15

Ser Ser Arg Ser Ser Phe Val Gly Arg Lys Ser Val Pro Arg Ser Leu
            20                  25                  30

Ser Phe Ser Ala Ser Gln Leu Cys Gly Asp Lys Ile Pro Thr Asp Ser
        35                  40                  45

Val Leu Leu Ala Pro Lys Ile Gly Arg Ser Pro Val Ile Val Thr Pro
    50                  55                  60

Lys Ala Val Ser Asp Ser Gln Asn Ser Gln Thr Cys Leu Asp Pro Asp
65                  70                  75                  80

Ala Ser Arg Ser Val Leu Gly Ile Ile Leu Gly Gly Gly Ala Gly Thr
                85                  90                  95

Arg Leu Tyr Pro Leu Thr Lys Lys Arg Ala Lys Pro Ala Val Pro Leu
            100                 105                 110

Gly Ala Asn Tyr Arg Leu Ile Asp Ile Pro Val Ser Asn Cys Leu Asn
        115                 120                 125

Ser Asn Val Ser Lys Ile Tyr Val Leu Thr Gln Phe Asn Ser Ala Ser
    130                 135                 140

Leu Asn Arg His Leu Ser Arg Ala Tyr Ala Ser Asn Met Gly Gly Tyr
145                 150                 155                 160

Lys Asn Glu Gly Phe Val Glu Val Leu Ala Ala Gln Gln Ser Pro Glu
                165                 170                 175

Asn Pro Asn Trp Phe Gln Gly Thr Ala Asp Ala Val Arg Gln Tyr Leu
            180                 185                 190

Trp Leu Phe Glu Glu His Asn Val Leu Glu Phe Leu Val Leu Ala Gly
        195                 200                 205

Asp His Leu Tyr Arg Met Asp Tyr Glu Lys Phe Ile Gln Ala His Arg
    210                 215                 220

Glu Thr Asp Ala Asp Ile Thr Val Ala Ala Leu Pro Met Asp Glu Ala
225                 230                 235                 240

Arg Ala Thr Ala Phe Gly Leu Met Lys Ile Asp Glu Glu Gly Arg Ile
                245                 250                 255

Ile Glu Phe Ala Glu Lys Pro Lys Gly Glu Gln Leu Lys Ala Met Lys
            260                 265                 270

Val Asp Thr Thr Ile Leu Gly Leu Asp Asp Glu Arg Ala Lys Glu Met
        275                 280                 285

Pro Tyr Ile Ala Ser Met Gly Ile Tyr Val Val Ser Lys Asn Val Met
    290                 295                 300
```

-continued

Leu Asp Leu Arg Glu Lys Phe Pro Gly Ala Asn Asp Phe Gly Ser
305                 310                 315                 320

Glu Val Ile Pro Gly Ala Thr Ser Ile Gly Met Arg Val Gln Ala Tyr
            325                 330                 335

Leu Tyr Asp Gly Tyr Trp Glu Asp Ile Gly Thr Ile Glu Ala Phe Tyr
            340                 345                 350

Asn Ala Asn Leu Gly Ile Thr Lys Lys Pro Val Pro Asp Phe Ser Phe
            355                 360                 365

Tyr Asp Arg Ser Ser Pro Ile Tyr Thr Gln Pro Arg Tyr Leu Pro Pro
370                 375                 380

Ser Lys Met Leu Asp Ala Asp Val Thr Asp Ser Val Ile Gly Glu Gly
385                 390                 395                 400

Cys Val Ile Lys Asn Cys Lys Ile His His Ser Val Val Gly Leu Arg
            405                 410                 415

Ser Cys Ile Ser Glu Gly Ala Ile Ile Glu Asp Thr Leu Leu Met Gly
            420                 425                 430

Ala Asp Tyr Tyr Glu Thr Glu Ala Asp Lys Arg Phe Leu Ala Ala Lys
            435                 440                 445

Gly Ser Val Pro Ile Gly Ile Gly Arg Asn Ser His Ile Lys Arg Ala
            450                 455                 460

Ile Ile Asp Lys Asn Ala Arg Ile Gly Glu Asn Val Lys Ile Ile Asn
465                 470                 475                 480

Ser Asp Asn Val Gln Glu Ala Ala Arg Glu Thr Asp Gly Tyr Phe Ile
            485                 490                 495

Lys Ser Gly Ile Val Thr Val Ile Lys Asp Ala Leu Ile Pro Ser Gly
            500                 505                 510

Thr Val Ile
        515

<210> SEQ ID NO 31
<211> LENGTH: 515
<212> TYPE: PRT
<213> ORGANISM: Phaseolus vulgaris

<400> SEQUENCE: 31

Met Ala Ser Met Ala Ser Ile Gly Ser Leu Asn Val Pro Cys Ser Ser
1               5                   10                  15

Ser Ser Ser Ser Ser Asn Gly Gly Arg Lys Ile Leu Pro Arg Ala Leu
                20                  25                  30

Ser Phe Ser Ala Ser Gln Leu Tyr Gly Asp Lys Ile Ser Thr Asp Ser
            35                  40                  45

Val Ser Val Ala Pro Lys Arg Val Arg Asn Pro Val Val Ser Pro
    50                  55                  60

Lys Ala Val Ser Asp Ser Gln Asn Ser Gln Thr Cys Leu Asp Pro Asp
65                  70                  75                  80

Ala Ser Lys Ser Val Leu Gly Ile Ile Leu Gly Gly Ala Gly Thr
            85                  90                  95

Arg Leu Tyr Pro Leu Thr Lys Lys Arg Ala Lys Pro Ala Val Pro Leu
                100                 105                 110

Gly Ala Asn Tyr Arg Leu Ile Asp Ile Pro Val Ser Asn Cys Leu Asn
            115                 120                 125

Ser Asn Val Ser Lys Ile Tyr Val Leu Thr Gln Phe Asn Ser Ala Ser
        130                 135                 140

Leu Asn Arg His Leu Ser Arg Ala Tyr Ala Ser Asn Met Gly Gly Tyr

```
            145                 150                 155                 160
Lys Asn Glu Gly Phe Val Glu Val Leu Ala Ala Gln Gln Ser Pro Glu
                165                 170                 175

Asn Pro Asn Trp Phe Gln Gly Thr Ala Asp Ala Val Arg Gln Tyr Leu
            180                 185                 190

Trp Leu Phe Glu Glu His Asn Val Leu Glu Tyr Leu Val Leu Ala Gly
        195                 200                 205

Asp His Leu Tyr Arg Met Asp Tyr Glu Lys Phe Ile Gln Val His Arg
    210                 215                 220

Glu Ser Asp Ala Asp Ile Thr Val Ala Ala Leu Pro Met Asp Glu Asn
225                 230                 235                 240

Arg Ala Thr Ala Phe Gly Leu Met Lys Ile Asp Glu Glu Gly Arg Ile
                245                 250                 255

Ile Glu Phe Ala Glu Lys Pro Lys Gly Glu Gln Leu Lys Ala Met Lys
            260                 265                 270

Val Asp Thr Thr Ile Phe Gly Leu Asp Asp Glu Arg Ala Lys Glu Met
        275                 280                 285

Pro Tyr Ile Ala Ser Met Gly Ile Tyr Val Val Ser Lys Asn Val Met
    290                 295                 300

Leu Asn Leu Leu Arg Glu Lys Phe Pro Ala Ala Asn Asp Phe Gly Ser
305                 310                 315                 320

Glu Val Ile Pro Gly Ala Thr Ser Ile Gly Leu Arg Val Gln Ala Tyr
                325                 330                 335

Leu Tyr Asp Gly Tyr Trp Glu Asp Ile Gly Thr Ile Glu Ala Phe Tyr
            340                 345                 350

Asn Ala Asn Leu Gly Ile Thr Lys Lys Pro Val Pro Asp Phe Ser Phe
        355                 360                 365

Tyr Gly Arg Ser Ser Pro Ile Tyr Thr Gln Pro Arg Tyr Leu Pro Pro
    370                 375                 380

Ser Lys Met Leu Asp Ala Asp Val Thr Asp Ser Val Ile Gly Glu Gly
385                 390                 395                 400

Cys Val Ile Lys Asn Cys Lys Ile His His Ser Val Val Gly Leu Arg
                405                 410                 415

Ser Cys Ile Ser Glu Gly Ala Ile Ile Glu Asp Thr Leu Leu Met Gly
            420                 425                 430

Ala Asp Tyr Tyr Glu Thr Asp Ala Asp Lys Arg Phe Leu Ala Ala Lys
        435                 440                 445

Gly Ser Val Pro Ile Gly Ile Gly Arg Asn Ser His Val Lys Arg Ala
    450                 455                 460

Ile Ile Asp Lys Asn Ala Arg Ile Gly Glu Asn Val Lys Ile Leu Asn
465                 470                 475                 480

Ser Asp Asn Val Gln Glu Ala Ala Arg Glu Thr Asp Gly Tyr Phe Ile
                485                 490                 495

Lys Ser Gly Ile Val Thr Val Ile Lys Asp Ala Leu Ile Pro Ser Gly
            500                 505                 510

Thr Val Ile
        515

<210> SEQ ID NO 32
<211> LENGTH: 515
<212> TYPE: PRT
<213> ORGANISM: Glycine max

<400> SEQUENCE: 32
```

-continued

```
Met Ala Ser Met Ala Ala Ile Gly Ser Leu Asn Val Pro Arg Ser Ala
1               5                   10                  15

Ser Ser Arg Ser Ser Phe Val Gly Arg Lys Ser Val Pro Arg Ser Leu
            20                  25                  30

Ser Phe Ser Ala Ser Gln Leu Cys Gly Asp Lys Ile Pro Thr Asp Ser
        35                  40                  45

Val Leu Leu Ala Pro Lys Ile Gly Arg Ser Pro Val Ile Val Thr Pro
    50                  55                  60

Lys Ala Val Ser Asp Ser Gln Asn Ser Gln Thr Cys Leu Asp Pro Asp
65              70                  75                  80

Ala Ser Arg Ser Val Leu Gly Ile Ile Leu Gly Gly Ala Gly Thr
                85                  90                  95

Arg Leu Tyr Pro Leu Thr Lys Lys Arg Ala Lys Pro Ala Val Pro Leu
                100                 105                 110

Gly Ala Asn Tyr Arg Leu Ile Asp Ile Pro Val Ser Asn Cys Leu Asn
            115                 120                 125

Ser Asn Val Ser Lys Ile Tyr Val Leu Thr Gln Phe Asn Ser Ala Ser
        130                 135                 140

Leu Asn Arg His Leu Ser Arg Ala Tyr Ala Ser Asn Met Gly Gly Tyr
145                 150                 155                 160

Lys Asn Glu Gly Phe Val Glu Val Leu Ala Ala Gln Ser Pro Glu
                165                 170                 175

Asn Pro Asn Trp Phe Gln Gly Thr Ala Asp Ala Val Arg Gln Tyr Leu
            180                 185                 190

Trp Leu Phe Glu Glu His Asn Val Leu Glu Phe Leu Val Leu Ala Gly
        195                 200                 205

Asp His Leu Tyr Arg Met Asp Tyr Glu Lys Phe Ile Gln Ala His Arg
    210                 215                 220

Glu Thr Asp Ala Asp Ile Thr Val Ala Ala Leu Pro Met Asp Glu Ala
225                 230                 235                 240

Arg Ala Thr Ala Phe Gly Leu Met Lys Ile Asp Glu Glu Gly Arg Ile
                245                 250                 255

Ile Glu Phe Ala Glu Lys Pro Lys Gly Glu Gln Leu Lys Ala Met Lys
            260                 265                 270

Val Asp Thr Thr Ile Leu Gly Leu Asp Asp Glu Arg Ala Lys Glu Met
        275                 280                 285

Pro Tyr Ile Ala Ser Met Gly Ile Tyr Val Val Ser Lys Asn Val Met
    290                 295                 300

Leu Asp Leu Leu Arg Glu Lys Phe Pro Gly Ala Asn Asp Phe Gly Ser
305                 310                 315                 320

Glu Val Ile Pro Gly Ala Thr Ser Ile Gly Met Arg Val Gln Ala Tyr
                325                 330                 335

Leu Tyr Asp Gly Tyr Trp Glu Asp Ile Gly Thr Ile Glu Ala Phe Tyr
            340                 345                 350

Asn Ala Asn Leu Gly Ile Thr Lys Lys Pro Val Pro Asp Phe Ser Phe
        355                 360                 365

Tyr Asp Arg Ser Ser Pro Ile Tyr Thr Gln Pro Arg Tyr Leu Pro Pro
    370                 375                 380

Ser Lys Met Leu Asp Ala Asp Val Thr Asp Ser Val Ile Gly Glu Gly
385                 390                 395                 400

Cys Val Ile Lys Asn Cys Lys Ile His His Ser Val Val Gly Leu Arg
                405                 410                 415

Ser Cys Ile Ser Glu Gly Ala Ile Ile Glu Asp Thr Leu Leu Met Gly
```

```
                      420                 425                 430
Ala Asp Tyr Tyr Glu Thr Glu Ala Asp Lys Arg Phe Leu Ala Ala Lys
            435                 440                 445

Gly Ser Val Pro Ile Gly Ile Gly Arg Asn Ser His Ile Lys Arg Ala
    450                 455                 460

Ile Ile Asp Lys Asn Ala Arg Ile Gly Glu Asn Val Lys Ile Ile Asn
465                 470                 475                 480

Ser Asp Asn Val Gln Glu Ala Ala Arg Glu Thr Asp Gly Tyr Phe Ile
                485                 490                 495

Lys Ser Gly Ile Val Thr Val Ile Lys Asp Ala Leu Ile Pro Ser Gly
            500                 505                 510

Thr Val Ile
    515
```

PLASTIDIC PHOSPHOGLUCOMUTASE GENES

This application is a Continuation-in-Part and claims the benefit of U.S. patent application Ser. No. 09/906,209, filed Jul. 16, 2001, now U.S. Pat. No. 7,250,557, issued Jul. 31, 2007, and U.S. Provisional Application No. 60/218,712, filed Jul. 17, 2000, now expired, the entire contents of both are herein incorporated by reference.

FIELD OF THE INVENTION

This invention is in the field of plant molecular biology. More specifically, this invention pertains to isolated nucleic acid fragments encoding plastidic phosphoglucomutase proteins in plants and seeds and the use of such fragments to modulate expression of a gene encoding plastidic phosphoglucomutase activity.

BACKGROUND OF THE INVENTION

Starch synthesis occurs in the chloroplast while soluble carbohydrate (i.e., sucrose) synthesis occurs in the cytosol. These biosynthetic pathways are competing processes because excess triose phosphate can be used for either starch synthesis in the chloroplast or sucrose synthesis in the cytosol. These pathways have many common steps, however, the enzymes that catalyze similar steps are unique to each compartment. These enzymes are isozymes; different forms of the enzymes that catalyze the same reaction. For example, the plastidic and cytosolic forms of phosphoglucomutase both catalyze the conversion of glucose-6-phosphate to glucose 1-phosphate in different subcellular locations.

At maturity, about 40% of soybean seed dry weight is protein and 20% extractable oil. These constitute the economically valuable products of the soybean crop. Of the remaining 40% of seed weight, about 10% is soluble carbohydrate. The soluble carbohydrate portion contributes little to the economic value of soybean seeds and the main component of the soluble carbohydrate fraction, raffinosaccharides, are deleterious both to processing and to the food value of soybean meal in monogastric animals (Coon et al., (1988) Proceedings Soybean Utilization Alternatives, Univ. of Minnesota, pp. 203-211).

It may be possible to modulate the size of the starch and soluble carbohydrate pools in plant cells by altering the catalytic activity of specific enzymes in the starch and soluble carbohydrate biosynthetic pathways, such as phosphoglucomutase or one or both of the large and small subunits of ADP-glucose pyrophosphorylase (Taiz L., et al. *Plant Physiology;* The Benjamin/Cummings Publishing Company: New York, 1991). For example, during soybean seed maturation a large portion of the glucose which is converted to soluble carbohydrates (sucrose, raffinose and stachyose) during soybean seed maturation comes from the break down of a starch pool which was produced slowly during the primary growth phase. Elimination of this transient starch pool may be a strategy for diverting carbon away from the soluble carbohydrate components of dry soybean seeds (sucrose, raffinose and stachyose) and into the more economically desirable components such as oil and protein. This strategy may also be applicable to other plants such as corn, rice and wheat. Elimination of ADP-glucose pyrophosphorylase expression in developing maize embryos may decrease the production of transient starch in that tissue and lead to a concomitant increase in the oil content of the embryo [Singletary, G et al. (2001) U.S. Pat. No. 6,232,529].

There is a great deal of interest in identifying the genes that encode proteins involved in starch and soluble carbohydrate biosynthesis in plants. The genes that code for these enzymes may be used to study the interactions among individuals of the pathways and develop methods to alter starch and soluble carbohydrate biosynthesis. Accordingly, the availability of nucleic acid sequences encoding all or a substantial portion of a plastidic or cytosolic phosphoglucomutase (PGM) enzyme would facilitate studies to better understand starch and soluble carbohydrate biosynthesis in plants and provide genetic tools to enhance or otherwise alter starch and soluble carbohydrate biosynthesis.

Previous reports on a plastidic PGM mutant (pgm-1) from the oilseed plant *Arabidopsis* (Caspar et al. (1985) *Plant Physiol.* 79:11-17; Periappuram et al., (2000) *Plant Physiol.* 122:1193-1199) indicated that pgm-1 mutant plants showed a decrease in seed lipid content and an increase in leaf soluble carbohydrates. High levels of soluble carbohydrates were also observed in starchless *Nicotiana sylvestris* plants deficient in the plastidic PGM activity (Huber and Hanson, (1992) *Plant Physiol.* 99:1449-1454). Yet another effect of reduced starch content on carbon partitioning was observed in pea (*Pisum sativum*). Seeds from wild type pea typically contain 60% of the seed dry weight as starch. The rug3 locus of *Pisum sativum* encodes the pea plastidic phosphoglucomutase. Pea seeds, of the rug3rug3 genotype, substantially lacking plastidic phosphoglucomutase activity, have a wrinkled phenotype, higher levels of sucrose and an increased lipid content at maturity (EP 1001029A1; Casey et al., (1998) *J. Plant Physiol.* 152: 636-640).

SUMMARY OF THE INVENTION

In a first embodiment, the present invention concerns an isolated polynucleotide comprising: (a) a first nucleotide sequence encoding a first polypeptide comprising at least 560 amino acids, wherein the amino acid sequence of the first polypeptide and the amino acid sequence of SEQ ID NO:8 have at least 95%, 96%, 97%, 98%, 99% or 100% sequence identity, based on the Clustal V method of alignment, (b) a second nucleotide sequence encoding a second polypeptide comprising at least 560 amino acids, wherein the amino acid sequence of the second polypeptide and the amino acid sequence of SEQ ID NO:2, SEQ ID NO:4, or SEQ ID NO:10 have at least 85%, 90%, 95%, 96%, 97%, 98%, 99% or 100% sequence identity, based on the Clustal V method of alignment, or (c) the complement of the first or second nucleotide sequence, wherein the complement and the first or second nucleotide sequence contain the same number of nucleotides and are 100% complementary. The first polypeptide preferably comprises the amino acid sequence of SEQ ID NO:8, and the second polypeptide preferably comprises the amino acid sequence of SEQ ID NO:2, SEQ ID NO:4, or SEQ ID NO:10. The first nucleotide sequence preferably comprises the nucleotide sequence of SEQ ID NO:7, the second nucleotide sequence preferably comprises the nucleotide sequence of SEQ ID NO:1, SEQ ID NO:3, or SEQ ID NO:9. The first and second polypeptides preferably have phosphoglucomutase activity.

In a second embodiment, the present invention relates to a recombinant DNA construct comprising any of the isolated polynucleotides of the present invention operably linked to at least one regulatory sequence.

In a third embodiment, the present invention relates to a vector comprising any of the isolated polynucleotides of the present invention.

In a fourth embodiment, the present invention relates to an isolated polynucleotide fragment comprising a nucleotide sequence comprised by any of the polynucleotides of the present invention, wherein the nucleotide sequence contains at least 30, 40, 60, 100, 200, 300, 400, 500 or 541 nucleotides.

In a fifth embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In a sixth embodiment, the invention concerns a method for transforming a cell, comprising transforming a cell with a polynucleotide of the present invention.

In a seventh embodiment, the present invention relates to a method for producing a transgenic plant comprising transforming a plant cell with any of the isolated polynucleotides of the present invention and regenerating a transgenic plant from the transformed plant cell.

In an eighth embodiment, the invention concerns a cell, plant, or seed comprising a recombinant DNA construct of the present invention.

In a ninth embodiment, the present invention concerns an isolated polypeptide comprising: (a) a first amino acid sequence comprising at least 560 amino acids, wherein the first amino acid sequence and the amino acid sequence of SEQ ID NO:8 have at least 95%, 96%, 97%, 98%, 99% or 100% sequence identity, based on the Clustal V method of alignment, and (b) a second amino acid sequence comprising at least 560 amino acids, wherein the second amino acid sequence and the amino acid sequence of SEQ ID NO:2, SEQ ID NO:4, or SEQ ID NO:10 have at least 85%, 90%, 95%, 96%, 97%, 98%, 99% or 100% sequence identity, based on the Clustal V method of alignment. The first amino acid sequence preferably comprises the amino acid sequence of SEQ ID NO:8, and the second amino acid sequence preferably comprises the amino acid sequence SEQ ID NO:2, SEQ ID NO:4, or SEQ ID NO:10. The polypeptide preferably has phosphoglucomutase activity.

In a tenth embodiment, the present invention relates to a virus, preferably a baculovirus, comprising any of the isolated polynucleotides of the present invention or any of the recombinant DNA constructs of the present invention.

In an eleventh embodiment, the invention relates to a method of selecting an isolated polynucleotide that alters, i.e., increases or decreases, the level of expression of a phosphoglucomutase gene, protein or enzyme activity in a host cell, preferably a plant cell, the method comprising the steps of: (a) constructing an isolated polynucleotide of the present invention or an isolated recombinant DNA construct of the present invention; (b) introducing the isolated polynucleotide or the isolated recombinant DNA construct into a host cell; (c) measuring the level of the phosphoglucomutase RNA, protein or enzyme activity in the host cell containing the isolated polynucleotide or recombinant DNA construct; (d) comparing the level of the phosphoglucomutase RNA, protein or enzyme activity in the host cell containing the isolated polynucleotide or recombinant DNA construct with the level of the phosphoglucomutase RNA, protein or enzyme activity in a host cell that does not contain the isolated polynucleotide or recombinant DNA construct, and selecting the isolated polynucleotide or recombinant DNA construct that alters, i.e., increases or decreases, the level of expression of the phosphoglucomutase gene, protein or enzyme activity in the plant cell.

In a twelfth embodiment, the invention concerns a method of obtaining a nucleic acid fragment encoding a substantial portion of a phosphoglucomutase protein, preferably a plant phosphoglucomutase protein, comprising the steps of: synthesizing an oligonucleotide primer comprising a nucleotide sequence of at least 30 contiguous nucleotides, preferably at least 40 contiguous nucleotides, more preferably at least 60 contiguous nucleotides derived from a nucleotide sequence selected from the group consisting of SEQ ID NOs:1, 3, 5, 7, and 9, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a phosphoglucomutase protein amino acid sequence.

In a thirteenth embodiment, the invention relates to a method of obtaining a nucleic acid fragment encoding all or a substantial portion of the amino acid sequence encoding a phosphoglucomutase protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a fourteenth embodiment, the invention concerns a method for positive selection of a transformed cell comprising: (a) transforming a host cell with the recombinant DNA construct of the present invention or an expression cassette of the present invention; and (b) growing the transformed host cell, preferably a plant cell, such as a monocot or a dicot, under conditions which allow expression of the phosphoglucomutase polynucleotide in an amount sufficient to complement a null mutant to provide a positive selection means.

In a fifteenth embodiment, this invention concerns a method for suppressing the level of expression of a gene encoding a plastidic polypeptide having phosphoglucomutase activity in a transgenic plant, wherein the method comprises:
(a) transforming a plant cell with a fragment of the isolated polynucleotide of the invention;
(b) regenerating a transgenic plant from the transformed plant cell of (a); and
(c) selecting a transgenic plant wherein the level of expression of a gene encoding a plastidic polypeptide having phosphoglucomutase activity has been suppressed.

Preferably, the gene encodes a plastidic polypeptide having phosphoglucomutase activity, and the plant is a soybean plant.

In a sixteenth embodiment, the invention concerns a method for producing transgenic seed, the method comprising:
(a) transforming a plant cell with the recombinant DNA construct of
    (i) all or part of the nucleotide sequence set forth in SEQ ID NO:7 or SEQ ID NO:15; or
    (ii) the complement of (i);
    wherein (i) or (ii) is useful in co-suppression or antisense suppression of endogenous phosphoglucomutase activity in a transgenic plant;
(b) regenerating a transgenic plant from the transformed plant cell of (a); and (c) selecting a transgenic plant that produces a transgenic seed having an increase in the combined oil and protein content of at least 1.6% and a decrease in the sucrose content of at least 25% as compared to seed obtained from a non-transgenic plant.

Preferably, the seed is a soybean seed.

In a seventeenth embodiment, the invention concerns a method method for producing transgenic seed, the method comprising:
(a) transforming a plant cell with a recombinant DNA construct comprising
  (i) all or part of the nucleotide sequence set forth in SEQ ID NO:7 or SEQ ID NO:15; or
  (ii) the complement of (i);
  wherein (i) or (ii) is useful in co-suppression or antisense suppression of endogenous phosphoglucomutase activity in a transgenic plant;
(b) regenerating a transgenic plant from the transformed plant cell of (a); and
(c) selecting a transgenic plant that produces a transgenic seed having a sucrose to raffinose family oligosaccharide ratio of 1.0 or less as compared to seed obtained from a non-transgenic plant.

Preferably, the transgenic seed differs from an untransformed seed by having an increase in the combined oil and protein content of at least 1.6%, 1.8% or 2.0%. Preferably, the seed is a soybean seed.

In an eighteenth embodiment, the invention concerns a method for producing defatted meal from transgenic seed, comprising:
(a) transforming a plant cell with a recombinant DNA construct comprising
  (i) all or part of the nucleotide sequence set forth in SEQ ID NO:7 or SEQ ID NO:15; or
  (ii) the complement of (i);
  wherein (i) or (ii) is useful in co-suppression or antisense suppression of endogenous phosphoglucomutase activity in a transgenic plant;
(b) regenerating a transgenic plant from the transformed plant cell of (a); and
(c) selecting a transgenic plant that produces a transgenic seed wherein said seed is processed into defatted meal having an increase in the combined oil and protein content of at least 5% and a decrease in the sucrose content of at least 25% as compared to defatted meal obtained from seed of a non-transgenic plant.

Preferably, the defatted meal of the transgenic seed differs from the defatted meal of an untransformed seed by having a sucrose to raffinose family oligosaccharide ratio of 1.0 or less. Preferably, the seed is a soybean seed.

In a nineteenth embodiment, the invention concerns a transgenic seed that differs from an non-transgenic seed by having an increase in the combined oil and protein content of at least 1.6%, 1.8% or 2.0%, and a decrease in the sucrose content of at least 25%. Preferably, the seed is a soybean seed.

In a twentieth embodiment, the invention concerns a transgenic seed that differs from non-transgenic seed by having a sucrose to raffinose family oligosaccharide ratio of 1.0 or less. Preferably, the transgenic seed differs from an untransformed seed by having an increase in the combined oil and protein content of at least 1.6%, 1.8% or 2.0%. Preferably, the seed is a soybean seed.

In a twenty-first embodiment, the invention concerns a transgenic seed comprising a recombinant construct comprising (i) all or part of the nucleotide sequence set forth in SEQ ID NO:7 or SEQ ID NO:15; or
  (ii) the complement of (i);
  wherein (i) or (ii) is useful in co-suppression or antisense suppression of endogenous phosphoglucomutase activity in a transgenic plant;

further wherein said transgenic seed is processed to make defatted meal having an increase in the combined oil and protein content of at least 5% and a decrease in the sucrose content of at least 25% when compared to defatted meal obtained from a non-transgenic seed.

Preferably, the defatted meal of the transgenic seed differs from the defatted meal of an untransformed seed by having a sucrose to raffinose family oligosaccharide ratio of 1.0 or less. Preferably, the seed is a soybean seed.

In a twenty-second embodiment, the invention concerns a recombinant DNA construct comprising: (a) all or part of the nucleotide sequence set forth in SEQ ID NO:7 or SEQ ID NO:15; or (b) the complement of (a); wherein (a) or (b) is useful in co-suppression or antisense suppression of endogenous phosphoglucomutase activity in a transgenic plant.

BRIEF DESCRIPTION OF THE FIGURES AND SEQUENCE LISTING

The invention can be more fully understood from the following detailed description and the accompanying Drawing and Sequence Listing which form a part of this application.

FIGS. 1A-1D show an alignment of the amino acid sequences of plastidic phosphoglucomutase encoded by the nucleotide sequences derived from the following: cattail clone etr1c.pk005.f8 (SEQ ID NO:2); corn contig (SEQ ID NO:4) composed of p0075.cslaf22f (EST), p0075.cslaf22rb (EST), and p0128.cpicz81r (EST); soybean contig (SEQ ID NO:8) composed of clone sdp3c.pk003.e22 and PCR fragments; rice clone rdi1c.pk001.a22 (SEQ ID NO:10); plastidic phosphoglucomutase from *Brassica napus* (NCBI General Identifier No. 6272125; SEQ ID NO:11); plastidic phosphoglucomutase from *Pisum sativum* (NCBI General Identifier No. 6272283; SEQ ID NO:12); and plastidic phosphoglucomutase from *Pisum sativum* described in European Patent Application EP 1001029-A (NCBI General Identifier No. 10190529; SEQ ID NO:13). For the consensus alignment, amino acids which are conserved among all sequences at a given position, and which are contained in at least two sequences, are indicated with an asterisk (*). Dashes are used by the program to maximize alignment of the sequences. Amino acid positions for a given SEQ ID NO are given to the left of the corresponding line of sequence. Amino acid positions for the consensus alignment are given below each section of sequence.

FIG. 2 shows the starch accumulation expressed as mg/g fresh weight (top) and mg/seed (bottom) in plastidic PGM-silenced seeds (ko) as compared to wild-type seeds (wt).

FIG. 3 shows the soluble carbohydrate concentrations of growth chamber (GC) or field grown (field) T2 seeds from plastidic PGM-silenced events (KO) as compared to their null segregants (WT).

FIG. 4 shows soluble carbohydrate concentrations of T3 seeds from plastidic PGM-silenced events as compared to wild-type. PGM-silenced seeds with a 92B91 genetic background were compared to a 92B91 null event, while PGM-silenced seeds with a Jack background were compared to a Jack null event.

FIG. 5 shows the soluble carbohydrate profile of defatted soybean meal from T2 seeds.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire or functional protein derived from an FIS, a contig, an EST and PCR, or an FIS and PCR ("CGS"). Nucleotide SEQ ID NOs:1, 3, 5, and 7 correspond to nucleotide SEQ ID NOs:1, 3, 5, and 7, respectively, presented in U.S. Provisional Application No. 60/218,712, filed Jul. 17, 2000. Amino acid SEQ ID NOs:2, 4, 6, and 8 correspond to amino acid SEQ ID NOs:2, 4, 6, and 8, respectively, presented in U.S. Provisional Application No. 60/218,712, filed Jul. 17, 2000. The sequence descriptions and Sequence Listing attached hereto comply with the rules governing nucleotide and/or amino acid sequence disclosures in patent applications as set forth in 37 C.F.R. §1.821-1.825.

TABLE 1

Plastidic Phosphoglucomutase Proteins

| Protein (Plant Source) | Clone Designation | Status | SEQ ID NO: Nucleotide | SEQ ID NO: Amino Acid |
|---|---|---|---|---|
| Plastidic Phosphoglucomutase (Cattail) | etr1c.pk005.f8 (FIS) | CGS | 1 | 2 |
| Plastidic Phosphoglucomutase (Corn) | Contig Composed of: p0075.cslaf22f (EST); p0075.cslaf22rb (EST); p0128.cpicz81r (EST) | CGS | 3 | 4 |
| Plastidic Phosphoglucomutase (Rice) | rth1c.pk009.k14.f (EST) | EST | 5 | 6 |
| Plastidic Phosphoglucomutase (Soybean) | Contig Composed of: sdp3c.pk003.e22 (EST); PCR Fragments | CGS | 7 | 8 |
| Plastidic Phosphoglucomutase (Rice) | rdi1c.pk001.a22 (FIS) | CGS | 9 | 10 |

SEQ ID NO:10 corresponds to a direct translation of the nucleotide sequence for the full insert of rice clone rdi1c.pk001.a22. The amino acid sequence in SEQ ID NO:10 includes a 46 amino acid open-reading frame directly in front of, and in frame with, the methionine start codon.

SEQ ID NO:11 corresponds to plastidic phosphoglucomutase from Brassica napus (NCBI General Identifier No. 6272125).

SEQ ID NO:12 corresponds to plastidic phosphoglucomutase from Pisum sativum (NCBI General Identifier No. 6272283).

SEQ ID NO:13 corresponds to and plastidic phosphoglucomutase from Pisum sativum described in European Patent Application EP 1001029-A (NCBI General Identifier No. 10190529).

SEQ ID NO:14 corresponds to a 574 nucleotide NotI fragment from plasmid pTC103; this fragment contains a 541 nucleotide region of soybean plastidic phosphoglucomutase, a 19 nucleotide artificial sequence at the 5' end and a 14 nucleotide artificial sequence at the 3' end.

SEQ ID NO:15 corresponds to the 541 nucleotide region of soybean plastidic phosphoglucomutase contained in SEQ ID NO:14.

SEQ ID NO:16 corresponds to the full-insert sequence (FIS) of corn clone p0075.cslaf22rb.

SEQ ID NO:17 corresponds to the nucleotide sequence of plasmid pKS133.

SEQ ID NO:18 corresponds to a synthetic DNA linker.

SEQ ID NO:19 corresponds to synthetic complementary region of pKS106 and pKS124.

SEQ ID NO:20 corresponds to a synthetic complementary region of pKS133.

SEQ ID NO:21 corresponds to a synthetic PCR primer.

SEQ ID NO:22 corresponds to a synthetic PCR primer.

SEQ ID NO:23 corresponds to a nucleotide sequence of a contig made from the full-insert sequences of the cDNA inserts of soybean clones ses4d.pk0018.d10 and sdp2c.pk008.m2. The first 107 nucleotides of the contig were obtained from the sequence of clone ses4d.pk0018.d10.

SEQ ID NO:24 corresponds to the amino acid sequence of a large subunit polypeptide of soybean ADP-glucose pyrophosphorylase, and is encoded by nucleotides 42-1637 of SEQ ID NO:23.

SEQ ID NO:25 corresponds to the amino acid sequence of the large subunit of ADP-glucose pyrophosphorylase from chickpea, Cicer arietinum (NCBI General Identifier No. 13487785).

SEQ ID NO:26 corresponds to the amino acid sequence of SEQ ID NO:248406 from U.S. patent application US2004031072.

SEQ ID NO:27 corresponds to a nucleotide sequence obtained from the full-length sequence of the cDNA insert of soybean clone ssm.pk0072.e7:fis.

SEQ ID NO:28 corresponds to the amino acid sequence of a first small subunit polypeptide, SS1, of the soybean ADP-glucose pyrophosphorylase, and is encoded by nucleotides 80-1627 of SEQ ID NO:27.

SEQ ID NO:29 corresponds to a nucleotide sequence of a contig made from the EST sequence of soybean clone ssI.pk0021.h3 and the full-insert sequence of soybean clone sgs4c.pk005.b10. The first 58 nucleotides of the contig were obtained from the sequence of clone ssI.pk0021.h3.

SEQ ID NO:30 corresponds to the amino acid sequence of a second small subunit polypeptide, SS2, of the soybean ADP-glucose pyrophosphorylase, and is encoded by nucleotides 47-1594 of SEQ ID NO:29.

SEQ ID NO:31 corresponds to the amino acid sequence of the small subunit, PvAGPS1, of ADP-glucose pyrophosphorylase from Phaseolus vulgaris (NCBI General Identifier No. 29421116).

SEQ ID NO:32 corresponds to the amino acid sequence of SEQ ID NO:251944 from U.S. Patent Application US2004031072.

The Sequence Listing contains the one letter code for nucleotide sequence characters and the three letter codes for amino acids as defined in conformity with the IUPAC-IUBMB standards described in Nucleic Acids Res. 13:3021-3030 (1985) and in the Biochemical J. 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

All patents, patent applications, and publications cited throughout the application are hereby incorporated by reference in their entirety.

In the context of this disclosure, a number of terms shall be utilized.

The term "raffinose family oligosaccharides" (RFOs) indicates a group of D-galactose containing oligosaccharides that are synthesized by a set of galactosyltransferases. Raffinose family oligosaccharides are characterized by having the general formula: O-β-D-galactopyranosyl-$(1\rightarrow6)_n$-α-D-glucopyranosyl-$(1\rightarrow2)$-β-D-fructofuranoside, where oligosaccharides with n=1 through n=4 are known respectively as raffinose, stachyose, verbascose, and ajugose. Examples of raffinose family oligosaccharides include, but are not limited to, raffinose, stachyose, verbascose and ajugose.

The term "plant" includes reference to whole plants, plant parts or organs (e.g., leaves, stems, roots, etc.), plant cells, seeds and progeny of same. Plant cell, as used herein includes, without limitation, cells obtained from or found in the following: seeds, suspension cultures, embryos, meristematic regions, callus tissue, leaves, roots, shoots, gametophytes, sporophytes, pollen and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants.

Examples of monocots include, but are not limited to, corn, wheat, rice, sorghum, millet, barley, palm, lily, *Alstroemeria*, rye, and oat.

Examples of dicots include, but are not limited to, soybean, rape, sunflower, canola, grape, guayule, columbine, cotton, tobacco, peas, beans, flax, safflower, and alfalfa.

Plant tissue includes differentiated and undifferentiated tissues or plants, including but not limited to, roots, stems, shoots, leaves, pollen, seeds, tumor tissue, and various forms of cells and culture such as single cells, protoplasm, embryos, and callus tissue. The plant tissue may in plant or in organ, tissue or cell culture.

The term "plant organ" refers to plant tissue or group of tissues that constitute a morphologically and functionally distinct part of a plant. The term "genome" refers to the following: 1. The entire complement of genetic material (genes and non-coding sequences) is present in each cell of an organism, or virus or organelle. 2. A complete set of chromosomes inherited as a (haploid) unit from one parent. The term "stably integrated" refers to the transfer of a nucleic acid fragment into the genome of a host organism or cell resulting in genetically stable inheritance.

The terms "polynucleotide", "polynucleotide sequence", "nucleic acid", "nucleic acid sequence", and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" refers to materials, such as "isolated nucleic acid fragments" and/or "isolated polypeptides", which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "isolated nucleic acid fragment" is used interchangeably with "isolated polynucleotide" and is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of recombinant DNA constructs to produce the desired phenotype in a transformed plant. Recombinant DNA constructs can be designed for use in co-suppression or antisense by linking a nucleic acid fragment or subfragment thereof, whether or not it encodes an active enzyme, in the appropriate orientation relative to a plant promoter sequence.

"Cosuppression" refers to the production of sense RNA transcripts capable of suppressing the expression of identical or substantially similar native genes (U.S. Pat. No. 5,231,020). Cosuppression technology constitutes the subject matter of U.S. Pat. No. 5,231,020, which issued to Jorgensen et al. on Jul. 27, 1999. The phenomenon observed by Napoli et al. in petunia was referred to as "cosuppression" since expression of both the endogenous gene and the introduced transgene were suppressed (for reviews see Vaucheret et al., *Plant J.* 16:651-659 (1998); and Gura, *Nature* 404:804-808 (2000)).

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al. (1998) *Plant J* 16:651-659; and Gura (2000) *Nature* 404:804-808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). This increases the frequency of cosuppression in the recovered transgenic plants. Another variation describes the use of plant viral sequences to direct the suppression, or "silencing", of proximal mRNA encoding sequences (PCT Publication WO 98/36083 published on Aug. 20, 1998). Both of these co-suppressing phenomena have not been elucidated mechanistically, although recent genetic evidence has begun to unravel this complex situation (Elmayan et al. (1998) *Plant Cell* 10:1747-1757).

In addition to cosuppression, antisense technology has also been used to block the function of specific genes in cells. Antisense RNA is complementary to the normally expressed RNA, and presumably inhibits gene expression by interacting with the normal RNA strand. The mechanisms by which the expression of a specific gene are inhibited by either antisense or sense RNA are on their way to being understood. However, the frequencies of obtaining the desired phenotype in a transgenic plant may vary with the design of the construct, the gene, the strength and specificity of its promoter, the method of transformation and the complexity of transgene insertion events (Baulcombe, *Curr. Biol.* 12(3):R82-84 (2002); Tang et al., *Genes Dev.* 17(1): 49-63 (2003); Yu et al., *Plant Cell. Rep.* 22(3):167-174 (2003)). Cosuppression and antisense inhibition are also referred to as "gene silencing", "post-transcriptional gene silencing" (PTGS), RNA interference or RNAi. See for example U.S. Pat. No. 6,506,559.

MicroRNAs (miRNA) are small regulatory RNSs that control gene expression. miRNAs bind to regions of target RNAs and inhibit their translation and, thus, interfere with production of the polypeptide encoded by the target RNA. miRNAs can be designed to be complementary to any region of the target sequence RNA including the 3' untranslated region, coding region, etc. miRNAs are processed from highly structured RNA precursors that are processed by the action of a ribonuclease III termed DICER. While the exact mechanism of action of miRNAs is unknown, it appears that they function to regulate expression of the target gene. See, e.g., U.S. Patent Publication No. 2004/0268441 AI which was published on Dec. 30, 2004.

The term "expression", as used herein, refers to the production of a functional end-product, be it mRNA or translation of mRNA into a polypeptide. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Overexpression" refers to the production of a functional end-product in transgenic organisms that exceeds levels of production when compared to expression of that functional end-product in a normal, wild type or non-transformed organism.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is using particle-accelerated or "gene gun" transformation technology (Klein et al. (1987) *Nature* (London) 327:70-73; U.S. Pat. No. 4,945,050), or an *Agrobacterium*-mediated method (Ishida Y. et al. (1996) *Nature Biotech.* 14:745-750). The term "transformation" as used herein refers to both stable transformation and transient transformation.

"Antisense inhibition" refers to the production of antisense RNA transcripts capable of suppressing the expression of the target protein.

As stated herein, "suppression" refers to the reduction of the level of enzyme activity or protein functionality detectable in a transgenic plant when compared to the level of enzyme activity or protein functionality detectable in a plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to the decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in the desired cell.

"Gene silencing," as used herein, is a general term that refers to decreasing mRNA levels as compared to wild-type plants, does not specify mechanism and is inclusive, and not limited to, anti-sense, cosuppression, viral-suppression, hairpin suppression and stem-loop suppression.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. For example, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes that result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 1×SSC, 0.1% SDS, 60° C.) with the sequences exemplified herein, or to any portion of the nucleotide sequences reported herein and which are functionally equivalent to the gene or the promoter of the invention. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions involves the use of higher temperatures in which the washes are identical to those above except for the temperature of the final two 30 min washes in 0.2×SSC, 0.5% SDS was increased to 60° C. Another preferred set of highly stringent conditions involves the use of two final washes in 0.1×SSC, 0.1% SDS at 65° C.

With respect to the degree of substantial similarity between the target (endogenous) mRNA and the RNA region in the construct having homology to the target mRNA, such sequences should be at least 25 nucleotides in length, preferably at least 50 nucleotides in length, more preferably at least 100 nucleotides in length, again more preferably at least 200 nucleotides in length, and most preferably at least 300 nucleotides in length; and should be at least 80% identical, preferably at least 85% identical, more preferably at least 90% identical, and most preferably at least 95% identical.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein.

It is well understood by one skilled in the art that many levels of sequence identity are useful in identifying related polypeptide sequences. Useful examples of percent identities are 50%, 55%, 60%, 65%, 70%, 75%, 80%, 85%, 90%, or 95%, or any integer percentage from 55% to 100%.

Sequence alignments and percent similarity calculations may be determined using a variety of comparison methods designed to detect homologous sequences including, but not limited to, the Megalign program of the LASARGENE bioinformatics computing suite (DNASTAR Inc., Madison, Wis.). Unless stated otherwise, multiple alignment of the sequences provided herein were performed using the Clustal method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain a "percent identity" by viewing the "sequence distances" table on the same program.

Unless otherwise stated, "BLAST" sequence identity/similarity values provided herein refer to the value obtained using the BLAST 2.0 suite of programs using default parameters (Altschul et al., *Nucleic Acids Res.* 25:3389-3402 (1997)). Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

"Sequence identity" or "identity" in the context of nucleic acid or polypeptide sequences refers to the nucleic acid bases or amino acid residues in the two sequences that are the same when aligned for maximum correspondence over a specified comparison window.

Thus, "Percentage of sequence identity" refers to the valued determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 55% to 100%. These identities can be determined using any of the programs described herein.

Sequence alignments and percent identity or similarity calculations may be determined using a variety of comparison methods designed to detect homologous sequences including, but not limited to, the Megalign program of the LASARGENE bioinformatics computing suite (DNASTAR Inc., Madison, Wis.). Multiple alignment of the sequences are performed using the Clustal V method of alignment (Higgins, D. G. and Sharp, P. M. (1989) *Comput. Appl. Biosci.* 5:151-153; Higgins, D. G. et al. (1992) *Comput. Appl. Biosci.* 8:189-191) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

It is well understood by one skilled in the art that many levels of sequence identity are useful in identifying polypeptides, from other plant species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 55% to 100%. Indeed, any integer amino acid identity from 50%-100% may be useful in describing the present invention. Also, of interest is any full or partial complement of this isolated nucleotide fragment.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

The terms "synthetic nucleic acid" or "synthetic genes" refer to nucleic acid molecules assembled either in whole or in part from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that is capable of directing expression a specific protein or functional RNA.

"Native gene" refers to a gene as found in nature with its own regulatory sequences.

"Chimeric gene" or "recombinant DNA construct" are used interchangeably herein, and refers any gene that is not a native gene, comprising regulatory and coding sequences that are not found together in nature, or to an isolated native gene optionally modified and reintroduced into a host cell.

A chimeric gene may comprise regulatory sequences and coding sequences that are derived from different sources, or regulatory sequences and coding sequences derived from the same source, but arranged in a manner different than that found in nature. In one embodiment, a regulatory region and a coding sequence region are assembled from two different sources. In another embodiment, a regulatory region and a coding sequence region are derived from the same source but arranged in a manner different than that found in nature. In another embodiment, the coding sequence region is assembled from at least two different sources. In another embodiment, the coding region is assembled from the same source but in a manner not found in nature.

The term "endogenous gene" refers to a native gene in its natural location in the genome of an organism.

The term "foreign gene" refers to a gene not normally found in the host organism that is introduced into the host organism by gene transfer.

The term "transgene" refers to a gene that has been introduced into a host cell by a transformation procedure. Transgenes may become physically inserted into a genome of the host cell (e.g., through recombination) or may be maintained outside of a genome of the host cell (e.g., on an extrachromasomal array).

An "allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

The term "coding sequence" refers to a DNA fragment that codes for a polypeptide having a specific amino acid sequence, or a structural RNA. The boundaries of a protein coding sequence are generally determined by a ribosome binding site (prokaryotes) or by an ATG start codon (eukaryotes) located at the 5' end of the mRNA and a transcription terminator sequence located just downstream of the open reading frame at the 3' end of the mRNA. A coding sequence can include, but is not limited to, DNA, cDNA, and recombinant nucleic acid sequences.

"Mature" protein refers to a post-translationally processed polypeptide; i.e., one from which any pre- or pro-peptides present in the primary translation product have been removed. "Precursor" protein refers to the primary product of translation of mRNA; i.e., with pre- and pro-peptides still present. Pre- and pro-peptides may be and are not limited to intracellular localization signals.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Sense" RNA refers to RNA transcript that includes the mRNA and can be translated into protein within a cell or in vitro.

"Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence.

"Functional RNA" refers to antisense RNA, ribozyme RNA, or other RNA that may not be translated, yet has an effect on cellular processes. The terms "complement" and "reverse complement" are used interchangeably herein with respect to mRNA transcripts, and are meant to define the antisense RNA of the message.

The term "recombinant DNA construct" refers to a DNA construct assembled from nucleic acid fragments obtained from different sources. The types and origins of the nucleic acid fragments may be very diverse.

A "recombinant expression construct" contains a nucleic acid fragment operably linked to at least one regulatory element, that is capable of effecting expression of the nucleic acid fragment. The recombinant expression construct may also affect expression of a homologous sequence in a host cell.

In one embodiment the choice of recombinant expression construct is dependent upon the method that will be used to transform host cells. The skilled artisan is well aware of the genetic elements that must be present on the recombinant expression construct in order to successfully transform, select and propagate host cells. The skilled artisan will also recognize that different independent transformation events may be screened to obtain lines displaying the desired expression level and pattern. Such screening may be accomplished by, but is not limited to, Southern analysis of DNA, Northern analysis of mRNA expression, Western analysis of protein expression, or phenotypic analysis.

The term "operably linked" refers to the association of nucleic acid fragments on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

"Regulatory sequences" refer to nucleotides located upstream (5' non-coding sequences), within, or downstream (3' non-coding sequences) of a coding sequence, and which may influence the transcription, RNA processing, stability, or translation of the associated coding sequence. Regulatory sequences may include, and are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of an isolated nucleic acid fragment in different tissues or cell types, or at different stages of development, or in response to different environmental conditions. Promoters which cause an isolated nucleic acid fragment to be expressed in most cell types at most times are commonly referred to as "constitutive promoters". New promoters of various types useful in plant cells are constantly being discovered; numerous examples may be found in the compilation by Okamuro and Goldberg, (1989) Biochemistry of Plants 15:1-82. It is further recognized that since in most cases the exact boundaries of regulatory sequences have not been completely defined, DNA fragments of some variation may have identical promoter activity.

Specific examples of promoters that may be useful in expressing the nucleic acid fragments of the invention include, but are not limited to, the oleosin promoter (PCT Publication WO99/65479, published Dec. 12, 1999), the maize 27kD zein promoter (Ueda et al (1994) *Mol. Cell. Biol.* 14:4350-4359), the ubiquitin promoter (Christensen et al (1992) *Plant Mol. Biol.* 18:675-680), the SAM synthetase promoter (PCT Publication WO00/37662, published Jun. 29, 2000), the CaMV 35S (Odell et al (1985) *Nature* 313:810-812), and the promoter described in PCT Publication WO02/099063 published Dec. 12, 2002.

The "translation leader sequence" refers to a polynucleotide fragment located between the promoter of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Mol. Biotechnol.* 3:225-236).

An "intron" is an intervening sequence in a gene that does not encode a portion of the protein sequence. Thus, such sequences are transcribed into RNA but are then excised and are not translated. The term is also used for the excised RNA sequences.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) *Plant Cell* 1:671-680.

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, 1989. Transformation methods are well known to those skilled in the art and are described below.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

"Stable transformation" refers to the transfer of a nucleic acid fragment into a genome of a host organism, including nuclear and organellar genomes, resulting in genetically stable inheritance.

In contrast, "transient transformation" refers to the transfer of a nucleic acid fragment into the nucleus, or DNA-containing organelle, of a host organism resulting in gene expression without integration or stable inheritance.

Host organisms comprising the transformed nucleic acid fragments are referred to as "transgenic" organisms.

The term "amplified" means the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993). The product of amplification is termed an amplicon.

The term "chromosomal location" includes reference to a length of a chromosome which may be measured by reference to the linear segment of DNA which it comprises. The chromosomal location can be defined by reference to two unique DNA sequences, i.e., markers.

The term "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers.

The present invention includes, inter alia, compositions and methods for modulating (i.e., increasing or decreasing) the level of plastidic polypeptides described herein in plants. The size of the starch and soluble carbohydrate pools in soybean seeds can be modulated by altering the expression of a specific gene, encoding plastidic phosphoglucomutase (pPGM), which is involved in the starch and soluble carbohydrate biosynthetic pathway.

Silencing of pPGM gene expression in transgenic soybeans seeds resulted in a drastic decrease of the transient starch pool accompanied by a reduction in soluble carbohydrates and a concomitant increase in combined oil and protein content. Elimination of the transient starch pool by silencing plastidic PGM gene expression in soybean seeds diverted carbon away from the soluble carbohydrate components of dry soybean seeds with the major decrease occurring in the sucrose pool. This is in contrast to PGM mutants of pea, *Arabidopsis*, and *Nicotiana*, where the carbon is mainly funneled into the soluble carbohydrate pool.

The data discussed below further indicates that soybean seeds deficient in plastidic PGM reallocate the carbon destined for starch biosynthesis toward the biosynthesis oil and protein and also alters the sucrose to raffinose family oligosaccharide ratio.

In contrast, a 40% reduction in storage lipid content was observed in the Arabidopsis mutant pgm-1, which contains a point mutation in the AtPGM gene rendering the polypeptide nonfunctional (Periappuram et al., (2000) Plant Physiol. 122:1193-1199).

An alteration of plastidic PGM activity affects the allocation of carbon to the soluble carbohydrate pool as well as the allocation of carbon to oil and protein biosynthesis. This is accomplished with no adverse effect on plant and seed phenotype. Since all known soybean cultivars contain transient starch, silencing the plastidic PGM gene in any soybean cultivar should result in a decrease of the transient carbon reserve together with an increase in the combined oil and protein level. This increase in the combined oil and protein level is in addition to the oil and protein levels of the wild-type genotype, regardless of whether the level is low or high. For example, a soybean variety such as Sakaii-18 has 56% of its seed dry weight as protein and 14% as oil. A Pioneer soybean variety, 9306, contains 41% protein and 23% oil (as seed dry weight). Both genotypes would be expected to have an increase in the combined oil and protein content as well as altered sucrose to raffinose family oligosaccharide ratio.

In one embodiment, the present invention concerns an isolated polynucleotide comprising: (a) a first nucleotide sequence encoding a first polypeptide comprising at least 560 amino acids, wherein the amino acid sequence of the first polypeptide and the amino acid sequence of SEQ ID NO:8 have at least 95%, 96%, 97%, 98%, 99% or 100% sequence identity, based on the Clustal V method of alignment, (b) a second nucleotide sequence encoding a second polypeptide comprising at least 560 amino acids, wherein the amino acid sequence of the second polypeptide and the amino acid sequence of SEQ ID NO:2, SEQ ID NO:4, or SEQ ID NO:10 have at least 85%, 90%, 95%, 96%, 97%, 98%, 99% or 100% sequence identity, based on the Clustal V method of alignment, or (c) the complement of the first or second nucleotide sequence, wherein the complement and the first or second nucleotide sequence contain the same number of nucleotides and are 100% complementary. The first polypeptide preferably comprises the amino acid sequence of SEQ ID NO:8, and the second polypeptide preferably comprises the amino acid sequence of SEQ ID NO:2, SEQ ID NO:4, or SEQ ID NO:10. The first nucleotide sequence preferably comprises the nucleotide sequence of SEQ ID NO:7, the second nucleotide sequence preferably comprises the nucleotide sequence of SEQ ID NO:1, SEQ ID NO:3, or SEQ ID NO:9. The first and second polypeptides preferably have phosphoglucomutase activity.

In another embodiment, the present invention relates to a recombinant DNA construct comprising any of the isolated polynucleotides of the present invention operably linked to at least one regulatory sequence.

In another preferred embodiment of the present invention, a recombinant DNA construct of the present invention further comprises an enhancer.

In another embodiment, the present invention relates to a vector comprising any of the isolated polynucleotides of the present invention.

In another embodiment, the present invention relates to an isolated polynucleotide fragment comprising a nucleotide sequence comprised by any of the polynucleotides of the present invention, wherein the nucleotide sequence contains at least 30, 40, 60, 100, 200, 300, 400, 500 or 541 nucleotides.

In another embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In another embodiment, the present invention relates to a method for transforming a cell, comprising transforming a cell with a polynucleotide of the present invention.

In another embodiment, the present invention relates to a method for producing a transgenic plant comprising transforming a plant cell with any of the isolated polynucleotides of the present invention and regenerating a transgenic plant from the transformed plant cell.

In another embodiment, a cell, plant, or seed comprising a recombinant DNA construct of the present invention.

In another embodiment, the present invention concerns an isolated polypeptide comprising: (a) a first amino acid sequence comprising at least 560 amino acids, wherein the first amino acid sequence and the amino acid sequence of SEQ ID NO:8 have at least 95%, 96%, 97%, 98%, 99% or 100% sequence identity, based on the Clustal V method of alignment, and (b) a second amino acid sequence comprising at least 560 amino acids, wherein the second amino acid sequence and the amino acid sequence of SEQ ID NO:2, SEQ ID NO:4, or SEQ ID NO:10 have at least 85%, 90%, 95%, 96%, 97%, 98%, 99% or 100% sequence identity, based on the Clustal V method of alignment. The first amino acid sequence preferably comprises the amino acid sequence of SEQ ID NO:8, and the second amino acid sequence preferably comprises the amino acid sequence SEQ ID NO:2, SEQ ID NO:4, or SEQ ID NO:10. The polypeptide preferably has phosphoglucomutase activity.

In another embodiment, the present invention relates to a virus, preferably a baculovirus, comprising any of the isolated polynucleotides of the present invention or any of the recombinant DNA constructs of the present invention.

In another embodiment, the invention relates to a method of selecting an isolated polynucleotide that alters, i.e., increases or decreases, the level of expression of a phosphoglucomutase gene, protein or enzyme activity in a host cell, preferably a plant cell, the method comprising the steps of: (a) constructing an isolated polynucleotide of the present invention or an isolated recombinant DNA construct of the present invention; (b) introducing the isolated polynucleotide or the isolated recombinant DNA construct into a host cell; (c) measuring the level of the phosphoglucomutase RNA, protein or enzyme activity in the host cell containing the isolated polynucleotide or recombinant DNA construct; (d) comparing the level of the phosphoglucomutase RNA, protein or enzyme activity in the host cell containing the isolated polynucleotide or recombinant DNA construct with the level of the phosphoglucomutase RNA, protein or enzyme activity in a host cell that does not contain the isolated polynucleotide or recombinant DNA construct, and selecting the isolated polynucleotide or recombinant DNA construct that alters, i.e., increases or decreases, the level of expression of the phosphoglucomutase gene, protein or enzyme activity in the plant cell.

In another embodiment, the invention concerns a method of obtaining a nucleic acid fragment encoding a substantial portion of a phosphoglucomutase protein, preferably a plant phosphoglucomutase protein, comprising the steps of: synthesizing an oligonucleotide primer comprising a nucleotide sequence of at least 30 contiguous nucleotides, preferably at least 40 contiguous nucleotides, more preferably at least 60 contiguous nucleotides derived from a nucleotide sequence selected from the group consisting of SEQ ID NOs:1, 3, 5, 7, and 9, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a phosphoglucomutase protein amino acid sequence.

In another embodiment, the invention relates to a method of obtaining a nucleic acid fragment encoding all or a substantial portion of the amino acid sequence encoding a phosphoglucomutase protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In another embodiment, the invention concerns a method for positive selection of a transformed cell comprising: (a) transforming a host cell with the recombinant DNA construct of the present invention or an expression cassette of the present invention; and (b) growing the transformed host cell, preferably a plant cell, such as a monocot or a dicot, under conditions which allow expression of the phosphoglucomutase polynucleotide in an amount sufficient to complement a null mutant to provide a positive selection means.

In another embodiment, this invention concerns a method for suppressing the level of expression of a gene encoding a plastidic polypeptide having phosphoglucomutase activity in a transgenic plant, wherein the method comprises:
(a) transforming a plant cell with a fragment of the isolated polynucleotide of the invention;
(b) regenerating a transgenic plant from the transformed plant cell of (a); and
(c) selecting a transgenic plant wherein the level of expression of a gene encoding a plastidic polypeptide having phosphoglucomutase activity has been suppressed.

Preferably, the gene encodes a plastidic polypeptide having phosphoglucomutase activity, and the plant is a soybean plant.

In another embodiment, the invention concerns a recombinant DNA construct comprising: (a) all or part of the nucleotide sequence set forth in SEQ ID NO:7 or SEQ ID NO:15; or (b) the complement of (a); wherein (a) or (b) is useful in cosuppression or antisense suppression of endogenous phosphoglucomutase activity in a transgenic plant.

In another embodiment, the invention concerns a method for producing transgenic seed, the method comprising:
(a) transforming a plant cell with the recombinant DNA construct of
(i) all or part of the nucleotide sequence set forth in SEQ ID NO:7 or SEQ ID NO:15; or
(ii) the complement of (i);
wherein (i) or (ii) is useful in co-suppression or antisense suppression of endogenous phosphoglucomutase activity in a transgenic plant;
(b) regenerating a transgenic plant from the transformed plant cell of (a); and
(c) selecting a transgenic plant that produces a transgenic seed having an increase in the combined oil and protein content of at least 1.6% and a decrease in the sucrose content of at least 25% as compared to seed obtained from a non-transgenic plant. Preferably, the seed is a soybean seed.

In another embodiment, the invention concerns a method method for producing transgenic seed, the method comprising:
(a) transforming a plant cell with a recombinant DNA construct comprising
(i) all or part of the nucleotide sequence set forth in SEQ ID NO:7 or SEQ ID NO:15; or
(ii) the complement of (i);
wherein (i) or (ii) is useful in co-suppression or antisense suppression of endogenous phosphoglucomutase activity in a transgenic plant;
(b) regenerating a transgenic plant from the transformed plant cell of (a); and
(c) selecting a transgenic plant that produces a transgenic seed having a sucrose to raffinose family oligosaccharide ratio of 1.0 or less as compared to seed obtained from a non-transgenic plant.

Preferably, the transgenic seed differs from an untransformed seed by having an increase in the combined oil and protein content of at least 1.6%, 1.8% or 2.0%. Preferably, the seed is a soybean seed.

In another embodiment, the invention concerns a method for producing defatted meal from transgenic seed, comprising:
(a) transforming a plant cell with a recombinant DNA construct comprising (i) all or part of the nucleotide sequence set forth in SEQ ID NO:7 or SEQ ID NO:15; or
(ii) the complement of (i);
wherein (i) or (ii) is useful in co-suppression or antisense suppression of endogenous phosphoglucomutase activity in a transgenic plant;
(b) regenerating a transgenic plant from the transformed plant cell of (a); and
(c) selecting a transgenic plant that produces a transgenic seed wherein said seed is processed into defatted meal having an increase in the combined oil and protein content of at least 5% and a decrease in the sucrose content of at least 25% as compared to defatted meal obtained from seed of a non-transgenic plant.

Preferably, the defatted meal of the transgenic seed differs from the defatted meal of an untransformed seed by having a sucrose to raffinose family oligosaccharide ratio of 1.0 or less. Preferably, the seed is a soybean seed.

In a another embodiment, the invention concerns a transgenic seed that differs from an non-transgenic seed by having an increase in the combined oil and protein content of at least 1.6%, 1.8% or 2.0%, and a decrease in the sucrose content of at least 25%. Preferably, the seed is a soybean seed.

In another embodiment, the invention concerns a transgenic seed that differs from non-transgenic seed by having a sucrose to raffinose family oligosaccharide ratio of 1.0 or less. Preferably, the transgenic seed differs from an untransformed seed by having an increase in the combined oil and protein content of at least 1.6%, 1.8% or 2.0%. Preferably, the seed is a soybean seed.

In another embodiment, the invention concerns a transgenic seed comprising
a recombinant construct comprising (i) all or part of the nucleotide sequence set forth in SEQ ID NO:7 or SEQ ID NO:15; or (ii) the complement of (i);
wherein (i) or (ii) is useful in co-suppression or antisense suppression of endogenous phosphoglucomutase activity in a transgenic plant;
further wherein said transgenic seed is processed to make defatted meal having an increase in the combined oil and protein content of at least 5% and a decrease in the sucrose content of at least 25% when compared to defatted meal obtained from a non-transgenic seed.

Preferably, the defatted meal of the transgenic seed differs from the defatted meal of an untransformed seed by having a sucrose to raffinose family oligosaccharide ratio of 1.0 or less. Preferably, the seed is a soybean seed.

Soybeans can be processed into a number of products. For example, "soy protein products" can include, and are not limited to, those items listed in Table A. "Soy protein products".

TABLE A

Soy Protein Products Derived from Soybean Seeds[a]

| Processed Soy Protein Products | |
|---|---|
| Whole Soybean Products | |
| Roasted Soybeans | Full Fat and Defatted Flours |
| Baked Soybeans | Soy Grits |
| Soy Sprouts | Soy Hypocotyls |
| Soy Milk | Soybean Meal |
| | Soy Milk |
| | Soy Protein Isolates |
| Specialty Soy Foods/Ingredients | |
| Soy Milk | Soy Protein Concentrates |
| Tofu | Textured Soy Proteins |

TABLE A-continued

Soy Protein Products Derived from Soybean Seeds[a]

| | Processed Soy Protein Products |
|---|---|
| Tempeh | Textured Flours and Concentrates |
| Miso | Textured Concentrates |
| Soy Sauce | Textured Isolates |
| Hydrolyzed Vegetable Protein | |
| Whipping Protein | |

[a]See Soy Protein Products: Characteristics, Nutritional Aspects and Utilization (1987). Soy Protein Council.

"Processing" refers to any physical and chemical methods used to obtain the products listed in Table A and includes, and is not limited to, heat conditioning, flaking and grinding, extrusion, solvent extraction, or aqueous soaking and extraction of whole or partial seeds. Furthermore, "processing" includes the methods used to concentrate and isolate soy protein from whole or partial seeds, as well as the various traditional Oriental methods in preparing fermented soy food products. Trading Standards and Specifications have been established for many of these products (see National Oilseed Processors Association Yearbook and Trading Rules 1991-1992).

"White" flakes refer to flaked, dehulled cotyledons that have been defatted and treated with controlled moist heat to have a PDI (ASCS: ba10-65) of about 85 to 90. This term can also refer to a flour with a similar PDI that has been ground to pass through a No. 100 U.S. Standard Screen size.

"Grits" refer to defatted, dehulled cotyledons having a U.S. Standard screen size of between No. 10 and 80.

"Soy Protein Concentrates" refer to those products produced from dehulled, defatted soybeans by three basic processes: acid leaching (at about pH 4.5), extraction with alcohol (about 55-80%), and denaturing the protein with moist heat prior to extraction with water. Conditions typically used to prepare soy protein concentrates have been described by Pass ((1975) U.S. Pat. No. 3,897,574; Campbell et al., (1985) in New Protein Foods, ed. by Altschul and Wilcke, Academic Press, Vol. 5, Chapter 10, *Seed Storage Proteins*, pp 302-338).

"Extrusion" refers to processes whereby material (grits, flour or concentrate) is passed through a jacketed auger using high pressures and temperatures as a means of altering the texture of the material. "Texturing" and "structuring" refer to extrusion processes used to modify the physical characteristics of the material. The characteristics of these processes, including thermoplastic extrusion, have been described previously (Atkinson (1970) U.S. Pat. No. 3,488,770, Horan (1985) In *New Protein Foods*, ed. by Altschul and Wilcke, Academic Press, Vol. 1A, Chapter 8, pp 367-414). Moreover, conditions used during extrusion processing of complex foodstuff mixtures that include soy protein products have been described previously (Rokey (1983) *Feed Manufacturing Technology III*, 222-237; McCulloch, U.S. Pat. No. 4,454,804).

In another embodiment, this invention concerns a method for suppressing the level of expression of a gene encoding a polypeptide having ADP-glucose pyrophosphorylase activity in a transgenic plant, wherein the method comprises:
(a) transforming a plant cell with a fragment SEQ ID NOs:24, 28 or 30, or their complement;
(b) regenerating a transgenic plant from the transformed plant cell of (a); and
(c) selecting a transgenic plant wherein the level of expression of a gene encoding a polypeptide having ADP-glucose pyrophosphorylase activity has been suppressed.

Preferably, the plant is a soybean plant.

In another embodiment, the invention concerns a recombinant DNA construct comprising: (a) all or part of the nucleotide sequence set forth in SEQ ID NOs:24, 28 or 30; or (b) the complement of (a); wherein (a) or (b) is useful in co-suppression or antisense suppression of endogenous ADP-glucose pyrophosphorylase activity in a transgenic plant.

In another embodiment, the invention concerns a method for producing transgenic seed, the method comprising:
(a) transforming a plant cell with the recombinant DNA construct of:
  (i) all or part of the nucleotide sequence set forth in SEQ ID NO:24, 28 or 30; or
  (ii) the complement of (i);
wherein (i) or (ii) is useful in co-suppression or antisense suppression of endogenous ADP-glucose pyrophosphorylase activity in a transgenic plant;
(b) regenerating a transgenic plant from the transformed plant cell of (a); and
(c) selecting a transgenic plant that produces a transgenic seed having an increase in the combined oil and protein content of at least 1.6% and a decrease in the sucrose content of at least 25% as compared to seed obtained from a non-transgenic plant.

Preferably, the seed is a soybean seed.

In another embodiment, the invention concerns a method for producing transgenic seed, the method comprising:
(a) transforming a plant cell with a recombinant DNA construct comprising
  (i) all or part of the nucleotide sequence set forth in SEQ ID NOs:24, 28 or 30; or
  (ii) the complement of (i);
  wherein (i) or (ii) is useful in co-suppression or antisense suppression of endogenous ADP-glucose pyrophosphorylase activity in a transgenic plant;
(b) regenerating a transgenic plant from the transformed plant cell of (a); and
(c) selecting a transgenic plant that produces a transgenic seed having a sucrose to raffinose family oligosaccharide ratio of 1.0 or less as compared to seed obtained from a non-transgenic plant.

Preferably, the transgenic seed differs from an untransformed seed by having an increase in the combined oil and protein content of at least 1.6%, 1.8% or 2.0%. Preferably, the seed is a soybean seed.

In another embodiment, the invention concerns a method for producing defatted meal from transgenic seed, comprising:
(a) transforming a plant cell with a recombinant DNA construct comprising
  (i) all or part of the nucleotide sequence set forth in SEQ ID NOs:24, 28 or 30; or
  (ii) the complement of (i);
  wherein (i) or (ii) is useful in co-suppression or antisense suppression of endogenous ADP-glucose pyrophosphorylase activity in a transgenic plant;
(b) regenerating a transgenic plant from the transformed plant cell of (a); and
(c) selecting a transgenic plant that produces a transgenic seed wherein said seed is processed into defatted meal having an increase in the combined oil and protein content of at least 5% and a decrease in the sucrose content of at least 25% as compared to defatted meal obtained from seed of a non-transgenic plant.

Preferably, the defatted meal of the transgenic seed differs from the defatted meal of an untransformed seed by having a sucrose to raffinose family oligosaccharide ratio of 1.0 or less. Preferably, the seed is a soybean seed.

In a another embodiment, the invention concerns a transgenic seed produced by any of the above methods. Preferably, the seed is a soybean seed.

Regulatory sequences may include, and are not limited to, promoters, translation leader sequences, introns, and polyadenylation recognition sequences.

"Tissue-specific" promoters direct RNA production preferentially in particular types of cells or tissues. Promoters which cause a gene to be expressed in most cell types at most times are commonly referred to as "constitutive promoters". New promoters of various types useful in plant cells are constantly being discovered; numerous examples may be found in the compilation by Okamuro and Goldberg (*Biochemistry of Plants* 15:1-82 (1989)). It is further recognized that since in most cases the exact boundaries of regulatory sequences have not been completely defined, DNA fragments of some variation may have identical promoter activity.

A number of promoters can be used to practice the present invention. The promoters can be selected based on the desired outcome. The nucleic acids can be combined with constitutive, tissue-specific (preferred), inducible, or other promoters for expression in the host organism. Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter. A tissue-specific or developmentally regulated promoter is a DNA sequence which regulates the expression of a DNA sequence selectively in particular cells/tissues of a plant. Any identifiable promoter may be used in the methods of the present invention which causes the desired temporal and spatial expression.

Promoters which are seed or embryo specific and may be useful in the invention include patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet. 259:149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori, T., et al. (1990) Plant Mol. Biol. 14:595-604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., Bio/Technology 7:L929-932 (1989)), bean lectin and bean beta-phaseolin promoters to express luciferase (Riggs et al., Plant Sci. 63:47-57 (1989)), and wheat glutenin promoters to express chloramphenicol acetyl transferase (Colot et al., EMBO J 6:3559-3564 (1987)).

A plethora of promoters is described in WO 00/18963, published on Apr. 6, 2000, the disclosure of which is hereby incorporated by reference. Examples of seed-specific promoters include, and are not limited to, the promoter for soybean Kunitz trypsin inhibitor (Kti3, Jofuku and Goldberg, *Plant Cell* 1:1079-1093 (1989)) β-conglycinin (Chen et al., *Dev. Genet.* 10:112-122 (1989)), the napin promoter, and the phaseolin promoter.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a cognate gene of a polynucleotide of the present invention so as to control the expression of the gene. Gene expression can be modulated under conditions suitable for plant growth so as to alter the total concentration and/or alter the composition of the polypeptides of the present invention in plant cell. Thus, the present invention includes compositions, and methods for making, heterologous promoters and/or enhancers operably linked to a native, endogenous (i.e., non-heterologous) form of a polynucleotide of the present invention.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell Biol.* 8:4395-4405 (1988); Callis et al., *Genes Dev.* 1:1183-1200 (1987)). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994). A vector comprising the sequences from a polynucleotide of the present invention will typically comprise a marker gene which confers a selectable phenotype on plant cells. Typical vectors useful for expression of genes in higher plants are well known in the art and include vectors derived from the tumor-inducing (Ti) plasmid of *Agrobacterium tumefaciens* described by Rogers et al., *Meth. in Enzymol.* 153:253-277 (1987).

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

Preferred recombinant DNA constructs include the following combinations: a) a nucleic acid fragment corresponding to a promoter operably linked to at least one nucleic acid fragment encoding a selectable marker, followed by a nucleic acid fragment corresponding to a terminator, b) a nucleic acid fragment corresponding to a promoter operably linked to a nucleic acid fragment capable of producing a stem-loop structure, and followed by a nucleic acid fragment corresponding to a terminator, and c) any combination of a) and b) above. Preferably, in the stem-loop structure at least one nucleic acid fragment that is capable of suppressing expression of a native gene comprises the "loop" and is surrounded by nucleic acid fragments capable of producing a stem.

Preferred methods for transforming dicots and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); *Brassica* (U.S. Pat. No. 5,463,174); peanut (Cheng et al. (1996) *Plant Cell Rep.* 15:653-657, McKently et al. (1995) *Plant Cell Rep.* 14:699-703); papaya (Ling, K. et al. (1991) Bio/technology 9:752-758); and pea (Grant et al. (1995) *Plant Cell Rep.* 15:254-258). For a review of other commonly used methods of plant transformation see Newell, C. A. (2000) *Mol. Biotechnol.* 16:53-65. One of these methods of transformation uses *Agrobacterium rhizogenes* (Tepfler, M. and Casse-Delbart, F. (1987) *Microbiol. Sci.* 4:24-28). Transformation of soybeans using direct delivery of DNA has been published using PEG fusion (PCT publication WO 92/17598), electroporation (Chowrira, G. M. et al. (1995) *Mol. Biotechnol.* 3:17-23; Christou, P. et al. (1987) *Proc. Natl. Acad. Sci. U.S.A.* 84:3962-3966), microinjection, or particle bombardment (McCabe, D. E. et. Al. (1988) *BiolTechnology* 6:923; Christou et al. (1988) *Plant Physiol.* 87:671-674).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants are well known in the art (Weissbach and Weissbach, (1988) In.: Methods for Plant Molecular Biology, (Eds.), Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. The regenerated plants may be self-pollinated. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide(s) is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook et al. (1989) Molecular Cloning: A Laboratory Manual, Cold Spring Harbor Press; Maliga et al. (1995) Methods in Plant Molecular Biology, Cold Spring Harbor Press; Birren et al. (1998) Genome Analysis: Detecting Genes, 1, Cold Spring Harbor, N.Y.; Birren et al. (1998) Genome Analysis: Analyzing DNA, 2, Cold Spring Harbor, N.Y.; Plant Molecular Biology: A Laboratory Manual, eds. Clark, Springer, N.Y. (1997)).

Assays to detect proteins may be performed by SDS-polyacrylamide gel electrophoresis or immunological assays. Assays to detect levels of substrates or products of enzymes may be performed using gas chromatography or liquid chromatography for separation and UV or visible spectrometry or mass spectrometry for detection, or the like. Determining the levels of mRNA of the enzyme of interest may be accomplished using northern-blotting or RT-PCR techniques. Once plants have been regenerated, and progeny plants homozygous for the transgene have been obtained, plants will have a stable phenotype that will be observed in similar seeds in later generations.

In another aspect, this invention includes a polynucleotide of this invention or a functionally equivalent subfragment thereof useful in antisense inhibition or cosuppression of expression of nucleic acid sequences encoding proteins having plastidic phosphoglucomutase activity, most preferably in antisense inhibition or cosuppression of an endogenous plastidic phosphoglucomutase gene.

Protocols for antisense inhibition or co-suppression are well known to those skilled in the art.

Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al. (1998) *Plant J.* 16:651-659; and Gura (2000) *Nature* 404:804-808). Another variation describes the use of plant viral sequences to direct the suppression of proximal mRNA encoding sequences (PCT Publication WO 98/36083 published on Aug. 20, 1998). Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression see Wesley, S. V. et al. (2003) Methods in Molecular Biology, Plant Functional Genomics: Methods and Protocols 236:273-286. A construct where the stem is formed by at least 30 nucleotides from a gene to be suppressed and the loop is formed by a random nucleotide sequence has also effectively been used for suppression (WO 99/61632 published on Dec. 2, 1999). The use of poly-T and poly-A sequences to generate the stem in the stem-loop structure has also been described (WO 02/00894 published Jan. 3, 2002). Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication WO 02/00904, published 3 Jan. 2002.

The sequences of the polynucleotide fragments used for suppression do not have to be 100% identical to the sequences of the polynucleotide fragment found in the gene to be suppressed. For example, suppression of all the subunits of the soybean seed storage protein β-conglycinin has been accomplished using a polynucleotide derived from a portion of the gene encoding the a subunit (U.S. Pat. No. 6,362,399). β-conglycinin is a heterogeneous glycoprotein composed of varying combinations of three highly negatively charged subunits identified as α, α' and β. The polynucleotide sequences encoding the α and α' subunits are 85% identical to each other while the polynucleotide sequences encoding the β subunit are 75 to 80% identical to the α and α' subunits, respectively. Thus, polynucleotides that are at least 75% identical to a region of the polynucleotide that is target for suppression have been shown to be effective in suppressing the desired target. The polynucleotide may be at least 80% identical, at least 90% identical, at least 95% identical, or about 100% identical to the desired target sequence.

The isolated nucleic acids and proteins and any embodiments of the present invention can be used over a broad range of plant types, particularly dicots such as the species of the genus *Glycine*.

It is believed that the nucleic acids and proteins and any embodiments of the present invention can be with monocots as well including, but not limited to, *Graminiae* including *Sorghum bicolor* and *Zea mays*.

The isolated nucleic acid and proteins of the present invention can also be used in species from the following dicot genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Antirrhinum, Pelargonium, Ranunculus, Senecio, Salpiglossis, Cucumis, Browallia, Glycine, Pisum, Phaseolus*, and from the following monocot genera: *Bromus, Asparagus, Hemerocallis, Panicum, Pennisetum, Lolium, Oryza, Avena, Hordeum, Secale, Triticum, Bambusa, Dendrocalamus*, and *Melocanna*.

EXAMPLES

The present invention is further illustrated in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Composition of cDNA Libraries; Isolation and Sequencing of cDNA Clones cDNA libraries representing mRNAs from various cattail, corn, rice and soybean tissues were prepared. The characteristics of the libraries are described below.

TABLE 2 cDNA Libraries from Cattail, Corn, Rice and Soybean

| Library | Tissue | Clone |
|---|---|---|
| etr1c | Cattail (Typha latifolia) root | etr1c.pk005.f8 |
| p0075 | Corn, root/leaf material from dark-grown 7 day old Seedlings | p0075.cslaf22f p0075.cslaf22rb |
| p0128 | Corn, pooled primary and secondary immature ear | p0128.cpicz81r |
| rdi1c | Rice (Oryza sativa, Nipponbare) developing inflorescence at mitotic stage | rdi1c.pk001.a22 |
| rth1c | Rice leaf inoculated with Magnaporta grisea | rth1c.pk009.k14f |
| sdp3c | Soybean developing pods 8-9 mm | sdp3c.pk003.e22 |
| ses4d | Soybean embryogenic suspension 4 days after subculture | ses4d.pk0018.d10 |
| sdp2c | Soybean developing pods 6-7 mm | sdp2c.pk008.m2 |
| ssm | Soybean shoot meristem | ssm.pk0072.e7 |
| ssl | Soybean seedling 5-10 day | ssl.pk0021.h3 |
| sgs4c | Soybean seeds 2 days after germination | sgs4c.pk005.b10 | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Example 2

Identification of cDNA Clones cDNA clones encoding plastidic phosphoglucomutase proteins were identified by conducting BLAST (Basic Local Alignment Search Tool; Altschul et al. (1993) *J. Mol. Biol.* 215:403-410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Plastidic Phosphoglucomutase Proteins

The BLASTX search using the EST sequences from clones listed in Table 3 revealed similarity of the polypeptides encoded by the cDNAs to plastidic phosphoglucomutase from *Brassica napus* (NCBI General Identifier No. 6272125) and *Pisum sativum* (NCBI General Identifier No. 6272283 and NCBI General Identifier No. 10190529). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, an EST and PCR, or an FIS and PCR ("CGS"):

TABLE 3

BLAST Results for Sequences Encoding Polypeptides Homologous to *Brassica napus* and *Pisum sativum* Plastidic Phosphoglucomutase

| Clone | Status | BLAST pLog Score |
|---|---|---|
| etr1c.pk005.f8 (FIS) | CGS | >254.00 (GI No. 6272125; *B. napus*) |
| Contig Composed of: p0075.cslaf22f (EST) p0075.cslaf22rb (EST) p0128.cpicz81r (EST) | CGS | >254.00 (GI No. 6272283; *P. sativum*) |
| rth1c.pk009.k14f (EST) | EST | 58.00 (GI No. 6272283; *P. sativum*) |
| sdp3c.pk003.e22 (EST and PCR Fragments) | CGS | >254.00 (GI No. 6272283; *P. sativum*) |
| rdi1c.pk001.a22 (FIS) | CGS | 180.00 (GI No. 10190529; *P. sativum*) |

The data in Table 4 represents a calculation of the percent identity of the amino acid sequences set forth in SEQ ID NOs:2, 4, 6, 8, and 10, and the *Brassica napus* and *Pisum sativum* sequences.

TABLE 4

Percent Identity of Amino Acid Sequences Deduced From the Nucleotide Sequences of cDNA Clones Encoding Polypeptides Homologous to *Brassica napus* and *Pisum sativum* Plastidic Phosphoglucomutase

| SEQ ID NO. | Percent Identity to |
|---|---|
| 2 | 79% (GI No. 6272125; *B. napus*) |
| 4 | 77% (GI No. 6272283; *P. sativum*) |
| 6 | 80% (GI No. 6272283; *P. sativum*) |
| 8 | 90% (GI No. 6272283; *P. sativum*) |
| 10 | 76% (GI No. 10190529; *P. sativum*) |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments, BLAST scores and probabilities indicate that the nucleic acid fragments comprising the instant cDNA clones encode a substantial portion of a plastidic phosphoglucomutase.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase☐ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains glufosinate (2 mg per liter) and lacks casein or proline. The tissue continues to grow slowly on this medium. After an additional 2 weeks the tissue can be transferred to fresh N6 medium containing glufosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 5

Expression of Chimeric Genes in Dicot Cells

A seed-specific construct composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin construct includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire construct is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed construct.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL of liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli;* Gritz et al. (1983) *Gene* 25:179-188) and the 3' region of the nopaline synthase gene from the T-DNA of the Ti plasmid of *Agrobacterium tumefaciens*. The seed construct comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches of mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/mL ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Transformation of Somatic Soybean Embryo Cultures

Generic Stable Soybean Transformation Protocol:

Soybean embryogenic suspension cultures are maintained in 35 ml liquid media (SB55 or SBP6) on a rotary shaker, 150 rpm, at 28° C. with mixed fluorescent and incandescent lights on a 16:8 h day/night schedule. Cultures are subcultured every four weeks by inoculating approximately 35 mg of tissue into 35 ml of liquid medium.

TABLE 5

| Stock Solutions (g/L): | |
|---|---|
| MS Sulfate 100X Stock | |
| $MgSO_4$ $7H_2O$ | 37.0 |
| $MnSO_4$ $H_2O$ | 1.69 |
| $ZnSO_4$ $7H_2O$ | 0.86 |
| $CuSO_4$ $5H_2O$ | 0.0025 |
| MS Halides 100X Stock | |
| $CaCl_2$ $2H_2O$ | 44.0 |
| KI | 0.083 |
| $CoCl_2$ $6H_2O$ | 0.00125 |
| $KH_2PO_4$ | 17.0 |
| $H_3BO_3$ | 0.62 |
| $Na_2MoO_4$ $2H_2O$ | 0.025 |
| MS FeEDTA 100X Stock | |
| $Na_2EDTA$ | 3.724 |
| $FeSO_4$ $7H_2O$ | 2.784 |
| B5 Vitamin Stock | |
| 10 g m-inositol | |
| 100 mg nicotinic acid | |
| 100 mg pyridoxine HCl | |
| 1 g thiamine | |
| SB55 (per Liter, pH 5.7) | |
| 10 ml each MS stocks | |
| 1 ml B5 Vitamin stock | |
| 0.8 g $NH_4NO_3$ | |
| 3.033 g $KNO_3$ | |
| 1 ml 2,4-D (10 mg/mL stock) | |
| 60 g sucrose | |
| 0.667 g asparagine | |
| SBP6 | |
| same as SB55 except 0.5 ml 2,4-D | |
| SB103 (per Liter, pH 5.7) | |
| 1X MS Salts | |
| 6% maltose | |
| 750 mg $MgCl_2$ | |
| 0.2% Gelrite | |

TABLE 5-continued

Stock Solutions (g/L):

SB71-1 (per Liter, pH 5.7)

1X B5 salts
1 ml B5 vitamin stock
3% sucrose
750 mg MgCl$_2$
0.2% Gelrite

Soybean embryogenic suspension cultures are transformed with plasmid DNA by the method of particle gun bombardment (Klein et al (1987) Nature 327:70). A DuPont Biolistic™ PDS1000/HE instrument (helium retrofit) is used for these transformations.

To 50 ml of a 60 mg/ml 1 μm gold particle suspension is added (in order); 5 μl DNA(1 μg/μl), 20 μl spermidine (0.1 M), and 50 μl CaCl$_2$ (2.5 M). The particle preparation is agitated for 3 min, spun in a microfuge for 10 sec and the supernatant removed. The DNA-coated particles are then washed once in 400 μl 70% ethanol and re suspended in 40 μl of anhydrous ethanol. The DNA/particle suspension is sonicated three times for 1 sec each. Five μl of the DNA-coated gold particles are then loaded on each macro carrier disk. For selection, a plasmid conferring resistance to hygromycin phosphotransferase (HPT) may be co-bombarded with the silencing construct of interest.

Approximately 300-400 mg of a four week old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1000 psi and the chamber is evacuated to a vacuum of 28 inches of mercury. The tissue is placed approximately 3.5 inches away from the retaining screen and bombarded three times. Following bombardment, the tissue is placed back into liquid and cultured as described above.

Eleven days post bombardment, the liquid media is exchanged with fresh SB55 containing 50 mg/ml hygromycin. The selective media is refreshed weekly. Seven weeks post bombardment, green, transformed tissue is observed growing from untransformed, necrotic embryogenic clusters. Isolated green tissue is removed and inoculated into individual flasks to generate new, clonally propagated, transformed embryogenic suspension cultures. Thus each new line is treated as an independent transformation event. These suspensions can then be maintained as suspensions of embryos maintained in an immature developmental stage or regenerated into whole plants by maturation and germination of individual somatic embryos.

Independent lines of transformed embryogenic clusters are removed from liquid culture and placed on a solid agar media (SB103) containing no hormones or antibiotics. Embryos are cultured for four weeks at 26° C. with mixed fluorescent and incandescent lights on a 16:8 h day/night schedule. During this period, individual embryos are removed from the clusters and screened for alterations in gene expression.

It should be noted that any detectable phenotype, resulting from the cosuppression of a target gene, can be screened at this stage. This would include, but not be limited to, alterations in protein content, carbohydrate content, growth rate, viability, or the ability to develop normally into a soybean plant.

Example 8

Plasmid DNAs for "Complementary Region" Co-Suppression

The plasmids used in these experiments were made using standard cloning methods well known to those skilled in the art (Sambrook et al (1989) Molecular Cloning, CSHL Press, New York). A starting plasmid pKS18HH (U.S. Pat. No. 5,846,784 the contents of which are hereby incorporated by reference) contains a hygromycin B phosphotransferase (HPT) obtained from E. coli strain W677 under the control of a T7 promoter and the 35S cauliflower mosaic virus promoter. Plasmid pKS18HH thus contains the T7 promoter/HPT/T7 terminator cassette for expression of the HPT enzyme in certain strains of E. coli, such as NovaBlue(DE3) [from Novagen], that are lysogenic for lambda DE3 (which carries the T7 RNA Polymerase gene under IacV5 control). Plasmid pKS18HH also contains the 35S/HPT/NOS cassette for constitutive expression of the HPT enzyme in plants, such as soybean. These two expression systems allow selection for growth in the presence of hygromycin to be used as a means of identifying cells that contain the plasmid in both bacterial and plant systems. pKS18HH also contains three unique restriction endonuclease sites suitable for the cloning other chimeric genes into this vector. Plasmid ZBL100 (PCT Application No. WO 00/11176 published on Mar. 2, 2000) is a derivative of pKS18HH with a reduced NOS 3' terminator. Plasmid pKS67 is a ZBL100 derivative with the insertion of a beta-conglycinin promoter, in front of a NotI cloning site, followed by a phaseolin 3' terminator (described in PCT Application No. WO 94/11516, published on May 26, 1994).

The 2.5 kb plasmid pKS17 contains pSP72 (obtained from Promega Biosystems) and the T7 promoter/HPT/T7 3' terminator region, and is the original vector into which the 3.2 kb BamHI-SalI fragment containing the 35S/HPT/NOS cassette was cloned to form pKS18HH. The plasmid pKS102 is a pKS17 derivative that is digested with XhoI and SalI, treated with mung-bean nuclease to generate blunt ends, and ligated to insert the following linker:
GGCGCGCCMGCTTGGATCCGTCGACGGCGCGCC
SEQ ID NO:18

The plasmid pKS83 has the 2.3 kb BamHI fragment of ML70 containing the Kti3 promoter/NotI/Kti3 3' terminator region (described in PCT Application No. WO 94/11516, published on May 26, 1994) ligated into the BamHI site of pKS17.

Example 9

Suppression by ELVISLIVES Complementary Region

Constructs have now been made which have "synthetic complementary regions" (SCR). In this example the target sequence is placed between complementary sequences that are not known to be part of any biologically derived gene or genome (i.e. sequences that are "synthetic" or conjured up from the mind of the inventor). The target DNA would therefore be in the sense or antisense orientation and the complementary RNA would be unrelated to any known nucleic acid sequence. It is possible to design a standard "suppression vector" into which pieces of any target gene for suppression could be dropped. The plasmids pKS106, pKS124, and pKS133 (SEQ ID NO:17) exemplify this. One skilled in the art will appreciate that all of the plasmid vectors contain antibiotic selection genes such as, but not limited to, hygromycin phosphotransferase with promoters such as the T7 inducible promoter.

pKS106 uses the beta-conglycinin promoter while the pKS124 and pKS133 plasmids use the Kti promoter, both of these promoters exhibit strong tissue specific expression in the seeds of soybean. pKS106 uses a 3' termination region from the phaseolin gene, and pKS124 and pKS133 use a Kti 3' termination region. pKS106 and pKS124 have single copies of the 36 nucleotide EagI-ELVISLIVES sequence surrounding a NotI site (the amino acids given in parentheses are back-translated from the complementary strand): SEQ ID NO:19

LIVES cloning site made from SEQ ID NOs:14 and 15 is inserted into the NotI site of pKS121 to form pKS124. The EagI digested EL PCR product can be ligated into NotI digested pKS124 to form the 2×EL plasmid, pKS133 (SEQ ID NO:17), containing two copies of ELVISLIVES. An additional 2×EL vector, pKS151, is similar to pKS133 except for the addition of a second hygromycin phosphotransferase gene with a 35S-CaMV promoter. Any synthetic sequence, or naturally occurring sequence, can be used in an analogous manner. The addition of a 574 base pair NotI fragment (SEQ ID NO:14) into a NotI-digested pKS133 produces pTC103. The 574 base pair Not I fragment (SEQ

```
     EagI   E   L   V   I   S   L   I   V   E   S   NotI
     CGGCCG GAG CTG GTC ATC TCG CTC ATC GTC GAG TCG GCGGCCGC (S) (E) (V) (I) (L) (S) (I) (V) (L) (E)  EagI
     CGA CTC GAC GAT GAG CGA GAT GAC CAG CTC  CGGCCG
``` pKS133 has 2× copies of ELVISLIVES surrounding the NotI site: SEQ ID NO:20

```
     EagI    E  L  V  I  S  L  I  V  E  S  EagI
     cggccg  gagctggtcatctcgctcatcgtcgagtcg  gcggccg E  L  V  I  S  L  I  V  E  S      NotI
     gagctggtcatctcgctcatcgtcgagtcg     gcggccgc (S)(E)(V)(I)(L)(S)(I)(V)(L)(E)    EagI
     cgactcgacgatgagcgagatgaccagctc    cggccgc
     (S)(E)(V)(I)(L)(S)(I)(V)(L)(E)    EagI
     cgactcgacgatgagcgagatgaccagctc    cggccg
```

The idea is that the single EL linker (SCR) can be duplicated to increase stem lengths in increments of approximately 40 nucleotides. A series of vectors will cover the SCR lengths between 40 bp and the 300 bp. Various target gene lengths are also under evaluation. It is believed that certain combinations of target lengths and complementary region lengths will give optimum suppression of the target, although preliminary results would indicate that the suppression phenomenon works well over a wide range of sizes and sequences. It is also believed that the lengths and ratios providing optimum suppression may vary somewhat given different target sequences and/or complementary regions.

The plasmid pKS106 is made by putting the EagI fragment of ELVISLIVES (SEQ ID NO:19) into the NotI site of pKS67. The ELVISLIVES fragment is made by PCR using two primers and no other DNA:

SEQ ID NO:21
5'-
GAATTCCGGCCGGAGCTGGTCATCTCGCTCATCGTCGAGTCGGCGGCCGC
CGACTCGACGATGAGCGAGATGACCAGCTCCGGCCGGAATTC-3'

SEQ ID NO:22
5'-GAATTCCGGCCGGAG-3'

The product of the PCR reaction is digested with EagI (5'-CGGCCG-3') and then ligated into NotI digested pKS67. The term "ELVISLIVES" and "EL" are used interchangeably herein.

Additional plasmids can be used to test this example. For example, pKS121 contains the Kti3 promoter/NotI/Kti3 3' terminator fragment analogous to pKS83 inserted into the BamHI-SalI digested pKS102. The EagI digested ELVIS- ID NO:14) contains a 541 base pair region (SEQ ID NO:15) of the soybean plastid phosphoglucomutase coding region (SEQ ID NO:8).

Example 10

Down Regulation of Plastidic Phosphoglucomutase in Soybean

Soybean was transformed with the plasmid DNA, pTC103, and transgenic lines were selected. Transgenic lines were screened for down regulation of plastidic phosphoglucomutase in soybean. The screening assay involved iodine staining for the presence or absence of starch in immature seeds (mid-pod stage). The method involved harvesting half of the seed, and putting that seed on dry ice and storing at −80 C. The other half of the seed was placed in 100% ethanol overnight, and subsequently stained with water:lugol (4:1) solution for 10 to 30 minutes at room temperature. Lugol is an iodine/potassium iodide solution, commercially available from Sigma.

Four out of nineteen events showed a clear reduction in iodine staining indicating a reduction in starch content. This may reflect a 21% cosuppression success with the hairpin construct. Three additional events showed potential, reduction in iodine staining, although the differences in staining were subtle. The segregation patterns of events 100-2-1 and 108-3-1 are consistent with a theoretical segregation of a dominant co-suppression (1:3).

TABLE 6

Summary of Iodine Screen

|  | Sum |
|---|---|
| + Events | 4 |
| − Events | 12 |
| ? Events | 3 |
| Total Events Analyzed | 19 |
| Events with no plants/sterile/dwarf | 2 |
| Total Events | 27 |

TABLE 7

Seed segregation information of potential positive pPGM events.
D = dark blue stain, L = light blue or no stain,
D/L in between dark and light stain

| Event | Plant | D:L seed ratio | Note |
|---|---|---|---|
| 100-2-1 | 1 | 1:5 | clear positive |
| 100-2-1 | 2 | 3:2 | clear positive |
| 100-2-1 | 3 | 1:5 | clear positive |
| 108-3-1 | 1 | 0:6 | clear positive |
| 108-3-1 | 2 | 2:4 | clear positive |
| 108-3-1 | 3 | 1:5 | clear positive |
| 105-2-3 | 1 | 4:0 | negative |
| 105-2-3 | 2 | 1:5 | clear positive |
| 105-1-6 | 1 | 4:0 | negative |
| 105-1-6 | 3 | 2:2 | clear positive |
| 105-1-1 | 1 | 4:2 | D/L |
| 105-1-1 | 2 | 0:6 | D/L |
| 105-1-1 | 3 | 6:0 | D/L |
| 101-2-6 | 1 | 6:0 | D/L |
| 101-2-6 | 3 | 2:3 | D/L |
| 102-3-3 | 1 | 2:3 | D/L |
| 102-3-3 | 2 | 3:0 | D/L |

Example 11

Silencing of Plastidic Phosphoglucomutase (pPGM) Results in a Stable Reduction of Transient Starch Accumulation in Developing Soybean Seeds Transgenic soybean events were produced as described in Example 10. Developing soybean seeds were harvested at approximately mid-maturity (20 to 30 days after flowering (DAF)) and starch content was quantified as described in Brown and Huber, Physiologia Plantarum 72:518-524 (1988). T1 seeds from three transgenic events showed about an 80% reduction in starch content as compared to wild-type seeds (Table 8). The starch data correlated with the iodine staining described in Example 10, i.e., seeds that do not stain blue have a significant reduction in starch content while blue-staining seeds have starch contents similar to wild-type

TABLE 8

Starch Content of T1 Seeds (Approximately Mid-maturity) Segregating for Co-suppression of pPGM. B = Seeds Staining Blue.
W = Seeds Not Staining.
Blue Staining Indicates Presence of Starch.

| Event | Iodine score | Mg starch/g seed mean | st. dev. | % of wild-type |
|---|---|---|---|---|
| WT (Jack) | B | 22.83 | 5.69 | 100 |
| 108-3-1 | W | 5.20 | 2.24 | 20 |
| 108-3-1 | B | 25.92 | — | 100 |
| 105-1-8 | nd | nd | nd | nd |
| 100-2-1 | W | 5.27 | 1.66 | 22 |
| 100-2-1 | B | 24.27 | 5.40 | 100 |
| 105-1-6 | W | 2.69 | 3.81 | 14 |
| 105-1-6 | B | 18.87 | 6.76 | 100 | nd = not determined

The soluble carbohydrate composition of developing transgenic seeds was measured by high performance anion exchange chromatography/pulsed amperometric detection (HPAE/PAD). Individual seeds from transgenic lines were harvested at mid-maturity (20 to 30 DAF) for detection of carbohydrate composition. The seeds were frozen in liquid nitrogen, ground with a mortar and pestle, and transferred to 15 ml microcentrifuge tubes. Ethanol (80%) was added to the tubes and the samples were heated to 70° C. for 15 minutes. Samples were centrifuged at 4000 rpm for 15 minutes at 4° C. and the supernatant collected. The pellet was re-extracted two additional times with 80% ethanol at 70° C. The supernatants were combined, dried down in a speedvac, and the pellet re-suspended in water. Furthermore, the extracts were filtered through a 0.2 μm Nylon-66 filter (Rainin, Emeryville, Calif.) and analyzed by HPAE/PAD using a DX500 anion exchange analyzer (Dionex, Sunnyvale, Calif.) equipped with a 250×4 mm CarboPac PA1 anion exchange column and a 25×4 mm CarboPac PA guard column. Soluble carbohydrates were separated with a 30 minute isocratic run of 0.5 mM NaAc in 150 mM NaOH at a flow rate of 1.0 mL/min. A dilution series of glucose, fructose, sucrose, raffinose, stachyose and verbascose were used as external standards.

Soluble carbohydrate analysis on 6 seeds per event segregating for iodine staining (starch presence) indicated no major change in concentration of sucrose and total soluble carbohydrates at approximately mid-maturity (Table 9). No raffinose family oligosaccharides (RFOs) were observed at this stage of development; hence, no sucrose to RFO ratio could be determined.

TABLE 9

Sucrose and Total Soluble Sugar Content (mg/g seed) of Segregating T1 Seeds Harvested at Mid-maturity.
D = Dark Blue Stain, L = Light Blue or No Stain

| Event | Plant No. | Seed Score | Sucrose mean | std. | Total Soluble Sugars mean | std. |
|---|---|---|---|---|---|---|
| 108-3-1 | 1 | L | 22.8 | 3.1 | 26.5 | 3.8 |
| 108-3-1 | 3 | D | 13.1 | — | 17.2 | — |
| 108-3-1 | 3 | L | 10.4 | 5.9 | 14.7 | 5.4 |
| 105-1-8 |   | nd* | nd | nd | nd | nd |
| 100-2-1 | 2 | D | 16.0 | 4.7 | 21.0 | 6.0 |
| 100-2-1 | 2 | L | 18.6 | 4.7 | 24.3 | 5.6 |
| 105-1-6 | 1 | D | 31.5 | 12.5 | 36.4 | 3.8 |
| 105-1-6 | 3 | D | 23.1 | 2.6 | 27.3 | 2.6 |
| 105-1-6 | 3 | L | 18.2 | 5.2 | 23.4 | 5.4 | nd* = not determined

T1 seeds from event 108-3-1 were planted in a growth chamber and T2 seeds were harvested at mid-maturity and screened for starch presence using the iodine screen described in Example 10. Starch and soluble carbohydrate content of T2 seeds were determined as described above.

T2 seeds in which the pPGM gene is silenced (referred to as PGM-KO) showed an 80% decrease in starch content (Table 10). Null-segregating T2 seeds were also identified which had wild-type starch levels (referred to as PGM-WT). No major differences in soluble carbohydrate concentrations between pPGM-silenced T2 seeds (PGM-KO) and wild-type seeds (Jack or PGM-WT) were observed at this stage of development. This data is similar to data obtained from T1 seeds (Table 8 and Table 9) and suggest that the event is inherited in a stable manner.

TABLE 10

Starch, Sucrose and Total Soluble Carbohydrate Content of T2 Seeds (Growth Chamber Grown) from pPGM-Silenced Seeds Harvested at Mid-maturity. B = Seeds Staining Blue. W = Seeds Not Staining.
Blue Staining Indicates Presence of Starch.

| Name | Event | Iodine Score | mg Sucrose/g Seed | mg Total CHOs/g Seed | mg Starch/g Seed (mean) | % of WT |
|---|---|---|---|---|---|---|
| Jack | Control | B | 15.9 | 19.8 | 22.83 | 100 |
| PGM-KO | 108-3-1 | W | 14.8 | 21.3 | 3.7 | 22 |
| PGM-WT | 108-3-1 | B | 16.6 | 19.7 | 16.89 | 100 |

Starch quantitation of developing soybean seeds harvested at 20, 30, 40 and 50 DAF indicated that throughout seed development, the starch accumulation of a pPGM-silenced soybean was reduced by 85% as compared to its null segregant (FIG. 2).

Example 12

Silencing of Plastidic Phosphoglucomutase Decreases Total Carbohydrate Content and Alters the Sucrose to Raffinose Family Oligosaccharide Ratio in Mature Seeds Transgenic T2 soybean seeds were harvested at mid-maturity and screened for reduced starch content using the iodine screen described in Example 10. In total, three thousand seeds (field and growth chamber grown) from 436 plants representing 21 different events were screened. A secondary screen using 20 seeds per plant was conducted to identify potential homozygotes. Five events (108-3-1, 105-1-8, 100-2-1, 105-1-7 and 100-3-2) showed a decreased or no iodine staining.

Carbohydrate analysis (determined as described in Example 11) of mature T2 seeds from plants grown in a growth chamber (GC) revealed a decrease in total soluble carbohydrates of approximately 11% with sucrose being the major sugar affected (38% decrease) as compared to their null segregant (FIG. 3). Carbohydrate analysis of field grown events revealed a decrease in total soluble carbohydrates of approximately 14 to 25% together with a 30 to 39% decrease in sucrose. In both the growth chamber and field grown plants, mature seeds from the pPGM-silenced events (PGM-KO) were characterized with a distinctive change in sucrose to RFO ratio. Under these conditions the sucrose to RFO ratio of wild-type seeds averaged around 1.3 to 1.7 while the sucrose to RFO ratio of pPGM cosuppressed seeds averaged around 0.7 to 0.9.

Seeds from a selected number of events were grown in a growth chamber to produce T3 seeds. Carbohydrate analysis of T3 seeds from pPGM-silenced events revealed a decrease in total soluble carbohydrates of approximately 24 to 35% as compared to their wild-type. Sucrose content decreased by 35 to 48% whereas RFO decreased by approximately 14% (FIG. 4).

The carbohydrate profile of these T3 seeds is thus very similar to R2 seeds and indicates (as was seen with the starch content) that the pPGM trait is inherited in a stable manner. The sucrose to RFO ratio of pPGM co-suppressed R3 seeds (ratio of 1.2 to 1.5) was as compared to the null segregant (ratio of 1.6 to 2.0). Although the sucrose to RFO ratio in T3 seeds is somewhat higher as compared to T2 seeds, the decrease in the sucrose to RFO ratio between pPGM co-suppressed seeds and wild-type seeds averages around 0.5.

Example 13

Silencing of Plastidic Phosphoglucomutase (pPGM) Results in an Increased Accumulation of Oil and/or Protein in Mature Seeds Total oil and protein content of mature T2 seeds from event 108-3-1-1 showing a pPGM-silenced phenotype was determined and compared to the oil and protein content of a pPGM null segregant (wild-type phenotype) from the same event (Table 11). Percent oil and percent protein changes were expressed on a seed dry weight basis. Seed composition of wild-type 92B91 was performed as a control reference. Protein and oil were measured by Woodson-Tenant Labs (Des Moines, Iowa.), using standard AOAC methods; combustion method for protein (AOAC Official Method 990.03; 2000 AOAC International), and ether extraction method for oil (AOAC Official Method 920.39; 2000 AOAC International).

Field grown pPGM-silenced seeds showed an increased oil content of up to 2% on a seed dry wt basis and a slightly increased protein content (1% on a seed dry wt basis) as compared to seeds from the null segregant. Total oil content of growth chamber grown pPGM co-suppressed seeds increased by 4% on a seed dry wt basis. This high increase in oil content was accompanied with a decreased protein content (Table 11). No major difference was observed between the seed composition of PGM-WT and the wild-type cultivar 92B91.

TABLE 11

Seed Composition of T2 seeds from a pPGM-Silenced Line (PGM-KO) and a Null Segregant (PGM-WT) for Event 108-3-1-1

| ID | Growth Condition | Pheno-type | % Oil | % Protein | % Oil Increase | % Protein Increase | % Oil & Protein Increase |
|---|---|---|---|---|---|---|---|
| 2097-7 | Growth Chamber | PGM-KO | 23.39 | 37.08 | 4.19 | −3.04 | 1.15 |
| 2097-7 | Field | PGM-KO | 21.22 | 41.25 | 2.20 | +1.12 | 3.32 |
| 2097-1 | Field | PGM-WT | 19.20 | 40.12 | — | — | — |
| 92B91 | Field | wild-type | 20.36 | 40.40 | — | — | — |

T2 seeds from event 108-3-1-1 were planted in a growth chamber to produce T3 seeds. This T3 generation of mature seeds from pPGM co-suppressed seeds showed the greatest increase in protein content rather than oil content when compared to their null segregant (Table 12; percent oil and percent protein changes were calculated on a seed dry weight basis). Interestingly, the sum of both increase in oil and protein content was similar for T3 seeds from both plants, ranging from 1.76 to 1.83%, on a seed dry wt basis.

TABLE 12

Seed Composition of T3 Seeds from Two pPGM-Silenced Plants (PGM-KO) and a Null Segregant (PGM-WT)

| Event | ID | Pheno-type | % Oil | % Protein | % Oil Increase | % Protein Increase | % Oil & Protein Increase |
|---|---|---|---|---|---|---|---|
| 108-3-1-1 | JS1-261 | PGM-KO | 22.03 | 40.09 | −0.61 | 2.37 | 1.76 |
| 108-3-1-1 | JS2-265 | PGM-KO | 22.99 | 39.21 | 0.35 | 1.49 | 1.83 |
| 108-3-1-1 | JS3-2642 | PGM-WT | 22.64 | 37.72 | — | — | — |

T3 seeds from several other events having cv. Jack as their genetic background showed similar trends as observed with the event 108-3-1-1, which has cv. 92B91 as its genetic background. The increase in the sum of oil and protein content ranged from 0.98 to 3.14% as expressed on a seed dry wt basis (Table 13).

TABLE 13

Seed Composition of T3 Seeds from pPGM-Silenced (PGM-KO) and
PGM Wild-Type (PGM-WT) Events in a cv. Jack Background

| Event | Pheno-type | % Oil | % Protein | % Oil Increase | % Protein Increase | % Oil & Protein Increase |
|---|---|---|---|---|---|---|
| 101-2-6-3 | PGM-WT | 22.36 | 38.48 | — | — | — |
| 105-1-8-2 | PGM-KO | 21.29 | 40.53 | −1.07 | 2.05 | 0.98 |
| 100-2-1-1 | PGM-KO | 23.92 | 40.06 | 1.56 | 1.58 | 3.14 |
| 100-2-1-1 | PGM-KO | 21.79 | 40.69 | −0.57 | 2.21 | 1.64 |

Homozygous pPGM-silenced (PGM-KO) and pPGM-wild-type (PGM-WT) seeds, originating from crosses between pPGM knockout event and elite germplasm, were grown in the field in 2003 and in 2004. The seed compositions were determined and are shown in Table 14. The percent oil, percent protein and percent combined oil and protein changes are expressed on a dry weight basis. The moisture content of each sample was measured in the 2004 experiment. For the 2003 data, a moisture content of 13% was assumed, to calculate the dry weight values. For the data shown in Table 14, a range of 1.0% to 3.5% was observed for the percent increase in oil and protein.

TABLE 14

Seed Composition of Field Grown Homozygous pPGM-Silenced (PGM-KO) and PGM-Wild-Type (PGM-WT) Seeds.

| Elite Background | Year | Pheno-type | % Oil | % Protein | % Oil Increase | % Protein Increase | % Oil & Protein Increase |
|---|---|---|---|---|---|---|---|
| 92B63 | 2003 | PGM-KO | 22.7 | 40.6 | 1.3 | −0.3 | 1.0 |
| 92B63 | 2003 | PGM-WT | 21.4 | 40.9 | — | — | — |
| 92B63 | 2004 | PGM-KO | 19.1 | 42.2 | 1.1 | 0.5 | 1.6 |
| 92B63 | 2004 | PGM-WT | 18.0 | 41.7 | — | — | — |
| 92B91 | 2003 | PGM-KO | 25.7 | 39.4 | 2.5 | 1.0 | 3.5 |
| 92B91 | 2003 | PGM-WT | 23.2 | 38.4 | — | — | — |
| 92B91 | 2004 | PGM-KO | 21.4 | 40.2 | 1.7 | 0.3 | 2.0 |
| 92B91 | 2004 | PGM-WT | 19.7 | 39.9 | — | — | — |
| 93B87 | 2003 | PGM-KO | 23.1 | 40.2 | 0.7 | 1.2 | 1.9 |
| 93B87 | 2003 | PGM-WT | 22.4 | 39.0 | — | — | — |
| 93B87 | 2004 | PGM-KO | 21.5 | 42.4 | 1.4 | 0.8 | 2.2 |
| 93B87 | 2004 | PGM-WT | 20.1 | 41.6 | — | — | — |

Example 14

Characterization of Defatted Meal from Transgenic Soybean Seeds with Silenced Plastidic Phosphoglucomutase (pPGM)

T2 soybean seeds were ground to a fine powder and oil was extracted using heptane. Approximately 200 mg of soybean seed were weighed and transferred into pre-weighed 10 ml glass screw cap tubes. Two ml of heptane were added and the mixture was vortexed for 15 min at room temperature. The glass tubes were centrifuged at 3500 rpm for 20 minutes and the heptane was carefully decanted into a new, pre-weighed glass tube. The pellet was re-extracted another three times as described above and all supernatants were pooled. The hexane was removed by evaporation using a speedvac. Total oil content was determined gravimetrically.

An aliquot of the defatted meal was used for protein determination. About 60 mg of meal was transferred to a 15 ml polypropylene tube and 10 ml 0.1 N NaOH were added and the mixture was incubated at 60° C. for 1 hr. One ml of the suspension was transferred to a 2 ml eppendorf tube and centrifuged at 14,000 rpm for 3 minutes. The supernatant was diluted several fold and the protein content was determined using a microplate assay based on Sigma Total Protein Protocol (Procedure 541-2, Sigma).

The soluble carbohydrate profile of defatted soybean meal from T2 seeds is shown in FIG. 5. Sucrose to RFO ratios of 0.82 and 0.87 were observed for the pPGM-suppressed event, 108-3-1-1.

The percent oil and percent protein content of defatted meal from T2 Seeds of event 108-3-1-1 was determined on a wet-weight basis and is presented in Table 15. A percent increase in combined oil and protein of 3.02% and 4.82% was observed for defatted meal from a pPGM-suppressed line grown in the growth chamber and in the field, respectively.

The percent oil and percent protein content of defatted meal from T2 Seeds of event 108-3-1-1 was determined on a dry-weight basis and is presented in Table 16. A percent increase in combined oil and protein of 3.20% and 5.17% was observed for defatted meal from a pPGM-suppressed line grown in the growth chamber and in the field, respectively.

TABLE 15

Characterization of Defatted Meal (wet-weight basis) from T2 Seeds of Event 108-3-1-1 from a pPGM Co-suppressed Events (PGM-KO) and a Null Segregant (PGM-WT)

| ID | Growth Condition | Pheno-type | % Oil | % Protein | % Oil Increase | % Protein Increase | % Oil & Protein Increase |
|---|---|---|---|---|---|---|---|
| 2097-7 | Growth Chamber | PGM-KO | 18.82 | 37.54 | 3.40 | −0.38 | 3.02 |
| 2097-7 | Field | PGM-KO | 17.65 | 40.51 | 2.23 | 2.59 | 4.82 |
| 2097-1 | Field | PGM-WT | 15.42 | 37.92 | — | — | — |
| 92B91 | Field | wild-type | 16.92 | 36.80 | — | — | — |

TABLE 16

Characterization of Defatted Meal (dry-weight basis) from T2 seeds of Event 108-1-1 from a pPGM Co-suppressed Event (PGM-KO) and a Null Segregant (PGM-WT)

| ID | Growth Condition | Pheno-type | % Oil | % Protein | % Oil Increase | % Protein Increase | % Oil & Protein Increase |
|---|---|---|---|---|---|---|---|
| 2097-7 | Growth Chamber | PGM-KO | 18.82 | 40.31 | 3.40 | −0.20 | 3.20 |
| 2097-7 | Field | PGM-KO | 17.65 | 43.45 | 2.23 | 2.94 | 5.17 |
| 2097-1 | Field | PGM-WT | 15.42 | 40.51 | — | — | — |
| 92B91 | Field | wild-type | 16.92 | 39.35 | — | — | — |

Example 15

Characterization of cDNA Clones Encoding the Large Subunit and the Small Subunit Polypeptides of Soybean ADP-Glucose Pyrophosphorylase A BLAST analysis of soybean sequences identified cDNA clones that encoded proteins with high sequence similarity to the large subunit of ADP-glucose pyrophosphorylase from chickpea, *Cicer arietinum* (NCBI General Identifier No. 13487785), and to the small subunit, PvAGPS1, of ADP-glucose pyrophosphorylase from *Phaseolus vulgaris* (NCBI General Identifier No. 29421116). SEQ ID NO:24, encoded by SEQ ID NO:23, corresponds to the amino acid sequence of a large subunit polypeptide of soybean ADP-glucose pyrophosphorylase and has a pLog score of greater than 254 when compared to the large subunit of ADP-glucose pyrophosphorylase from chickpea (SEQ ID NO:25; GI No. 13487785). SEQ ID NO:28, encoded by SEQ ID NO:27, corresponds to the amino acid sequence of a first small subunit polypeptide (SS1) of soybean ADP-glucose pyrophosphorylase and has a pLog score of greater than 254 when compared to the small subunit polypeptide, PvAGPS1, of ADP-glucose pyrophosphorylase from *Phaseolus vulgaris* (SEQ ID NO:31; GI No. 29421116). SEQ ID NO:30, encoded by SEQ ID NO:29, corresponds to the amino acid sequence of a second small subunit polypeptide (SS2) of soybean ADP-glucose pyrophosphorylase and has a pLog score of greater than 254 when compared to the small subunit polypeptide, PvAGPS1, of ADP-glucose pyrophosphorylase from *Phaseolus vulgaris* (SEQ ID NO:31; GI No. 29421116).

The large subunit amino acid sequences of SEQ ID NOs:24, 25 and 26 were aligned and the percent sequence identities were calculated for each pair of sequences. The soybean large subunit amino acid sequence of SEQ ID NO:24 is 79.1% identical to the large subunit of ADP-glucose pyrophosphorylase from chickpea (SEQ ID NO:25; GI No.13487785), and is 99.6% identical to SEQ ID NO:26 (SEQ ID NO:248406 from U.S. Patent Application US2004031072).

The small subunit amino acid sequences of SEQ ID NOs:28, 30, 31 and 32 were aligned and the percent sequence identities were calculated for each pair of sequences. The soybean small subunit SS1 amino acid sequence of SEQ ID NO:28 is 94.6% identical to the small subunit polypeptide, PvAGPS1, of ADP-glucose pyrophosphorylase from *Phaseolus vulgaris* (SEQ ID NO:31; GI No. 29421116), and is 98.3% identical to SEQ ID NO:32 (SEQ ID NO:251944 from U.S. Patent Application US2004031072). The soybean small subunit SS2 amino acid sequence of SEQ ID NO:30 is 94.0% identical to the small subunit polypeptide, PvAGPS1, of ADP-glucose pyrophosphorylase from *Phaseolus vulgaris* (SEQ ID NO:31; GI No. 29421116), and is 100% identical to SEQ ID NO:32 (SEQ ID NO:251944 from U.S. Patent Application US2004031072). The soybean small subunit SS1 polypeptide (SEQ ID NO:28) and the SS2 polypeptide (SEQ ID NO:30) have 98.3% sequence identity with each other.

Sequence alignments and percent identity calculations were performed using the Megalign program of the LASERGENE bioinformatics computing suite (DNASTAR Inc., Madison, Wis.). Multiple alignment of the sequences was performed using the Clustal V method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5.

Sequence alignments and BLAST scores and probabilities indicate that the nucleic acid fragments comprising the instant cDNA clones encode full-length polypeptides for the large and small subunits of ADP-glucose pyrophosphorylase from soybean.

What is claimed is:

1. A method for producing transgenic seed, the method comprising:
   (a) transforming a plant cell with a recombinant DNA construct comprising:
      (i) all or part of the nucleotide sequence set forth in SEQ ID NO:7; or
      (ii) the full-length complement of (i);
      wherein (i) or (ii) is of sufficient length to inhibit expression of endogenous phosphoglucomutase activity in a transgenic plant;
   (b) regenerating a transgenic plant from the transformed plant cell of (a); and
   (c) selecting a transgenic plant that produces a transgenic mature seed having an increase in combined oil and protein content of 1.0-3.5%, on a dry-weight basis, as compared to mature seed obtained from a non-transgenic plant.

2. A method for producing transgenic seed, the method comprising:
   (a) transforming a plant cell with a recombinant DNA construct comprising:
      (i) all or part of the nucleotide sequence set forth in SEQ ID NO:7; or
      (ii) the full-length complement of (i);
      wherein (i) or (ii) is of sufficient length to inhibit expression of endogenous phosphoglucomutase activity in a transgenic plant;
   (b) regenerating a transgenic plant from the transformed plant cell of (a); and
   (c) selecting a transgenic plant that produces a transgenic mature seed having a sucrose to raffinose family oligosaccharide ratio that is decreased, on a dry-weight basis, as compared to mature seed obtained from a non-transgenic plant.

3. A method for producing defatted meal from transgenic seed, the method comprising:
   (a) transforming a plant cell with a recombinant DNA construct comprising:
      (i) all or part of the nucleotide sequence set forth in SEQ ID NO:7; or
      (ii) the full-length complement of (i);
      wherein (i) or (ii) is of sufficient length to inhibit expression of endogenous phosphoglucomutase activity in a transgenic plant;
   (b) regenerating a transgenic plant from the transformed plant cell of (a); and
   (c) selecting a transgenic plant that produces a transgenic mature seed wherein said mature seed is processed into defatted meal wherein the mature seed and defatted meal have a combined mature seed oil and defatted meal protein content that has an increase of 3.20-5.17%, on a dry-weight basis, as compared to defatted meal obtained from mature seed of a non-transgenic plant.

4. A method for producing transgenic seed, the method comprising:
   (a) transforming a plant cell with a recombinant DNA construct comprising:
      (i) all or part of the nucleotide sequence set forth in SEQ ID NO:7; or
      (ii) the full-length complement of (i);
      wherein (i) or (ii) is of sufficient length to inhibit expression of endogenous phosphoglucomutase activity in a transgenic plant;
   (b) regenerating a transgenic plant from the transformed plant cell of (a); and
   (c) selecting a transgenic plant that produces a transgenic mature seed having a decrease in sucrose content of 29.36-48.27%, on a dry-weight basis, as compared to mature seed obtained from a non-transgenic plant.

5. A method for producing defatted meal from transgenic seed, the method comprising:
   (a) transforming a plant cell with a recombinant DNA construct comprising:
      (i) all or part of the nucleotide sequence set forth in SEQ ID NO:7; or
      (ii) the full-length complement of (i);
      wherein (i) or (ii) is of sufficient length to inhibit expression of endogenous phosphoglucomutase activity in a transgenic plant;
   (b) regenerating a transgenic plant from the transformed plant cell of (a); and
   (c) selecting a transgenic plant that produces a transgenic mature seed wherein said mature seed is processed into defatted meal wherein the defatted meal has a decrease in sucrose content of 28.58-36.22%, on a wet-weight basis, as compared to defatted meal obtained from mature seed of a non-transgenic plant.

6. The method of any one of claims 1, 2, 3, 4 or 5, wherein the transgenic mature seed is obtained from a transgenic dicot plant comprising in its genome the recombinant construct.

7. The method of claim 6 wherein the dicot plant is soybean.

* * * * *